(12) United States Patent
Messmer et al.

(10) Patent No.: US 9,539,321 B2
(45) Date of Patent: Jan. 10, 2017

(54) HMGB1-DERIVED PEPTIDES ENHANCE IMMUNE RESPONSE TO ANTIGENS

(71) Applicant: The Regents of the University of California, Oakland, CA (US)

(72) Inventors: Davorka Messmer, San Diego, CA (US); Rebecca Saenz, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/642,527

(22) Filed: Mar. 9, 2015

(65) Prior Publication Data

US 2015/0306213 A1    Oct. 29, 2015

Related U.S. Application Data

(62) Division of application No. 13/812,455, filed as application No. PCT/US2011/045620 on Jul. 27, 2011, now Pat. No. 8,999,349.

(Continued)

(51) Int. Cl.
*A61K 39/00*    (2006.01)
*A61K 39/39*    (2006.01)
(Continued)

(52) U.S. Cl.
CPC .............. *A61K 39/39* (2013.01); *A61K 9/0019* (2013.01); *A61K 38/08* (2013.01); *A61K 38/10* (2013.01); *A61K 39/0011* (2013.01); *C07K 7/06* (2013.01); *A61K 38/00* (2013.01); *A61K 2039/55505* (2013.01); *A61K 2039/55516* (2013.01); *A61K 2039/55555* (2013.01); *A61K 2039/57* (2013.01); *A61K 2039/575* (2013.01)

(58) Field of Classification Search
CPC ...... A61K 39/39; A61K 9/0019; A61K 38/08; A61K 38/10; A61K 39/0011; C07K 7/06
See application file for complete search history.

(56) References Cited

U.S. PATENT DOCUMENTS 5,033,252 A    7/1991    Carter
5,052,558 A    10/1991    Carter
(Continued)

OTHER PUBLICATIONS

Agresti, Alessandra and Marco E. Bianchi, "HMGB proteins and gene expression," *Current Opinion in Genetics & Development*, 2003, 13:170-8 (Exhibit 4).
(Continued)

*Primary Examiner* — Cherie M Stanfield
(74) *Attorney, Agent, or Firm* — Joseph R. Baker, Jr.; Gavrilovich, Dodd & Lindsey LLP

(57) ABSTRACT

The invention provides an immtmostimulatory peptide containing the amino acid sequence SAFFLFCSE and uses thereof.

The invention also provides an immunostimulatory peptide containing the amino acid sequence DPNAPKRPPSAFFLX$_1$X$_2$X$_3$X$_4$ or derivatives thereof. In one embodiment, when X1 is alanine (A), glycine (G), or valine (V) then X2 is C, X3 is S and X4 is E; wherein when X2 is alanine (A), glycine (G), or valine (V) then X1 is F, X3 is S and X4 is E; wherein when X3 is alanine (A), glycine (G), or valine (V) then X1 is F, X2 is C and X4 is E; or wherein when X4 is alanine (A), glycine (G), or valine (V) then X1 is F, X2 is C and X3 is S.

11 Claims, 26 Drawing Sheets

Related U.S. Application Data

(60) Provisional application No. 61/400,448, filed on Jul. 27, 2010.

(51) Int. Cl.
*A61K 9/00* (2006.01)
*C07K 7/06* (2006.01)
*A61K 38/08* (2006.01)
*A61K 38/10* (2006.01)
*A61K 38/00* (2006.01)

(56) References Cited

U.S. PATENT DOCUMENTS 5,323,907 A    6/1994    Kalvelage
7,288,250 B2   10/2007   Newman et al. .......... 424/133.1

OTHER PUBLICATIONS

Alexopoulou, Lena et al., "Recognition of double-stranded RNA and activation of NF-B by Toll-like receptor 3," *Nature*, 2001, 413:732-8 (Exhibit 5).
Andersson, Ulf et al., "High Mobility Group 1 Protein (HMG-1) Stimulates Proinflammatory Cytokine Synthesis in Human Monocytes," *J. Exp. Med.*, 2000, 192:565-70 (Exhibit 6).
Audibert, Françoise M. and Luc D. Lise, "Adjuvants: current status, clinical perspectives and future prospects," *Immunology Today*, 1993, 14:281-4 (Exhibit 7).
Banchereau, Jacques and Ralph M. Steinman, "Dendritic cells and the control of immunity," *Nature*, 1998, 392:245-52 (Exhibit 8).
Basu, Sreyashi et al., "Necrotic but not apoptotic cell death release heat shock proteins, which deliver a partial maturation signal to dendritic cells and activate the NF-B pathway," *International Immunology*, 2000, 12:1539-46 (Exhibit 9).
Bianchi, Marco E., "DAMPs, PAMPs and alarmins: all we need to know about danger," *Journal of Leukocyte Biology*, 2007, 81:1-5 (Exhibit 10).
Bienkiewicz, Ewa A. et al., "Conformation of the RNA Polymerase II C-Terminal Domain: Circular Dichroism of Long and Short Fragments," *J. Mol. Biol.*, 2000, 297:119-33 (Exhibit 11).
Brazolot Millan, Cynthia L. et al., "CpG DNA can induce strong Th1 humoral and cell-mediated immune responses against hepatitis B surface antigen in young mice," *Proc. Natl. Acad. Sci. USA*, 1998, 95:15553-8 (Exhibit 12).
Brewer, James M. et al., "In interleukin-4-deficient mice, alum not only generates T helper 1 responses equivalent to Freund's complete adjuvant, but continues to induce T helper 2 cytokine production," *Eur. J. Immunol.*, 1996, 26:2062-6 (Exhibit 13).
Chen, Guo-Yun et al., "CD24 and Siglec-10 Selectively Repress Tissue Damage-Induced Immune Responses," *Science*, 2009, 323:1722-5 (Exhibit 14).
Chisari, Francis V. and Carlo Ferrari, "Hepatitis B Virus Immunopathogenesis," *Annu Rev Immunol*, 1995, 13:29-60 (Exhibit 15).
Chu, Rose S. et al., "CpG Oligodeoxynucleotides Act as Adjuvants that Switch on T Helper 1 (Th1) Immunity," *J. Exp. Med.*, 1997, 186:1623-31 (Exhibit 16).
De Gregorio, Ennio et al., "Alum adjuvanticity: Unraveling a century old mystery," *European Journal of Immunology*, 2008, 38:2068-71 (Exhibit 17).
Dredge, Keith et al., "Adjuvants and the promotion of Th1-type cytokines in tumour immunotherapy," *Cancer Immunol Immunother*, 2002, 51:521-31 (Exhibit 18).
Dumitriu, Ingrid E. et al., "Requirement of HMGB1 and RAGE for the maturation of human plasmacytoid dendritic cells," *European Journal of Immunology*, 2005, 35:2184-90 (Exhibit 19).
Dumitriu, Ingrid E. et al., "Release of High Mobility Group Box 1 by Dendritic Cells Controls T Cell Activation via the Receptor for Advanced Glycation End Products," *The Journal of Immunology*, 2005, 174:7506-15 (Exhibit 20).
Engers, Howard et al., "Third meeting on Novel Adjuvants Currently in or Close to Clinical Testing World Health Organization," *Vaccine*, 2003, 21:3503-24 (Exhibit 21).
Fernández-Carneado, J. et al., "Fatty acyl moieties: improving Pro-rich peptide uptake inside HeLa cells," *J. Peptide Res.*, 2005, 65:580-90 (Exhibit 22).
Gallucci, Stefania et al., "Natural adjuvants: Endogenous activators of dendritic cells," *Nature Medicine*, 1999, 5:1249-55 (Exhibit 23).
Gallucci, Stefania and Polly Matzinger, "Danger signals: SOS to the immune system," *Current Opinion in Immunology*, 2001, 13:114-9 (Exhibit 24).
Gupta, Rajesk K. and George R. Siber, "Adjuvants for human vaccines—current status, problems and future prospects," *Vaccine*, 1995, 13:1263-76 (Exhibit 25).
Gupta, Rajesh K., "Aluminum compounds as vaccine adjuvants," *Advanced Drug Delivery Reviews*, 1998, 32:155-72 (Exhibit 26).
Gurer, Cagan et al., "Targeting the nuclear antigen 1 of Epstein-Barr virus to the human endocytic receptor DEC-205 stimulates protective T-cell responses," *Blood*, 2008, 112:1231-9 (Exhibit 27).
Hoppe, George et al., "Molecular basis for the redox control of nuclear transport of the structural chromatin protein Hmgb1," *Experimental Cell Research*, 2006, 312:3526-38 (Exhibit 28).
Hori, Osamu et al., "The Receptor for Advanced Glycation End Products (RAGE) Is a Cellular Binding Site for Amphoterin," The Journal of Biological Chemistry, 1995, 270:25752-61 (Exhibit 29).
Hreggvidsdottir, Hulda Sigridur et al., "The alarmin HMGB1 acts in synergy with endogenous and exogenous danger signals to promote inflammation," *Journal of Leukocyte Biology*, 2009, 86:655-62 (Exhibit 30).
Huttunen, Henri J. et al., "Receptor for Advanced Glycation End Products (RAGE) Signaling Induces CREB-dependent Chromogranin Expression during Neuronal Differentiation," *The Journal of Biological Chemistry*, 2002, 277:38635-46 (Exhibit 31).
Inaba, Kayo et al., "Generation of Large Nos. of Dendritic Cells from Mouse Bone Marrow Cultures Supplemented with Granulocyte/Macrophage Colony-stimulating Factor," *J. Exp. Med.*, 1992, 176:1693-702 (Exhibit 32).
Ivanov, Stanimir et al., "A novel role for HMGB1 in TLR9-mediated inflammatory responses to CpG-DNA," *Blood*, 2007, 110:1970-81 (Exhibit 33).
Jasani, B. et al. "Ampligen: A potential toll-like 3 receptor adjuvant for immunotherapy of cancer," *Vaccine*, 2009, 27:3401-4 (Exhibit 34).
Kadowaki, Norimitsu et al., "Subsets of Human Dendritic Cell Precursors Express Different Toll-like Receptors and Respond to Different Microbial Antigens," *J. Exp. Med.*, 2001, 194:863-9 (Exhibit 35).
Kagan, Jonathan C. et al., "TRAM couples endocytosis of Toll-like receptor 4 to the induction of interferon-b," *Nature Immunology*, 2008, 9:361-8 (Exhibit 36).
Kovarik, Jiri and Claire-Anne Siegrist, "The Search for Novel Adjuvants for Early Life Vaccinations: Can 'Danger' Motifs Show Us the Way," *Archivum Immunologiae et Therapiae Experimentalis*, 2001, 49:209-15 (Exhibit 37).
Krieg, Arthur M., "CpG Motifs in Bacterial DNA and Their Immune Effects," *Annu. Rev. Immunol.*, 2002, 20:709-60 (Exhibit 38).
Krieg, Arthur M., "Therapeutic potential of Toll-like receptor 9 activation," *Nature Reviews*, 2006, 5:471-84 (Exhibit 39).
Krug, Anne et al., "Toll-like receptor expression reveals CpG DNA as a unique microbial stimulus for plasmacytoid dendritic cells which synergizes with CD40 ligand to induce high amounts of IL-12," *Eur. J. Immunol.*, 2001, 31:3026-37 (Exhibit 40).
Li, Jianhua et al., "Structural Basis for the Proinflammatory Cytokine Activity of High Mobility Group Box 1," *Molecular Medicine*, 2003, 9:37-45 (Exhibit 41).
Li, Shawn S.-C., "Specificity and versatility of SH3 and other proline-recognition domains: structural basis and implications for cellular signal transduction," *Biochem. J.*, 2005, 390:641-53 (Exhibit 42).
Linardakis, Emmanouela et al., "Enhancing the Efficacy of a Weak Allogeneic Melanoma Vaccine by Viral Fusogenic Membrane Glycoprotein-mediated Tumor Cell-Tumor Cell Fusion," *Cancer Research*, 2002, 62:5495-504 (Exhibit 43).

(56) References Cited

OTHER PUBLICATIONS

Loskog, Angelica and Thomas H. Tötterman, "CD40L—A Multipotent Molecule for Tumor Therapy," *Endocrine, Metabolic & Immune Disorders—Drug Targets*, 2007, 7:23-8 (Exhibit 44).

Matzinger, Polly, "Tolerance, Danger, and the Extended Family," *Annu. Rev. Immunol.*, 1994, 12:991-1045 (Exhibit 45).

Messmer, Davorka et al., "High Mobility Group Box Protein 1:An Endogenous Signal for Dendritic Cell Maturation and Th1 Polarization," *The Journal of Immunology*, 2004, 173:307-13 (Exhibit 46).

Milev, Peter et al., "High Affinity Binding and Overlapping Localization of Neurocan and Phosphacan/Protein-tyrosine Phosphatase-z/b with Tenascin-R, Amphoterin, and the Heparin-binding Growth-associated Molecule," *The Journal of Biological Chemistry*, 1998, 273:6998-7005 (Exhibit 47).

Netea, Mihai G. et al., "Toll-like receptors and the host defense against microbial pathogens: bringing specificity to the innate-immune system," *Journal of Leukocyte Biology*, 2004, 75:749-55 (Exhibit 48).

Núñez Miguel, Ricardo et al., "A Dimer of the Toll-like Receptor 4 Cytoplasmic Domain Provides a Specific Scaffold for the Recruitment of Signalling Adaptor Proteins," *PLoS ONE*, 2007, 8:e788 (Exhibit 49).

Orlova, Valeria V. et al., "A novel pathway of HMGB1-mediated inflammatory cell recruitment that requires Mac-1-integrin," *The EMBO Journal*, 2007, 26:1129-39 (Exhibit 50).

Park, Jong Sung et al., "Involvement of Toll-like Receptors 2 and 4 in Cellular Activation by High Mobility Group Box 1 Protein," *The Journal of Biological Chemistry*, 2004, 279:7370-7 (Exhibit 51).

Park, Jong Sung et al., "High mobility group box 1 protein interacts with multiple Toll-like receptor," *Am J Physiol Cell Physiol*, 2006, 290:C917-24 (Exhibit 52).

Petrovsky, Nikolai and Julio César Aguilar, "Vaccine adjuvants: Current safe and future trends," *Immunology and Cell Biology*, 2004, 82:488-96 (Exhibit 53).

Pujals, Silvia and Ernest Giralt, "Proline-rich, amphipathic cell-penetrating peptides," *Advanced Drug Delivery Reviews*, 2008, 60:473-84 (Exhibit 54).

Rauvala, Heikki and Ari Rouhiainen, "Physiological and pathophysiological outcomes of the interactions of HMGB1 with cell surface receptors," *Biochimica et Biophysica Acta*, 2010, 1799:164-70 (Exhibit 55).

Rovere-Querini, Patrizia et al., "HMGB1 is an endogenous immune adjuvant released by necrotic cells," *EMBO Reports*, 2004, 5:825-30 (Exhibit 56).

Saenz, R. et al., "HMGB1-derived peptide acts as adjuvant inducing immune response to peptide and protein antigen," *Vaccine*, 2010, 28:7556-62 (Exhibit 57).

Salmivitra, Markku et al., "Neurite Growth-Promoting Protein (Amphoterin, p30) Binds Syndecan," *Experimental Cell Research*, 1992, 200:444-51 (Exhibit 58).

Sauter, Birthe et al., "Consequence of Cell Death: Exposure to Necrotic Tumor Cells, but Not Primary Tissue Cells or Apoptotic Cells, Induces the Maturation of Immunostimulatory Dendritic Cells," *J. Exp. Med.*, 2000, 191 :423-33 (Exhibit 59).

Scaffidi, Paola et al., "Release of chromatin protein HMGB1 by necrotic cells triggers inflammation," *Nature*, 2002, 418:191-195 (Exhibit 60).

Schmidt, Charlie, "Clinical setbacks for toll-like receptor 9 agonists in cancer," *Nature Biotechnology*, 2007, 25:825-6 (Exhibit 61).

Seong, Seung-Yong and Polly Matzinger, "Hydrophobicity: an ancient damage-associated molecular pattern that initiates innate immune responses," *Nature Reviews*, 2004, 4:469-78 (Exhibit 62).

Siegal, Frederick P. et al., "The Nature of the Principal Type 1 Interferon-Producing Cells in Human Blood," *Science*, 1999, 284:1835-7 (Exhibit 63).

Singh, Manmohan and Derek O'Hagan, "Advances in vaccine adjuvants," *Nature Biotechnology*, 1999, 17:1075-81 (Exhibit 64).

Singh, Manmohan and Derek T. O'Hagan, "Recent Advances in Vaccine Adjuvants," *Pharmaceutical Research*, 2002, 19:715-28 (Exhibit 65).

Takeda, Kiyoshi et al., "Toll-like Receptors," *Annu. Rev. Immunol.*, 2003, 21:335-76 (Exhibit 66).

Taniai, Madoka et al., "N-terminal amino acid sequence of a major allergen of Japanese cedar pollen (Cry j I)," *FEBS*, 1988, 239:329-32 (Exhibit 67).

Telusma, Gloria et al., "Dendritic cell activating peptides induce distinct cytokine profiles," *International Immunology*, 2006, 18:1563-73 (Exhibit 68).

Trumpfheller, Christine et al., "The microbial mimic poly IC induces durable and protective CD4+ T cell immunity together with a dendritic cell targeted vaccine," *PNAS*, 2008, 105:2574-9 (Exhibit 69).

Tsung, Allan et al. "HMGB1 release induced by liver ischemia involves Toll-like receptor 4-dependent reactive oxygen species production and calcium-mediated signaling," *The Journal of Experimental Medicine*, 2007, 204:2913-23 (Exhibit 70).

Ulloa, Luis and Davorka Messmer, "High-mobility group box 1 (HMGB1) protein: Friend or foe," *Cytokine & Growth Factor Reviews*, 2006, 17:189-201 (Exhibit 71).

van Hoist, Gerrit-Jan and Geoffrey B. Fincher, "Polyproline II Confirmation in the Protein Component of Arabinogalactan-Protein from *Lolium multiflorum,*" *Plant Physiol.*, 1984, 75:1163-4 (Exhibit 72).

van Zoelen, Marieke A.D. et al., "Role of Toll-like Receptors 2 and 4, and the Receptor for Advanced Glycation End Products in High-Mobility Group Box 1-Induced Inflammation In Vivo," *Shock*, 2009, 31:280-4 (Exhibit 73).

Wang, Haichao et al., "Proinflammatory cytokines (tumor necrosis factor and interleukin 1) stimulate release of high mobility group protein-1 by pituicytes," *Surgery*, 1999, 126:389-92 (Exhibit 74).

Watts, Colin, "Location, location, location: identifying the neighborhoods of LPS signaling," *Nature Immunology*, 2008, 9:343-5 (Exhibit 75).

Weiner, George J. et al., "Immunostimulatory oligodeoxynucleotides containing the CpG motif are effective as immune adjuvants in tumor antigen immunization," *Proc. Natl. Acad. Sci. USA*, 1997, 94:10833-7 (Exhibit 76).

Wong, Brian R. et al., "TRANCE (Tumor Necrosis Factor [TNF]-related Activation-induced Cytokine), a New TNF Family Member Predominantly Expressed in T cells, Is a Dendritic Cell-specific Survival Factor," *J. Exp. Med.*, 1997, 186:2075-80 (Exhibit 77).

Xu-Amano, Jiangchun et al., "Helper T Cell Subsets from Immunoglobulin A Responses: Oral Immunization with Tetanus Toxoid and Cholera Toxin as Adjuvant Selectively Induces Th2 Cells in Mucosa Associated Tissues," *J Exp Med*, 1993, 178:1309-20 (Exhibit 78).

Yang, Huan et al., "HMGB1 as a cytokine and therapeutic agent," *Journal of Endotoxin Research*, 2002, 8:469-72 (Exhibit 79).

Yang, Huan et al., "A critical cysteine is required for HMGB1 binding to Toll-like receptor 4 and activation of macrophage cytokine release," *PNAS*, 2010, 107:11942-7 (Exhibit 80).

Yasueda, Hiroshi et al., "Isolation and partial characterization of the major allergen from Japanese cedar (*Cryptomeria japonica*) pollen," *J Allergy Clin Immunol*, 1983, 71:77-86 (Exhibit 81).

Yu, Hongtao et al., "Structural Basis for the Binding of Proline-Rich Peptides to SH3 Domains," *Cell*, 1994, 76:933-45 (Exhibit 82).

Yu, Man et al. "HMGB1 Signals Through Toll-like Receptor (TLR) 4 and TLR2," *Shock*, 2006, 26:174-9 (Exhibit 83).

Zaro, Jennica L. and Wei-Chiang Shen, "Quantitative comparison of membrane transduction and endocytosis of oligopeptides," *Biochemical and Biophysical Research Communications*, 2003, 307:241-7 (Exhibit 84).

Taudte et al., (Biochem J. 2000. 347:807-814).

Salqueiro et al., (Biochemistry. Aug. 14, 2001;40(32):9709-16, Abstract only).

Santos-Aguado et al., (Mol Cell Biol. Mar. 1987;7(3):982-90, Abstract only).

UniProt P09429 (HMGB1_Human), especially residues 91-108 (Jul. 1, 1989, last sequence update Jan. 23, 2007).

HMGB1-DERIVED PEPTIDES ENHANCE IMMUNE RESPONSE TO ANTIGENS

This invention was made with government support under Grant No. W81XWH-07-1-0412 awarded by U.S. Army Medical Research and Materiel Command and Grant No. 5 U54 CA119335 awarded by National Institutes of Health/National Cancer Institute. The government has certain rights in the invention.

This application is a divisional of U.S. Ser. No. 13/812, 455, filed Jan. 25. 2013, which is a 35 U.S.C. §371 application of PCT application No. PCT/US2011/045620, filed Jul. 27, 2011, which claimed the priority of U.S. Ser. No. 61/400,448, filed Jul. 27, 2010, the contents of all of which are hereby incorporated by reference in their entirety into the present application. Throughout this application various publications are referenced. The disclosures of these publications in their entireties are hereby incorporated by reference into this application in order to more fully describe the state of the art to which this invention pertains.

BACKGROUND OF THE INVENTION

Vaccines traditionally have, and still consist of whole-inactivated or live-attenuated pathogens or toxins [1,2]. The usage of these modified pathogens is, however, unattractive for several reasons. Live attenuated pathogens can cause disease by reverting to a more virulent phenotype, especially in the non-developed immune system of newborns or immunodeficient patients, and whole inactivated pathogens contain reactogenic components that can cause undesirable vaccine side effects. Therefore, there is growing interest and research to develop a new generation of vaccines containing recombinant protein subunits, synthetic peptides, and plasmid DNA [1]. While these new modalities promise to be less toxic, many are poorly immunogenic when administered without an immune-stimulating adjuvant. As adjuvants are a crucial component of the new generation of vaccines, there is a great need for safer and more potent adjuvants [1-3].

The development of the appropriate type of immune response is essential for successful immunization. Robust cell-mediated immunity, which is associated with a Th1 type immune response, is thought to be required for the control of intracellular pathogens [4], viruses [5] as well as cancer [6]. Humoral immunity, characterized by a Th2 type response is useful for vaccination against extracellular pathogens, such as bacteria. By choosing an appropriate adjuvant, the immune response can be selectively modulated to initiate a Th1 or Th2-type [7]. Aluminum salts (alum), which are the only vaccine adjuvants currently approved by the US Food and Drug Administration for use in humans [8,9] are not ideal adjuvants for certain pathogens, since they favor a Th2 response with weak or absent Th1 responses [10-14]. Although neutralizing antibodies from a Th2 response can be protective against many pathogens, the generation of Th1 and cytotoxic T lymphocyte (CTL) responses are important, playing crucial roles in the protection and recovery from viruses, intracellular bacteria, and cancer cells.

Pathogen associated molecular patterns (PAMPs) are small molecular sequences commonly associated with pathogens, such as CpG unmethylated bacterial DNA sequences, lipopolysaccharide (LPS), or poly(I:C) [15-18]. While many PAMPs have been investigated for their use as vaccine adjuvants, their development has been slowed for several reasons, including reactogenicity, toxicity, and ability to induce or exacerbate autoimmune diseases [19]. For instance, CpG oligodeoxynucleotides, which signal through TLR9, can activate antigen-presenting cells, induce a wide variety of cytokines, and generate a potent cellular Th1 immune response in mice, initially showed strong clinical promise [20-23]. However, clinical trials in humans utilizing CpG as a cancer immunotherapy adjuvant failed to produce the potent immune responses that were anticipated, and low TLR9 expression in human plasmacytoid DCs may be implicated [24]. Identification of new adjuvants demonstrating low-toxicity and the ability to stimulate a cellular Th1 response in humans would be a great advancement in the development of vaccines for infectious disease and cancer.

In contrast to PAMPs, endogenous molecules and proteins have been proposed and studied as adjuvants. Examples of such endogenous molecules, or danger-associated molecular patterns (DAMPs), include heat stock proteins, cytokines, and high mobility group box 1 (HMGB1) protein [25,26]. Originally identified as a nuclear protein, HMBG1 modulates the innate immune response when released into the extracellular compartment by necrotic and damaged cells [27,28]. HMGB1 is a potent pro-inflammatory cytokine, released by monocytes and macrophages following exposure to LPS, tumor necrosis factor (TNF)-α or IL-1β and as a result of tissue damage [27,29]. Extracellular HMGB1 promotes the maturation of myeloid and plasmacytoid DCs [30-32] and it has been shown to act as immune adjuvant by enhancing immunogenicity of apoptotic lymphoma cells and eliciting antibody responses to soluble ovalbumin protein [33].

We have previously identified a short peptide, named Hp91, within the B box domain of HMGB1 that induces activation of human and mouse DCs [25]. Hp91-activated DCs show increased secretion of pro-inflammatory cytokines and chemokines, including the Th1 cytokine, IL-12. In addition, DCs exposed to HMGB1-derived peptides induced proliferation of antigen-specific syngeneic T cells in vitro [25]. Here we show novel immunostimulatory peptides act as adjuvants in vivo by enhancing immune responses to peptide and protein antigen.

SUMMARY OF THE INVENTION

The invention provides an immunostimulatory peptide containing the amino acid sequence SAFFLFCSE (SEQ ID NO: 1) and uses thereof.

The invention also provides an immunostimulatory peptide containing the amino acid sequence DPNAPKRPPSAFFLX$_1$X$_2$X$_3$X$_4$ (SEQ ID NO: 9) or derivatives thereof. In one embodiment, when X1 is alanine (A), glycine (G), or valine (V) then X2 is C, X3 is S and X4 is E; wherein when X2 is alanine (A), glycine (G), or valine (V) then X1 is F, X3 is S and X4 is E; wherein when X3 is alanine (A), glycine (G), or valine (V) then X1 is F, X2 is C and X4 is F; or wherein when X4 is alanine (A), glycine (G), or valine (V) then X1 is F, X2 is C and X3 is S.

In an embodiment of the invention, the derivative is an immunostimulatory peptide having the amino acid sequence RPPSAFFLX$_1$X$_2$X$_3$X$_4$ (SEQ ID NO: 14), wherein when X1 is alanine (A), glycine (G), or valirte (V) then X2 is C, X3 is S and X4 is E; wherein when X2 is alanine (A), glycine (G), or valine (V) then X1 is F, X3 is S and X4 is E; wherein when X3 is alanine (A), glycine (G), or valine (V) then X1 is F, X2 is C and X4 is E; or Wherein when X4 is alanine (A), glycine (G), or valine (V) then X1 is F, X2 is C and X3 is S.

In another embodiment, the derivative is an immtmostimulatory peptide having the amino acid sequence SAFFLX$_1$X$_2$X$_3$X$_4$ (SEQ ID NO: 4), wherein when X1 is Amine (A), glycine (G), or valine (V) then X2 is C, X3 is S and X4 is E; wherein when X2 is alanine (A), glycine (G), or valine (V) then X1 is F, X3 is S and X4 is E; wherein when X3 is alanine (A), glycine (G), or valine (V) then X1 is F, X2 is C and X4 is E; or wherein when X4 is alanine (A), glycine (G), or valine (V) then X1 is F, X2 is C and X3 is S.

Other embodiments of SAFFLX$_1$X$_2$X$_3$X$_4$ (SEQ ID NO: 4) include those having the amino acid sequence: SAFFLX$_1$CSE (SEQ ID NO: 5), SAFFLFX$_1$SE (SEQ ID NO: 6), SAFFLFCX$_1$E (SEQ ID NO: 7), SAFFLFCSX$_1$ (SEQ ID NO: 8), wherein X$_1$ is alanine (A), glycine (G), or valine (V). In a further embodiment, SAFFLX$_1$X$_2$X$_3$X$_4$ is further mutated so that F at amino acid positions 3 and/or 4 is changed to S.

DETAILED DESCRIPTION OF THE INVENTION

DEFINITIONS

Figure 1:
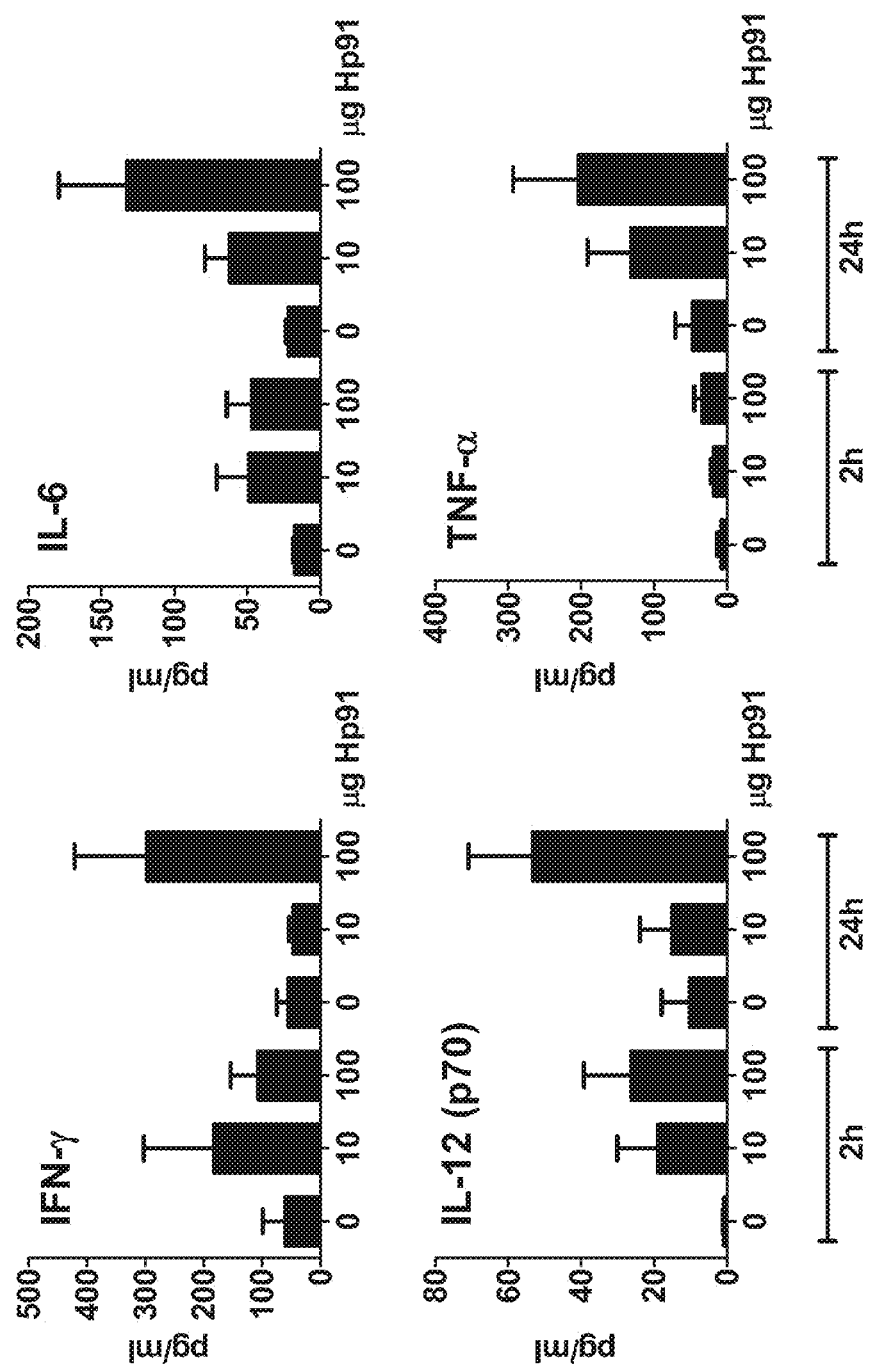
FIG. 1. Hp91 causes release of cytokines in vivo. Mice were injected i.v. into the tail vein with Hp91 (10 or 100 μg) or PBS (denoted as 0 μg Hp91). Blood was collected after 2 and 24 h and serum was analyzed for IFN-γ, IL-6, IL-12 (p70), and TNF-α by ELISA. Data shown are mean (+/− SEM) from 3-4 mice per group.

All scientific and technical terms used in this application have meanings commonly used in the art unless otherwise specified. As used in this application, the following words or phrases have the meanings specified.

As used herein, a "derivative" is a molecule that shares sequence similarity and activity of its parent molecule, e.g.

DPNAPKRPPSAFFLX$_1$X$_2$X$_3$X$_4$ (SEQ ID NO: 9) or SAFFLX$_1$X$_2$X$_3$X$_4$ (SEQ ID NO: 4). A fragment may be considered a derivative. Also, the derivative may include an immunostimulatory peptide of the invention as part of a larger protein or polypeptide (e.g., a heterologous protein (in one example, the protein is not a HMBG1 protein)). A derivative may include any change to the amino acid sequence and/or chemical quality of the amino acid e.g., amino acid analogs. For example, a derivative of DPNAPKRPPSAFFLX$_1$X$_2$X$_3$X$_4$ or SAFFLX$_1$X$_2$X$_3$X$_4$ may include a molecule having an amino acid sequence at least 70% similar to DPNAPKRPPSAFFLX$_1$X$_2$X$_3$X$_4$ or SAFFLX$_1$X$_2$X$_3$X$_4$, and/or increases the immunogenicity of any antigen admixed therewith or joined thereto and/or activates the adaptive and/or innate immune system (e.g., induces the costimulatory signal necessary for activation of lymphocytes). The derivative may also maintain an alpha helix conformation.

As used herein, "administer" or "administering" to a subject includes but is not limited to tumoral administration, intratumoral administration, peritumoral administration, intravenous (i.v.) administration, intraperitoneal tip.) administration, intramuscular (i.m.) administration, subcutaneous administration, oral administration, inhalation administration, topical administration, administration by injection, as a suppository, or the implantation of a slow-release device such as a miniosmotic pump, or administration by slow release devices such as vesicles or capsules to the subject.

As used herein, "subject" means any living organism to which the agents can be administered in order to regulate an immune response. Subjects may include, but are not limited to, humans, monkeys, cows, goats, sheep, mice, rats, cats, dogs, hamsters, and any transgenic animals.

As used herein, "pharmaceutically acceptable carrier" means any material that may be combined with an immunostimulatory peptide(s) of the invention (or derivatives thereof) (and/or compositions/vaccines/adjuvants including them) in order to administer them to a subject in any form. For example, a carrier includes any material that will maintain the agents' effective activity when administered to a subject and that is non-reactive with a subject's immune system. Potential carriers may include, but are not limited to, any solvents, media, suspensions, emulsions or other excipients such as starch, milk, sugar, certain types of clay, gelatin, stearic acids, stearate salts, talcum, oils, gums, glycols, flavorings, preservatives or color additives, etc. Potential carrier forms may include sterile solutions, aerosols, liposomes, vesicles, suppositories, pills, tablets or capsules.

In order that the invention herein described may be more fully understood the following description is set forth.

COMPOSITIONS OF THE INVENTION

The invention provides an immunostimulatory peptide containing the amino acid sequence SAFFLFCSE SEQ ID NO: 1). In another embodiment, the immunostimulatory peptide consists of the amino acid sequence SAFFLFCSE (SEQ ID NO: 1).

The invention also provides an immunostimulatory peptide containing the amino acid sequence DPNAPKRPPSAFFLX$_1$X$_2$X$_3$X$_4$ (SEQ ID NO: 9) or derivatives thereof. In one embodiment, when X1 is any of the amino acid alanine (A), glycine (0), or valine (V) then X2 is cysteine (C), X3 is serine (S) and X4 is glutamic acid (E); wherein when X2 is alanine (A), glycine (G), or valine (V) then X1 is phenylalanine (F), X3 is S and X4 is E; wherein when X3 is alanine (A), glycine (G), or vahne (V) then X1 is F, X2 is C and X4 is E; or wherein when X4 is alanine (A), glycine (G), or valine (V) then X1 is F, X2 is C and X3 is S. In a further embodiment, X1 may be alanine (A), glycine (0), valine (V), isoleucine (I), or leucine (L) and X2 is cysteine (C), X3 is serine (S) and X4 is glutamic acid (E). In another embodiment, X1 is phenylalanine (F); X2 may be alanine (A), glycine (G), valine (V), isoleucine (I), or leucine (L); X3 is S and X4 is E. In a yet further embodiment, X1 is phenylalanine (F); X2 is cysteine (C); X3 may be alanine (A), glycine (G), valine (V), isoleucine (I), or leucine (L); and X4 is E. In a still further embodiment, X1 is F; X2 is C; X3 is S; and X4 may he alanine (A), glycine (G), valine (V), isoleucine (I), or leucine (L). A list of the amino acids and their one letter symbol is found supra.

In an embodiment of the invention, the derivative may be an immunostimulatory peptide having the amino acid sequence RPPSAFFLX$_1$X$_2$X$_3$X$_4$ (SEQ ID NO: 14) wherein when X1 is alanine (A), glycine (G), or valine (V) then X2 is C, X3 is S and X4 is E; wherein when X2 is alanine (A), glycine (G), or valine (V) then X1 is F, X3 is S and X4 is E; wherein when X3 is alanine (A), glycine (G), or valine (V) then X1 is F, X2 is C and X4 is E; or wherein when X4 is alanine (A), glycine (G), or valine (V) then X1 is F, X2 is C and X3 is S.

In another embodiment, the derivative may be an immunostimulatory peptide having the amino acid sequence SAFFLX$_1$X$_2$X$_3$X$_4$ (SEQ ID NO: 4). In an embodiment of SAFFLX$_1$X$_2$X$_3$X$_4$, when X1 is alanine (A), glycine (G), or valine (V) then X2 is C, X3 is S and X4 is E; wherein when X2 is alanine (A), glycine (G), or valine (V) then X1 is F, X3 is S and X4 is E; wherein when X3 is alanine (A), glycine (G), or valine (V) then X1 is F, X2 is C and X4 is E; or wherein when X4 is alanine (A), glycine (G), or valine (V) then X1 is F, X2 is C and X3 is S. In another embodiment, X1 may be alanine (A), glycine (G), valine (V), isoleucine (I), or leucine (L) and X2 is cysteine (C), X3 is serine (S) and X4 is glutamic acid (E). In another embodiment, X1 is phenylalanine (F); X2 may be alanine (A), glycine (G), valine (V), isoleucine (I), or leucine (L); X3 is S and X4 is E. In a further embodiment, X1 is phenylalanine (F); X2 is cysteine (C); X3 may be alanine (A), glycine (G), valine (V), isoleucine (I), or leucine (L); and X4 is E. In a still further embodiment, X1 is F; X2 is C; X3 is S; and X4 may be alanine (A), glycine (G), valine (V), isoleucine (I), or leucine (L). In a yet further embodiment, SAFFLX$_1$X$_2$X$_3$X$_4$ may be further mutated so that F at amino acid positions 3 and/or 4 is changed to S.

Other embodiments of SAFFLX$_1$X$_2$X$_3$X$_4$ include those having the amino acid sequence: SAFFLX$_1$CSE (SEQ ID NO: 5), SAFFLFX$_1$SE (SEQ ID NO: 6). SAFFLFCX$_1$E (SEQ ID NO: 7), or SAFFLFCSX$_1$ (SEQ ID NO: 8), wherein X$_1$ is alanine (A), glycine (G), or valine (V).

The immunostimulatory peptides of the invention (or its derivatives) may be monomeric, dimeric, trimeric, or tetrameric. Particular dimeric embodiments include, but are not limited to, dimeric SAFFLFCSE (SEQ ID NO: 1), dimeric DPNAPKRPPSAFFLX$_1$X$_2$X$_3$X$_4$ (SEQ ID NO: 9), dimeric RPPSAFFLX$_1$X$_2$X$_3$X$_4$ (SEQ ID NO: 14), and dimeric SAFFLX$_1$X$_2$X$_3$X$_4$ (SEQ ID NO: 4). Dimeric peptides of the invention may be hornodimeric or heterodimeric.

The immunostimulatory peptides of the invention (or its derivatives) may be soluble (i.e., circulating) or bound to a cell surface. The immunostimulatory peptides of the invention (or its derivatives) can be made synthetically or recombinantly.

The immunostimulatory peptide (or its derivatives) may also exhibit an alpha helix conformation. In one embodiment, the alpha helix conthrmation may provide a circular dichroism profile that shows negative peaks at about 205-207 nm and/or 222 nm. Further, the alpha helix conformation may provide a circular dichroism profile that shows a positive peak below about 200 nm.

In accordance with the practice of the invention, SAFFLX$_1$X$_2$X$_3$X$_4$ (SEQ ID NO: 4) molecules may include a non-SAFFLX$_1$X$_2$X$_3$X$_4$ attached or joined thereto. For example, additional peptide sequences may be added or joined to the N-terminal or C-terminal end of SAFFLX$_1$X$_2$X$_3$X$_4$. In one embodiment, the immunostimulatory peptide SAFFLX$_1$X$_2$X$_3$X$_4$ further conTrises on its N-terminal portion the amino acid sequence arginine (R), proline (P), and proline (P). This immunostimulatory peptide has the sequence RPPSAFFLX$_1$X$_2$X$_3$X$_4$ (SEQ ID NO: 14). X$_1$, X$_2$, X$_3$ and X$_4$ may be any of the amino acids alanine (A), glycine (G), valine (V), isoleucine (I), or leucine (L) as described above.

In another embodiment, the immunostimulatory peptide DPNAPKRPPSAFFLX$_1$X$_2$X$_3$X$_4$ (SEQ ID NO: 9) may be further mutated so that F at amino acid positions 12 and/or 13 is changed to S.

Specific examples of the immunostimulatory peptide, SAFFLX$_1$X$_2$X$_3$X$_4$ include, but are not limited to SAFFLX$_1$CSE (SEQ ID NO: 5), SAFFLFX$_1$SE (SEQ ID NO: 6), SAFFLFCX$_1$E (SEQ ID N0: 7), or SAFFLFCSX$_1$ (SEQ ID NO: 8), wherein X$_1$ may be alanine (A), glycine (G), valine (V), isoleucine (I), or leucine (L). Preferred examples include SAFFLACSE (SEQ ID NO: 31) and SAFFLFASE (SEQ ID NO: 32).

Specific examples of the immunostimulatory peptide, RPPSAFFLX$_1$X$_2$X$_3$X$_4$, include, but are not limited to RPPSAFFLX$_1$CSE (SEQ ID NO: 15), RPPSAFFLFX$_1$SE (SEQ ID NO: 16) RPPSAFFLFCX$_1$E (SEQ ID NO: 17), or RPPSAFFLFCSX$_1$ (SEQ ID NO: 18), wherein X$_1$ may be alanine (A), glycine (G), valine (V), isoleucine (I), or leucine (L). Preferred examples include RPPSAFFLACSE (SEQ ID NO: 37) and RPPSAFFLFASE (SEQ ID NO: 38).

In a further embodiment, the immunostimulatory peptide RPPSAFFLX$_1$X$_2$X$_3$X$_4$ is further mutated so that F at amino acid positions 6 and/or 7 is changed to S.

In accordance with the practice of this invention, the peptides of the invention may have additional amino acid substitutions in the amino acid sequence especially, for example, corresponding to the X$_1$ X$_2$ X$_3$ X$_4$ domain (of e.g. DPNAPKRPPSAFFLX$_1$X$_2$X$_3$X$_4$ or SAFFLX$_1$X$_2$X$_3$X$_4$) so as to produce molecules which would retain the functional property of DPNAPKRPPSAFFLX$_1$X$_2$X$_3$X$_4$ or SAFFLX$_1$X$_2$X$_3$X$_4$, namely, the molecule having such substitutions will stiil maintain an aloha helix conformation and/or increase the immunogenicity of any antigen admixed therewith or joined thereto and/or activates the adaptive and/or innate immune system (e.g., induces the costimulatory sig al necessary for activation of lymphocytes. The mutation(s) may include one or more amino acid residues substituted with an amino acid having conservative (e.g., substitute a leucine with an isoleucine) or non-conservative (e.g., substitute a glycine with a tryptophan) structure or chemical properties, amino acid deletions, additions, frameshilts, or truncations.

For example, it is a well-established principle of protein chemistry that certain amino acid substitutions, entitled "conservative amino acid substitutions," can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine and valine (V).

Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

A mutation in DNA may change a codon leading to a change in the amino acid sequence. A DNA change may include substitutions, deletions, insertions, alternative splicing, or truncations. An amino acid change may include substitutions, deletions, insertions, additions, truncations, or processing or cleavage errors of the protein. Alternatively, mutations in a nucleotide sequence may result in a silent mutation in the amino acid sequence as is well understood in the art. In that regard, certain nucleotide codons encode the same amino acid. Examples include nucleotide codons CGU, CGG, CGC, and CGA encoding the amino acid, arginine (R); or codons GAU, and GAC encoding the amino acid, aspartic acid (D). Thus, a protein can be encoded by one or more nucleic acid molecules that differ in their specific nucleotide sequence, but still encode protein molecules having identical sequences. The amino acid coding sequence is as follows:

| Amino Acid | Symbol | One Letter Symbol | Codons |
|---|---|---|---|
| Alanine | Ala | A | GCU, GCC, GCA, GCG |
| Cysteine | Cys | C | UGU, UGC |
| Aspartic Acid | Asp | D | GAU, GAC |
| Glutamic Acid | Glu | E | GAA, GAG |
| Phenylalanine | Phe | F | UUU, UUC |
| Glycine | Gly | G | GGU, GGC, GGA, GGG |
| Histidine | His | H | CAU, CAC |
| Isoleucine | Ile | I | AUU, AUC, AUA |
| Lysine | Lys | K | AAA, AAG |
| Leucine | Leu | L | UUA, UUG, CUU, CUC, CUA, CUG |
| Methionine | Met | M | AUG |
| Asparagine | Asn | N | AAU, AAC |
| Proline | Pro | P | CCU, CCC, CCA, CCG |
| Glutamine | Gln | Q | CAA, CAG |
| Arginine | Arg | R | CGU, CGC, CGA, CGG, AGA, AGG |
| Serine | Ser | S | UCU, UCC, UCA, UCG, AGU, AGC |
| Threonine | Thr | T | ACU, ACC, ACA, ACG |

-continued

| Amino Acid | Symbol | One Symbol | Letter Codons |
|---|---|---|---|
| Valine | Vat | V | GUU, GUC, GUA, GUG |
| Tryptophan | Trp | W | UGG |
| Tyrosine | Tyr | Y | UAU, UAC |

The peptides of the invention may comprise amino acids that are naturally occurring or non-naturally occurring. The natural amino acid in the wild-type polypeptide may be replaced with a desired non-natural amino acid.

As used herein, a "natural amino acid" is the 20 naturally occurring amino acids, namely glycine, alanine, valine, leucine, isoleucine, serine, threonine, aspartic acid, glutamic acid, asparagine, glutamine, lysine, arginine, cysteine, methionine, phenylalanine, tyrosine, tryptophan, histidine and proline.

As used herein, the term "non-natural amino acid" refers to an organic compound that has a structure similar to a natural amino acid but has been modified structurally to mimic the structure and/or reactivity of a natural amino acid. Thus, all amino acids but the natural 20 amino acids are referred to as non-natural amino acids even if they are naturally present (e.g. hydroxyproline).

The immunostimulatory peptides of the invention (or derivatives thereof) may be joined to a tag or crosslinking agent (e.g. a non-immunogenic tag or crosslinking agent). Merely by way of example, the tag or crosslinking agent may be any of polyalkylene glycol (PAG) (e.g., linear or branched polyalkylene glycol) and a lipid. The polyalkylene glycol may be a polyethylene glycol (PEG).

The invention also provides compositions comprising the immunostimulatory peptides of the invention (or derivatives thereof) combined with nanoparticles or microparticles and/or a pharmaceutically acceptable carrier.

The invention further provides vaccine formulations comprising an antigen (e.g. a heterologous antigen) and an immunostimulatory peptide of the invention (or a derivative thereof). The antigen may he admixed with the immunostimulatory peptide of the invention or joined thereto. The vaccine may include combinations of the immunostimulatory peptides of the invention. The vaccine induces an immune response to the specific antigen admixed therewith or joined thereto. A heterologous antigen is an antigen that is not normally or naturally found adjacent to the immunostimulatory peptides of the invention or its parent molecule.

Suitable examples of antigens include but are not limited to respiratory disease antigens, tumor related antigens, allergy related antigens, and cardiovascular disease antigens. In other embodiments, the antigen is a non-viral environmental irritant. In one embodiment, the antigen is an allergen. In other embodiments, the antigen may he from a bacteria, fungus, mold, dust mite, animal dander or pollen antigen, or a combination thereof. As used herein, antigen includes derivatives or portions of antigens that are immunogenic.

In one embodiment, the respiratory disease antigen may be a respiratory virus antigen. The viral antigens may be inactivated or attenuated. Examples of suitable respiratory viruses include but are not limited to rhinoviruses, influenza viruses, coronavirus RSV, or any combination thereof. Examples of influenza viruses include H1N1, H1N2, HlN7, H2N2, H3N1, H3N2, H3N8, H4N8, H5N1 H5N2, H5N3, H5N8, H5N9, H6N5, H7N1, H7N2, H7N3, H7N4, H7N7, H8N4, H9N2, H10N7, H11N6, H12N5, H13N6, H14N5, and any other subtypes arising from re-assortment between influenza A viruses. Additional examples of respiratory viruses include a coronavirus (e.g., SARS virus), RSV, or a combination thereof.

Specific examples of allergen-related protein antigens useful in the methods and compositions of the present invention include, but are not limited to: allergens derived from pollen, such as those derived from trees such as Japanese cedar (*Cryptomeria, Cryptomeria japonica*), grasses (*Gramineae*), such as orchard-grass (*Dactylis, Daetylis glomerata*), weeds such as ragweed (*Ambrosia, Ambrosia artemisiffiblia*); specific examples of pollen allergens including the Japanese cedar pollen allergens (J Allergy Clin Immunol. (1983) 71: 77-86) and (FEBS Letters (1988) 239: 329-332), and the ragweed allergens Amb a 1.1, Amba 1.2, Amb a 1.3, Amb a 1.4, Amb a I1 etc.; allergens derived from fungi (*Aspergillus, Candida*, 41ternatia, etc.); allergens derived from mites (allergens from Dermatophagoidespteronyssinus, Derinatophagoidesfarinae etc.; specific examples of mite allergens including Der p I, Der p II, Der p III, Der p VII, Der f I, Der f II, Der f III, Der f VII etc.); house dust; allergens derived from animal skin debris, feces and hair (for example, the feline allergen Fel d 1), allergens derived from insects (such as scaly hair or scale of moths, butterflies, Chironomidae etc., poisons of the Vespidae, such as Vespa maizdarinia); food allergens (eggs, milk, meat, seafood, beans, cereals, fruits. nuts and vegetables etc.); allergens derived from parasites (such as roundworm and nematodes, for example, *Anisakis*); and protein or peptide based drugs (such as insulin). Many of these allergens are commercially available.

In certain embodiments, the vaccine formulation (or composition (e.g., comprising the antigen and the immunostimulatory peptide of the invention, together or separate)) may be formulated for use in a child or adult subject.

The vaccine formulation of the invention may further comprise nanoparticles or microparticles. The nanoparticles may be hybrid PLGA-natloparticles, vesosomes or liposome nanoparticles.

The vaccine formulation may further include an adjuvant, which includes but is not limited to, Alum (e.g., aluminum hydroxide or aluminum phosphate) (Brenntag Biosector A/S), CpG oligodeoxynucleotides (or CpG ODN) (Integrated DNA Technologies), polyinosinic-polycytidylic acid [poly(I:C)] (Invivogen), 2,6,10,15,19,23-Hexamethyltetracosa-2,6,10,14,18,22-hexaene (squalene), monophosphoryl lipid A (MPL), CD40L (e.g. gp39 or anti-cd40 ab), and/or IL-2.

The invention additionally provides adjuvants comprising the immunostimulatory peptide of the invention (or derivatives thereof) so as to increase the immunogenicity of an antigen admixed therewith or joined thereto. The adjuvant may further comprise nanoparticles or microparticles. In accordance with the practice of the invention, the nanoparticles may be hybrid PLGA-nanoparticles, vesosomes or liposome nanoparticles.

METHODS OF THE INVENTION

Additionally, the invention further provides methods for inducing cytotoxic T lymphocytes (CTLs), in one embodiment, the method comprises contacting or subjecting T cells with an immunostimulatory peptide(s) of the invention (or derivatives thereof) (and/or compositions/vaccines/adjuvants including them) in an amount sufficient to induce CTL proliferation or growth.

The invention also provides methods for enhancing an immune response sy administering to the subject an immunostimulatory peptides of the invention (or derivatives thereof) (and/or compositions/vaccines/adjuvants including them) in an amount sufficient to enhance an immune response in the subject.

In accordance with the practice of the invention, the methods may be an ex vivo method, an in vivo method, or an in vitro method.

The invention also provides methods of enhancing an immune response in a subject. In one embodiment, the method comprises administering a sufficient amount of the immunostimulatory peptide of the invention (or derivatives thereof) (and/or compositions/vaccines/adjuvants including them) thereby enhancing the immune response in the subject.

In one embodiment, the invention provides methods for selectively eliciting a cell-mediated immune response but not a humoral immune response in a subject. In one embodiment, the method comprises administering a sufficient amount of the vaccine fomiulation of the invention thereby enhancing the cell-mediated immune response in the subject.

In another embodiment, the invention provides methods for selectively eliciting a cell-mediated immune response and a humoral immune response in a subject. In one embodiment, the method comprises administering a sufficient amount of the vaccine formulation of the invention thereby enhancing the cell-mediated and humoral immune response in the subject.

The invention further provides methods of inhibiting tumor growth associated with a cancerous disease. In one embodiment, the method comprises administering to a subject an immunostimulatory peptide of the invention (or derivatives thereof) (and/or compositions/vaccines/adjuvants including them) in an amount sufficient to inhibit tumor growth in the subject.

In another embodiment, the invention provides methods for reducing the tumor size of a tumor associated with a cancerous disease. The method provides administering to a subject an immunostimulatory peptide of the invention (or derivatives thereof) (and/or compositions/vaccines/adjuvants including them) in an amount sufficient to reduce the tumor size in a subject.

in a further embodiment, the invention provides methods for delaying the occurrence of a cancerous disease in a subject. The method comprises administering to the subject an immunostimulatory peptide of the invention (or derivatives thereof) (and/or compositions/vaccines/adjuvants including them) in a dose effective for delaying the occurrence of the cancerous disease.

In another embodiment, an effective amount of an alkylating agent is further administered to the subject prior to, concurrently, or after administering the immunostimulatory peptide of the invention (or derivatives thereof) (and/or compositions/vaccines/adluvants including them). The alkylating agent may be a cyclophosphamide. Other alkylating agents may be used.

In an embodiment of the invention, an effective amount of the cyclophosphamide may be between 1 mg/m$^2$ and 500 mg/m$^2$. Other doses are possible. A further discussion is provided supra.

Examples of cancerous diseases include but are not limited to prostate cancer, prostate cancer metastasized to bone, ovarian cancer, tonsil cancer, bladder cancer, stomach cancer, kidney cancer, testicular cancer, small intestinal cancer, colon cancer, colorectal cancer, cervical cancer, uterine cancer, salivary cancer, throat cancer, bronchial cancer, head and neck cancer, adrenal cancer, neuroblastoma, pheochromocytoma, liver cancer, lung cancer, thyroid cancer, breast cancer, melanoma, schwannoma, neurofibrosarcoma, osteosarcoma, chondrosarcoma, liposarcoma, leiomyosarcorna, leukemia, lymphoma, and pancreatic cancer.

Administration of the immunostimulatory peptide of the invention (or derivatives thereof) (and/or compositions/vaccines/adjuvants including them) may be effected by a delivery system which includes, but is not limited to, an implantable pump, continuous infusion, gene therapy, liposomes, and injection. Additionally, administration may be effect by various administration means, e.g., oral administration, infratumoral administration, peri-tumoral administration, intravenous administration, intrarectal administration, intravaginal administration, intrabronchial administration, topical administration, intramuscular administration, intraperitoneal administration, intrapleural administration, by inhalation, by eye drops or by any enteral, parenteral or non-parenteral mechanism or means.

In accordance with the practice of the invention, the subject includes, but is not limited to, human, non-human primates, cows, pigs, horses, goats, sheep, rabbits, pigs, dogs, cats, mice, or rats.

Dosages

The appropriate dosage of immunostimulatory peptides of the invention (or derivatives thereof) (or compositions/vaccines/adjuvants including them) for use in accordance with the methods of the present invention may depend on a variety of factors. Such factors may include, but are in no way limited to, a subject's physical characteristics (e.g., age, weight, sex), whether the compound is being used as single agent or adjuvant therapy, the type of MHC restriction of the patient, the progression (i.e., pathological state) of the infection, and other factors that may be recognized by one Skilled in the art.

One skilled in the art would be able, by routine experimentation, to determine an effective, non-toxic amount of immunostimulatory peptides of the invention (or derivatives thereof) (or compositions/vaccines/adjuvants including them) which would be required to treat the subject. Generally, an effective dosage may be in the range of about 0.0001 mg to about 1000 mg per kg body weight per 24 hours.

Typically, in therapeutic applications, the treatment would he for the duration of the disease state or condition, Further, it will be apparent to one of ordinary skill in the art that the optimal quantity and spacing of individual dosages will he determined by the nature and extent of the disease state or condition being treated, the form, route and site of administration, and the nature of the particular individual being treated. Also, such optimum conditions can be determined by conventional techniques. It will also be apparent to one of ordinary skill in the art that the optimal course of treatment can be ascertained using conventional course of treatment determination tests.

Where two or more therapeutic entities are administered to a subject "in conjunction", they may be administered in a single composition at the same time, or in separate compositions at the same time or in separate compositions separated in time. In certain embodiments, the methods of the invention involve the administration of immunostimulatory peptides of the invention (or derivatives thereof) (or compositions/vaccines/adjuvants including them)) in multiple separate doses. Accordingly, the methods for the prevention (i.e. vaccination) and treatment described herein encompass the administration of multiple separated doses to a subject, for example, over a defined period of time. Accordingly, the methods for the prevention (i.e. vaccination) and treatment disclosed herein include administering a priming dose of immunostimulatory peptides of the invention (or derivatives thereof) (or compositions/vaccines/adjuvants including them). The priming dose may be followed by a booster dose. The booster may be for the purpose of revaccination. In various embodiments, the composition or vaccine is administered at least once, twice, three times or more.

KITS

According to another aspect of the invention, kits are provided. Kits according to the invention include package(s) or containers comprising an immunostimulatory peptides of the invention (or derivatives thereof) (or compositions/vaccines/adjuvants including them). The kit may further include an instruction letter for the treatment and/or prophylaxis of a disease, for example, a veterinary disease.

The phrase "package" means any vessel containing compounds or compositions presented herein. In preferred embodiments, the package can be a box or wrapping. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment.

The kit can also contain items that are not contained within the package but are attached to the outside of the package, for example, pipettes.

Kits may optionally contain instructions for administering compounds or compositions of the present invention to a subject having a condition in need of treatment. Kits may also comprise instructions for approved uses of compounds herein by regulatory agencies, such as the United States Food and Drug Administration. Kits may optionally contain labeling or product inserts for the present compounds. The package(s) and/or any product insert(s) may themselves be approved by regulatory agencies. The kits can include compounds in the solid phase or in a liquid phase (such as buffers provided) in a package. The kits also can include buffers for preparing solutions for conducting the methods, and pipettes for transferring liquids from one container to another.

The kit may optionally also contain one or more other compounds for use in combination therapies as described herein. In certain embodiments, the package(s) is a container for intravenous administration. In other embodiments, compounds are provided in an inhaler.

In still other embodiments compounds are provided in a polymeric matrix or in the form of a liposome.

The following examples are provided to further illustrate aspects of the invention. These examples are non-limiting and should not be construed as limiting any aspect of the invention.

EXAMPLES

Example 1

Materials and Methods
Reagents and Cell Lines

The OVA-transfected EL4 line, E.G7-OVA (ATCC, Manassas, Va., USA), was cultured in RPMI 1640 medium (Invitrogen, Carlsbad, Calif., USA) supplemented with 10% fetal bovine serum (FBS) (Omega Scientific, Tarzana, Calif., USA), 10 mM HEPES (Invitrogen), and penicillin (100 U ml$^{-1}$)—streptomycin (100 µg ml$^{-1}$)—L-glutamine (2 mM) (Invitrogen).

Peptides and Protein

The peptides, including the ISP Hp91 (DPNAPKRPPSAFFLFCSE) (SEQ ID NO: 2), Hp121 (SIGDVAKKLGEMWNNTAA) (SEQ ID NO: 47), the MHC-Class I (H-2K$^b$)-restricted peptide epitope of ovalbumin (OVA-I: OVA 257-264 aa, SIINFEKL (SEQ ID NO: 45)), and the MHC-Class II (I-A$^b$)-restricted peptide epitope of ovalbumin (OVA-II: OVA 323-339 aa, ISQAVHAAHAEINEAGR (SEQ ID NO: 46)) were all purchased from GenScript Corp (Piscataway, N.J., USA) and CPC Scientific (San Jose, Calif., USA). Hp91 and Hp121 peptides were synthesized with an N-terminal biotin. Peptides were routinely synthesized with greater than 95% purity. LPS-free chicken egg white ovalbumin protein was kindly provided by Dr. Thomas Moran (Department. of Microbiology, Mount Sinai School of Medicine, New York, N.Y., USA). Unless otherwise stated, all peptides and proteins were dissolved in PBS in preparation for immunization.

Mice and Immunizations

Female C57BL/6 mice 8-12 weeks of age were used for most experiments. All mice were purchased from Charles River Laboratories (Boston, Mass., USA) and housed at the Moores UCSD Cancer Center animal facility. All animal studies were approved by the Institutional Animal Care and Use Committee of UCSD and were perfolined in accordance with the institutional guidelines. For most experiments, mice were immunized s.c. with 50 µg of SIINFEKL (OVA-I) peptide (SEQ ID NO: 45) and 50 µg of ISQAVHAAHAEINEAGR (OVA-II) peptide (SEQ ID NO: 46). The OVA peptide was co-administered with either Hp91 (30 to 500 µg) or PBS (negative control). For some experiments, a protein vaccine group was included, wherein 500 µg of Hp91 was co-administered with 100 µg of LPS-free OVA protein. As a positive control, mice were immunized s.c. with OVA peptide(s) or protein in Incomplete Freund's Adjuvant "IFA" (Sigma-Aldrich, St. Louis, Mo., USA). If not otherwise indicated, mice were immunized and boosted two weeks later and spleens and blood were collected 10-14 days after the final immunization.

Intravenous Administration of ISP

C57BL/6 mice were injected i.v. with 0, 10 or 100 µg Hp91 dissolved in PBS into the tail vein. Blood was collected after 2 h and 24 h by retroorbital puncture. Blood was allowed to clot and serum was isolated after centrifugation. Serum was diluted and analyzed for systemic cytokine and chemokine release by ELISA (eBioscience, San Diceo, Calif., USA).

Detection of Antigen-Specific Antibody Production by ELISA

Serum was obtained by retroorbital puncture or cardiac puncture from mice following immunization. Blood was allowed to clot and serum was isolated after centrifugation Microtiter plates were coated overnight with OVA protein (Sigma-Aldrich), blocked with BSA, and dilutions of serum were added to the plates for incubation. Plates were washed, incubated with anti-mouse IgG or IgM peroxidase conjugated antibodies (Roche, Basel, Switzerland), developed using Zymed TMB substrate (Invitrogen), and analyzed using a microplate reader at 450 nm.

Spleen Cell Preparation

Single cell suspensions of splenocytes were prepared by mechanical disruption and separation through a 70 µm nylon cell strainer (BD Biosciences, Franklin Lakes, N.J., USA). Red blood cells were lysed using ammonium chloride buffer (Roche Diagnostics, Indianapolis, Ind., USA) and the splenocytes were subsequently resuspended in complete medium (RPMI 1640 with 10% FBS, L-glutamine, penicillin, streptomycin, and HEPES). in some experiments, CD4+ and CD8+ cells were depleted from bulk splenocyte populations using anti-CD4 or anti-CD8α conjugated microbeads (Miltenyi-Biotec, Auburn, Calif., USA) according to the manufacturer's instructions.

Enzyme-Linked Immunospot Assay

Freshly isolated splenocytes were plated in duplicate to wells of a nitrocellulose bottom enzyme-linked immunospot (ELISPOT) plate (Millipore, Millerica, Mass., USA) that had been previously coated overnight with 5 µg ml$^{-1}$ monoclonal anti-mouse IFN-γ antibody (Mabtech, Stockholm, Sweden). Splenocytes were cultured overnight at 37° C. with 2.5 µg ml$^{-1}$ SIINFEKL (OVA-I) peptide, 2.5 µg ml$^{-1}$ ISQAVHAAHAEINEAGR (OVA-II) peptide, or left unstimulated (medium only). After 18 h, culture supernatants were collected for cytokine analysis and ELISPOT plates were developed using 1 µg ml$^{-1}$ biotinylated anti-mouse IFN-γ antibody (Mabtech), Streptavidin-HRP (Mabtech), and TMB Substrate (Mabtech). The plate was scanned and the spots were counted using an automated ELISpot Reader System (CTL ImmunoSpot, Shaker Heights, Ohio, USA).

Measurement of Cytokines and Chemokines

Splenocytes were cultured overnight with 2.5 µg ml$^{-1}$ OVA-I peptide, 2.5 µg ml$^{-1}$ OVA-II peptide, 5 µg ml$^{-1}$ concanavalin A positive control (Sigma), or left unstimulated (media only). After 18 h, cell culture supernatants were collected and analyzed for the presence of IL-2 and IL-4 by ELISA (eBioscience).

LDH Cytotoxicity Assay

Splenocytes were expanded in culture at $3\times10^6$ cells ml$^{-1}$ in complete medium with mitomycin-C (Sigma-Aldrich)-treated E.G7-OVA at a 5:1 ratio in 6 well plates. Four days later, live cells were isolated on a lympholyte gradient (Cedarlane Laboratories Limited, Burlington, Ontario, Canada) and cultured in complete medium with 25 U ml$^{-1}$ IL-2 (R&D Systems, Minneapolis, Minn., USA) for two additional days. Cytotoxicity assays were performed using a CytoTox96 Non-Radioactive Cytotoxicity Assay Kit (Promega, Madison, Wis., USA). $1\times10^4$ E.G7-OVA cells per well were plated as target cells. Expanded splenocyte effector cells were incubated with the target cells at effector to target ratios of 1:1, 3:1, 10:1, and 30:1. Cultures were incubated in phenol-red free RPMI (Invitrogen) with 5% FBS (Omega) for 6 h at which point the cell culture supernatants were harvested. The lactate dehydrogenase (LDH) released from lysed cells was proportional to the resulting red fomiazan product, and was quantified using a microplate reader at 490 nm absorbance. The percentage of cytotoxicity was calculated according to the following equation: % Cytotoxicity [(E—St—Se)/(M—St)]×100. Abbreviations are as follow; E=LDH release by effector-target coculture, St=spontaneous release by target cells, Se=spontaneous release by effectors, and M=maximal release by target: cells.

Statistical Analysis

Data represented are mean ±SEM. Data were analyzed for statistical significance using unpaired Student's t-test, 2-way ANOVA, or linear regression. Statistical analyses were done using GraphPad software version 5.01 for Windows (GraphPad Software, San Diego, Calif., USA). A p value <0.05 was considered statistically significant fer these analyses.

Results

HP91 Induces Cytokine Release In Vivo

We have previously shown that exposure of DCs to an immunostimulatory peptide (ISP) named Hp91 in vitro leads to secretion of inflammatory as well as Th1 skewing cytokines[25]. To examine the adjuvant properties of Hp91 in vivo, serum cytokine responses were measured after intravenous (i.v.) injection of Hp91 into mice. Increased secretion of the Th1 cytokines IFN-γ, IL-12 (p70), as well as TNF-α was observed within 2 h of injection, with levels generally rising further over 24 h (FIG. 1).

Hp91 Enhances CD8 T Cell Responses to Peptide Antigen

Figure 2:
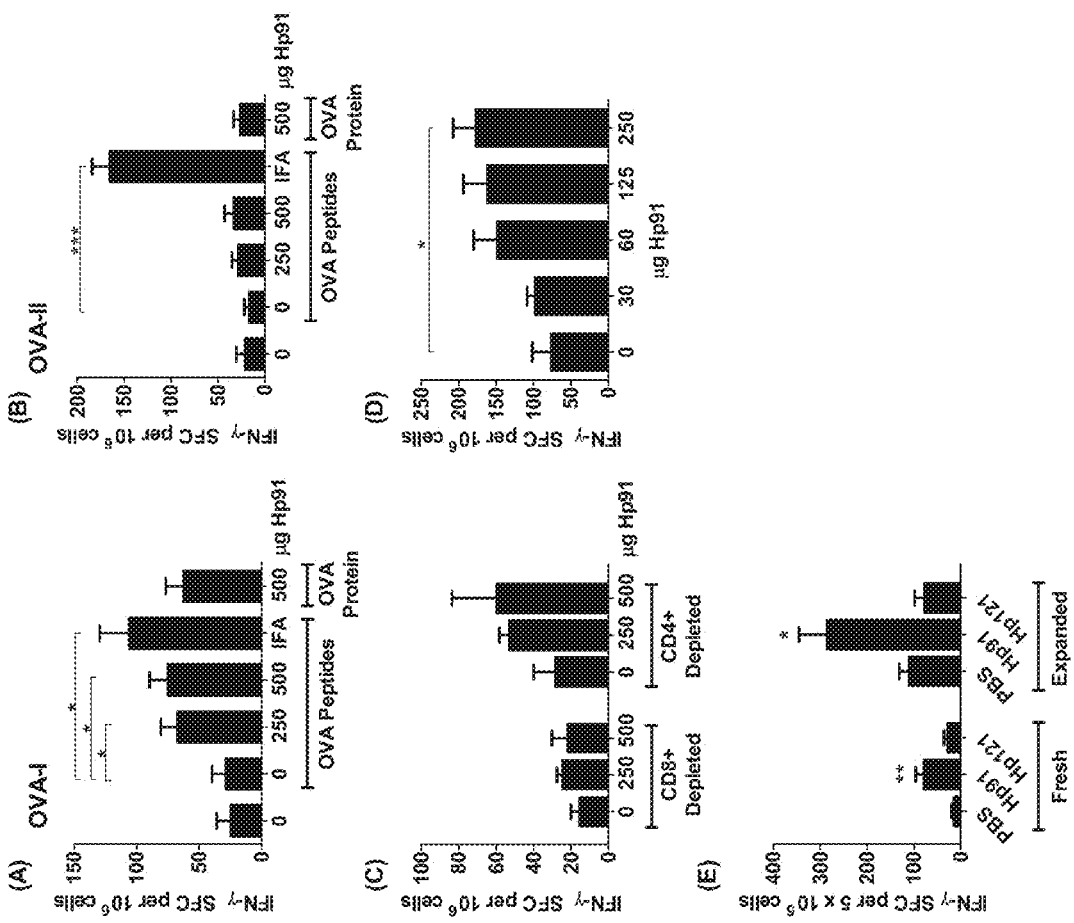
FIG. 2. Cellular immune response in Hp91 immunized mice. (A-B) Mice were immunized with OVA peptides in PBS (denoted as "0"), Hp91 (250 and 500 μg), or IFA. One group of mice was immonized with OVA protein and Hp91 (500 μg). Freshly-isolated spienocytes from the immunized mice were cultured in the presence of (A) OVA-I (SIINFEKL) peptide (SEQ NO: 45) (2.5 μg ml$^{-1}$) or (B) OVA-II (ISQAVHAAHAEINEAGR) (SEQ ID NO: 46) (2.5 μg ml$^{-1}$) in an IFN-γ ELISPOT assay. The number of IFN-γ-secreting cells was determined 18 hours later. The data shown (IFN-γ spot-forming cells per million cells) are means (+/− SEM) for 10 mice/group, except the Hp91-OVA protein group which is n=5. Asterisk, p<0.05 between groups; Student's t-test. Data are representative of at least 3 independent experiments. (C) Freshly isolated splenocytes from PBS/OVA-peptide and Hp91/OVA-peptide immunized mice were depleted of CD8+ or CD4+ T cells and stimulated overnight in the presence of 2.5 μg, ml$^{-1}$ OVA-I (SIINFEKL) peptide in an IFN-γ ELISPOT assay as above. Data shown are means (+/− SEM) for 5 mice per group. (D) Mice were immunized twice with OVA-I (SIINFEKL) peptide (50 μg) co-injected with 0, 30, 60, 125, or 250 μg Hp91 dissolved in PBS. Splenocytes from immunized mice were cultured in an OVA-I IFN-γ ELISPOT assay as above. Spleens were collected 6 days after the boost. Asterisk, p<0.05 between groups; Student's t-test compared to PBS. (E) Mice were immunized with OVA peptides in PBS, Hp91 or Hp121 (250 μg). Mice received an additional boost s.c. into the contralateral flank one month after the first boost. Freshly-isolated or OVA-I-expanded splenocytes were cultured in an OVA-I IFN-γ ELISPOT assay as above. The number of IFN-γ spot-forming cells is shown as means (+/− SEM) for 4 mice per group. Asterisks, (*<0.05 and **<0.005); 2-way ANOVA.

Since the ISP Hp91 activates DCs and induces antigen-specific T cell responses in vitro[25], we tested whether Hp91 acts as an adjuvant to induce antigen specific immune responses in vivo. The ISP Hp91 at both doses tested (250 µg and 500 µg) when co-administered with OVA peptides, caused a significant increase in the number of antigen-specific IFN-γ secreting T cells when splenocytes were restimulated with the CD8 epitope SIINFEKL (FIG. 2A), but not when restimulated with the CD4 epitope ISQAVHAAHAEINEAGR (FIG. 2B). Incomplete Freund's Adjuvant (IFA) a known stimulator of cell-mediated immune responses, elicited strong cellular immune responses wheal splenocytes were restimulated with either ate CD8 or CD4 epitope (FIG. 2A,B).

The OVA-I peptide (SIINFEKL) is recognized in the context of H-2K$^b$ MHC-Class I molecules and is specific for CD8+T cells. To thrther confirm that the observed immune response is an OVA-specific CD8+T cell response, CD4+ or CD8+ cells were depleted from the splenocytes prior to setup up the ELISPOT assay. While greater than 95% of CD4+ cells were depleted, CD8+ depletion was not as complete; 20% of CD8+ cells remained in the cultures as observed by flow cytometry. As expected, the number of IFN-γ secreting cells was reduced to near background levels (OVA peptides/PBS) in the CD8+ depleted spienocyte populations (FIG. 2C). In contrast to the CD8+depletion, the CD4+ depleted splenocytes from the Hp91-OVA immunized groups retained the ability to secrete IFN-γ in response to OVA-I peptide stimulation further supporting the involvement of CD8+T cells following co-immunization with the ISP Hp91 and OVA peptide showing that the ISP Hp91 causes activation and proliferation of antigen-specific CD8+T lymphocytes in vivo.

To test whether lower doses of Hp91 would suffice as adjuvant for immunization, titrated doses of Hp91 were co-injected with OVA peptide to determine the minimum injection dose required for a significant increase in antigen-specific IFN-γ secreting T cells. As expected, a dose response was observed (FIG. 2D). However, with only 5 mice per group, a significant increase in IFN-γ secreting T cells was observed by ELISPOT only in the group receiving an Hp91 dose of 250 µg, suggesting 250 µg is an optimal dose when immunizing small groups of mice. Subsequent experiments showing 500 µg of Hp91 were conducted prior to the titration experiment.

The ISP Adjuvant Effect is Sequence Specific

To test if the in vivo adjuvant effect is related to the sequence of Hp91 or if any peptide will cause similar effects, we used a control peptide named Hp121. Hp121 is also derived from HMGB1 B-box and has the same length, a similar charge, and isoelectric point as Hp91. Hp121 does not cause activation of human DCs [25] or mouse BM-DCs in vitro. Mice were immunized s.c. with OVA-I peptide co-injected with either Hp91, Hp121 or PBS control. Mice immunized with Hp91/OVA-I peptide showed a significantly increased number of INF-γ secreting cells as compared to the Hp121/OVA-I peptide and PBS/OVA-I peptide immunized mice using freshly isolated as well as expanded splenocytes (FIG. 2E). No significant increase was observed between the Hp121/OVA peptide and PBS/OVA peptide immunized groups.

Hp91 Induces Th1-Type Immune Response In Vivo

Figure 3:
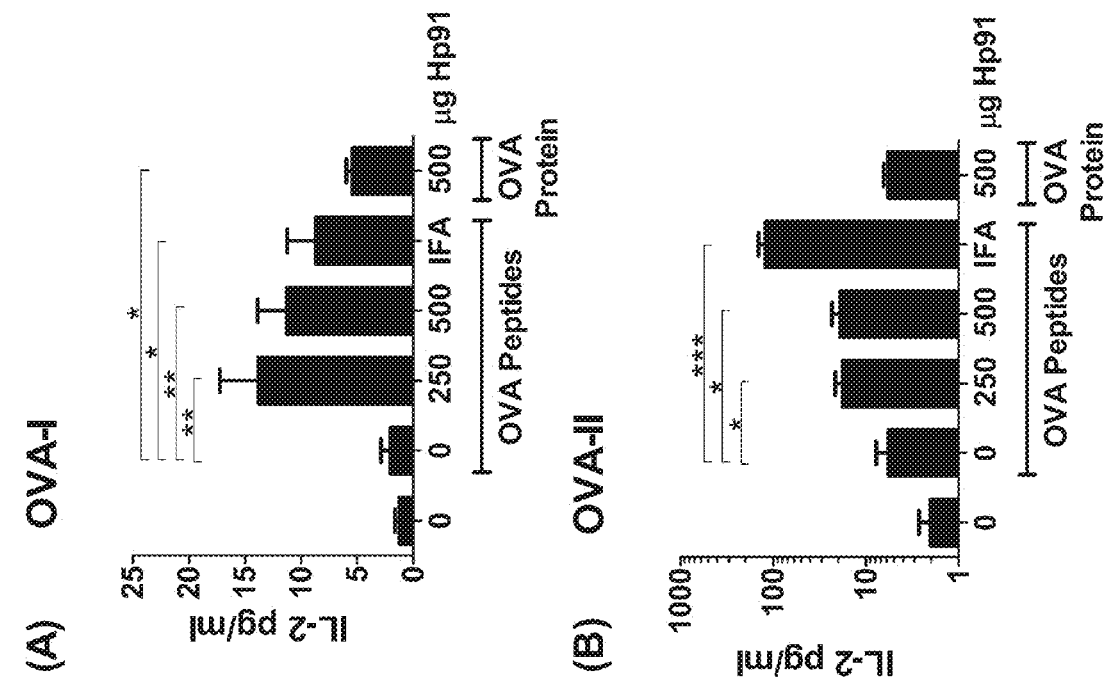
FIG. 3. Cytokine secretion in Hp91 immunized mice. Mice were immunized with OVA peptides (50 μg) co-injected with Hp91 (0, 250 or 500 μg dissolved in PBS) or IFA. One group of mice was immunized with OVA protein and Hp91 (500 μg) in PBS. Splenocytes from immunized mice were stimulated overnight with 2.5 μg ml$^{-1}$ of (A) OVA-I (SIINFEKL) peptide or (B) OVA-II (ISQAVHAAHAEINEAGR). Culture supernatants were collected and analyzed for IL-2 secretion by ELISA. Data shown are mean (+/− SEM) for 5-10 mice per group. Asterisk, p<0.05; Student's t-test.

Since IL-2 is critical for the activation, survival, and proliferation of T lymphocytes, we tested whether IL-2 secretion is increased in Hp91/OVA peptide immunized mice. Freshly isolated splenocytes were cultured overnight in presence of OVA peptide and culture supernatants were analyzed for IL-2 (FIG. 3) and IL-4, which may indicate the induction of a Th2 type immune response by ELISA. The highest IL-2 secretion was observed in OVA-I restimulated spienocytes from mice immunized with Hp91/OVA peptides (FIG. 3A), which showed higher IL-2 secretion compared to mice vaccinated with whole OVA protein/Hp91 or OVA peptide/IFA, both of which were also significantly increased as compared to the PBS/OVA control. After exposure to the MHC-Class II specific OVA-II peptide, spienocytes from Hp91/OVA peptide immunized mice showed a low but significant increase in IL-2 secretion as compared to PBS/OVA immunized mice (FIG. 3B). IL-4 was not detected in the splenocytes cultures at any of the conditions, though it was detected in the ConA stimulated positive control.

Hp91 Elicits Antibody Responses to Soluble Protein

Figure 4:
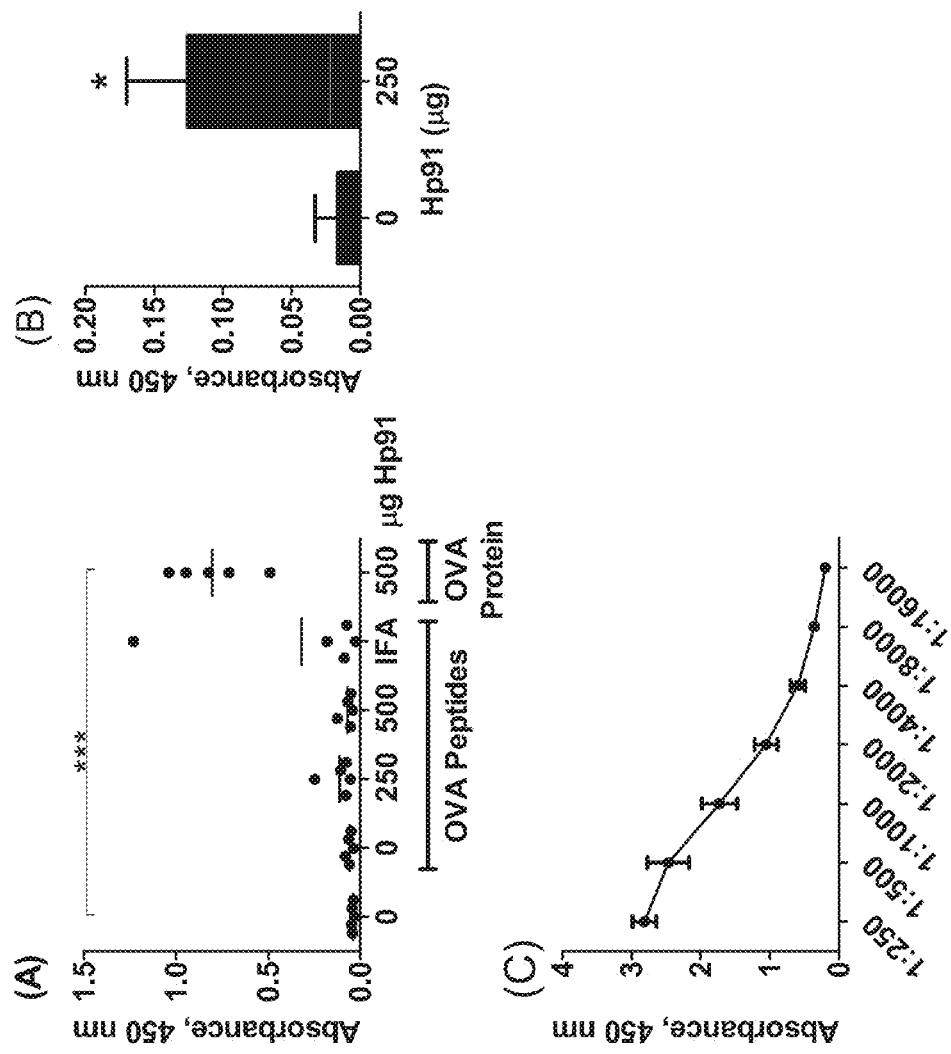
FIG. 4. Antibody responses in Hp91 immunized mice. Serum was obtained from immunized mice (5 mice per group) 10 days after the final immunization and analyzed for antibody levels by ELISA. (A) A 1:100 dilution of the serum from immunized mice as indicated, (B) a 1:100 dilution of serum from mice immunized with OVA protein and Hp91 (0 or 250 μg in PBS) or (C) a serial dilution of serum from mice immunized with OVA protein and Hp91 (500 μg) in PBS was added to the plates, followed by a peroxidase-conjugated anti-mouse IgG1 antibody. Plates were developed with TMB substrate and absorbance was analyzed on a microplate reader. Asterisks, p<0.001; Student's t-test.

Immunization using OVA protein in context of Hp91 promoted an antibody response to GVA which was dominated by the IgG1 isotype (FIG. 4A, 4B). Two-fold serial dilutions of the Hp91/OVA protein group show similar serum titers for the group (FIG. 4C). Minimal increase in IgG2b and IgM OVA specific antibodies was detected. Immunization using OVA peptides (OVA-I and OVA-II) together with Hp91 did not induce antibody responses (FIG. 4A).

Co-Administration of Hp91 with Antigen Induces CTL Responses

Figure 5:
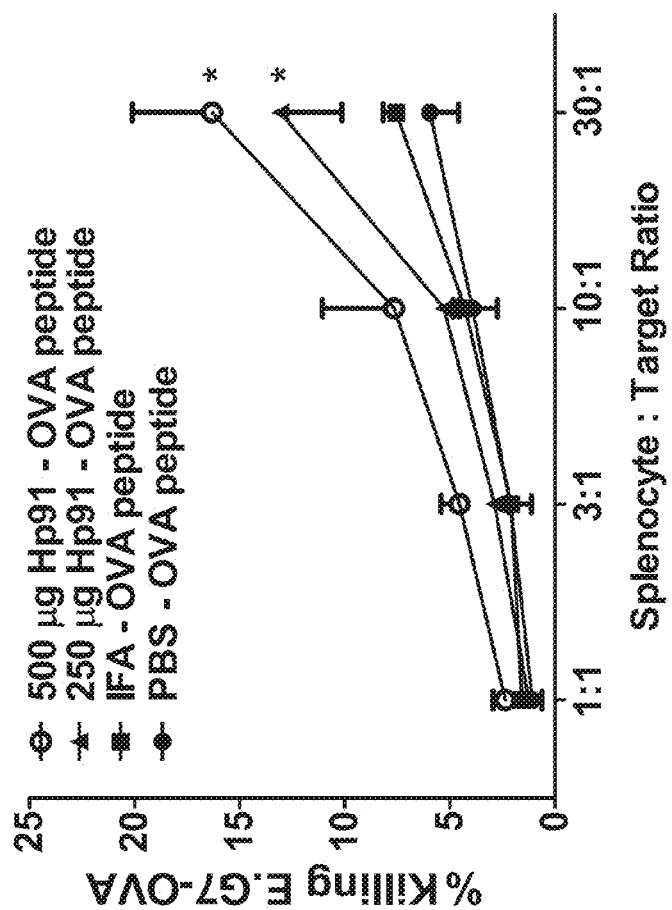
FIG. 5. CTL Induction in immunized mice. Expanded splenocytes from immunized mice were cultured with E.G7-OVA cells at the indicated effector to target ratios for 6 h. Cell culture supeniatants were collected and cytotoxicity was quantified in a CytoTox96 non-radioactive cytotoxicity assay. Data from at least 3 mice per group are shown. Data were analyzed by linear regression and slopes were compared for significance. Asterisk, p<0.05; compared to PBS.
Figure 6:
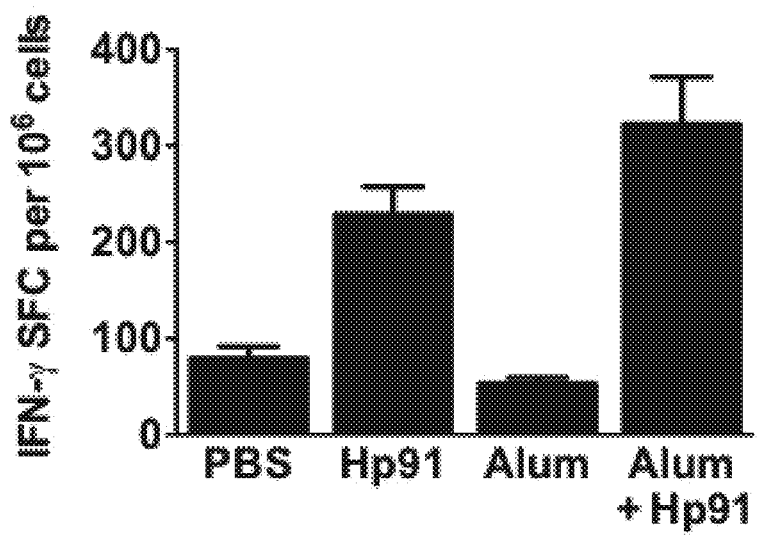
FIG. 6. Hp91/alum adjuvant synergy. Mice were primed and boosted two weeks later with OVA (SIINFEKL) peptide (50 μg) co-injected with PBS, Hp91 (250 μg), Alum (aluminum hydroxide or aluminum phosphate) (500 μg) (Brenntag Biosector A/S), or Hp91 mixed with alum. Splenocytes from immunized mice were stimulated overnight with 2.5 μg ml$^{-1}$ of OVA (SIINFEKL) peptide in an IFN-γ ELISPOT assay. The number of IFN-γ-secreting cells was determined 18 hours later.
Figure 7:
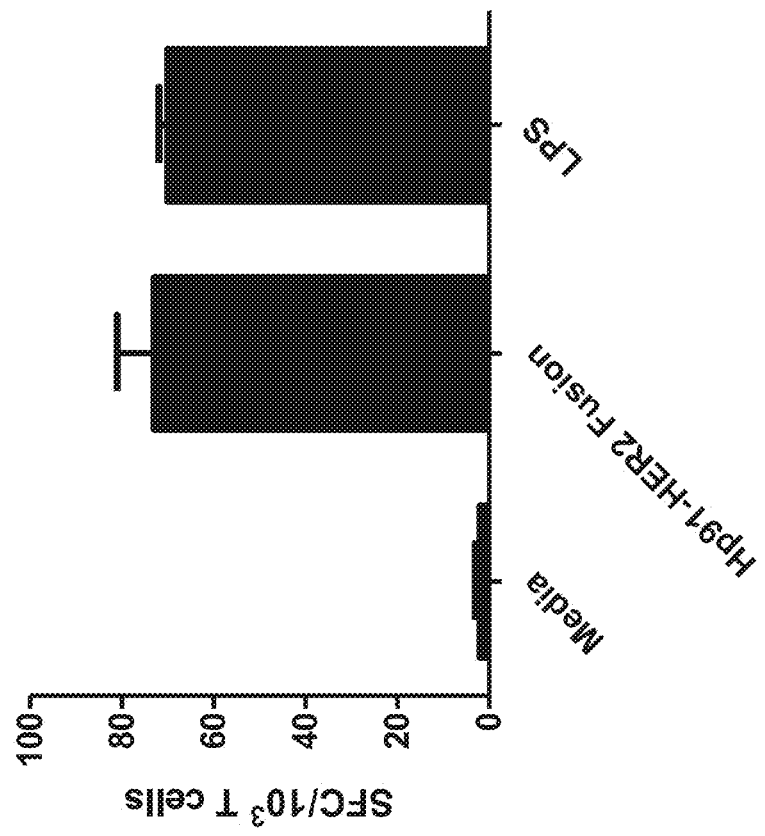
FIG. 7 shows a bar graph of Hp91 fused with antigen peptide HER2 increasing HER2-specific CTL responses in vitro. Immature bone-marrow derived mouse DCs were exposed to media, LPS, or HER2-HP91 fusion peptide for 48 h. DCs were co-cultured with HER2-specific CTLs overnight and the number of IFN-g secreting T cells was evaluated by ELISPOT.
Figure 8:
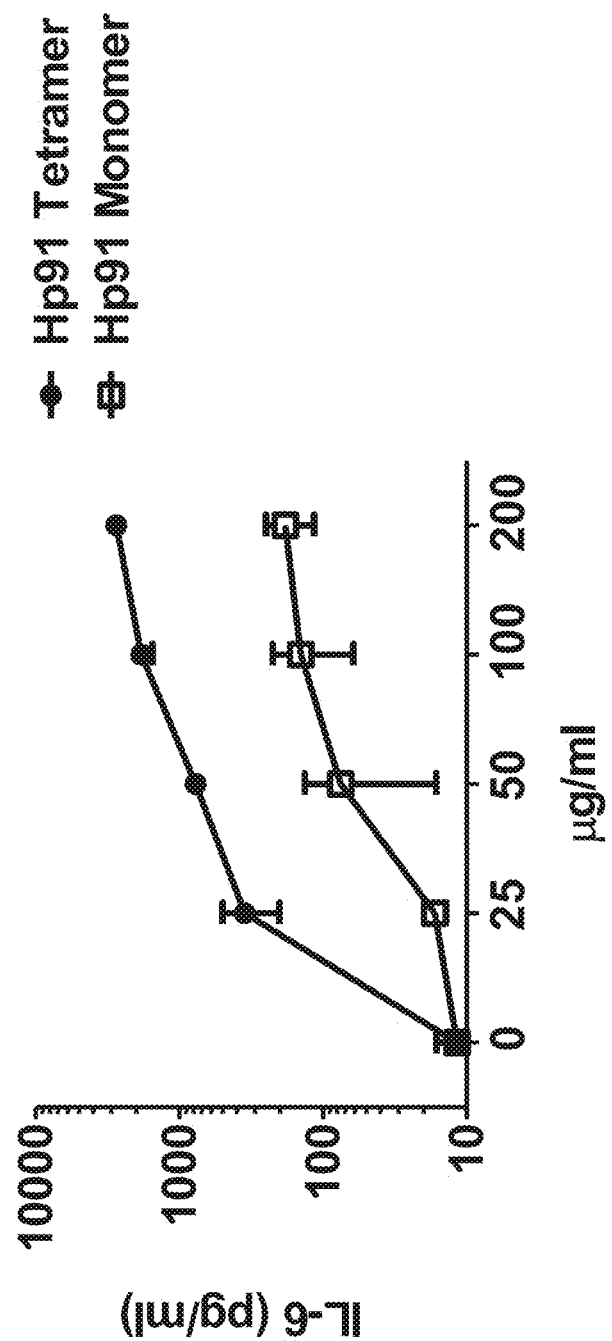
FIG. 8 shows a line graph of tetrameric Hp91 activating dendritic cells in vitro. Immature DCs were exposed to increasing concentrations of free Hp91 and matching amounts of Hp91 tetramer. Cell culture supernatants were collected after 48 h and analyzed for the presence of IL-6 by ELISA.
Figure 9:
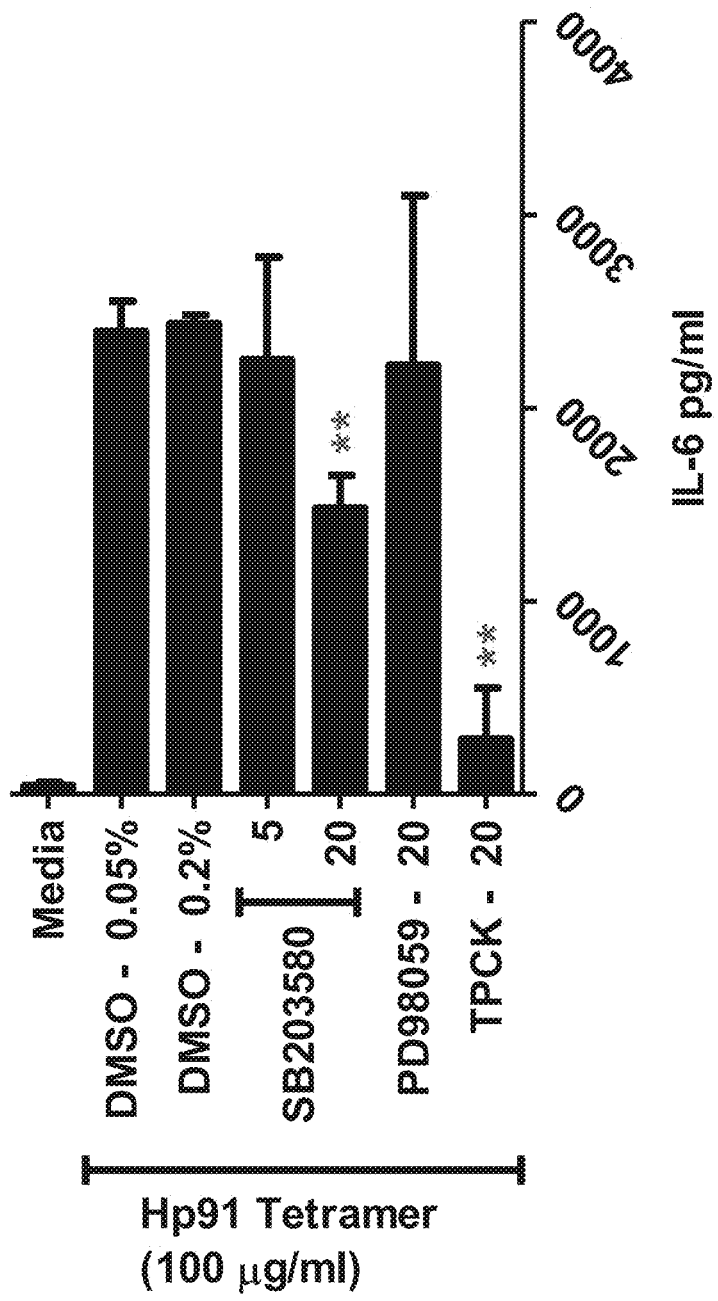
FIG. 9 shows a bar graph of tetrameric Hp91 activating dendritic cells in vitro through p38 and NF-kB. Immature DCs were pre-treated with the indicated inhibitors or DMSO control for 30 min prior to exposure to tetrameric Hp91. Cell culture supernatants were collected after 48 h and analyzed for the presence of IL-6 by ELISA.
Figure 10:
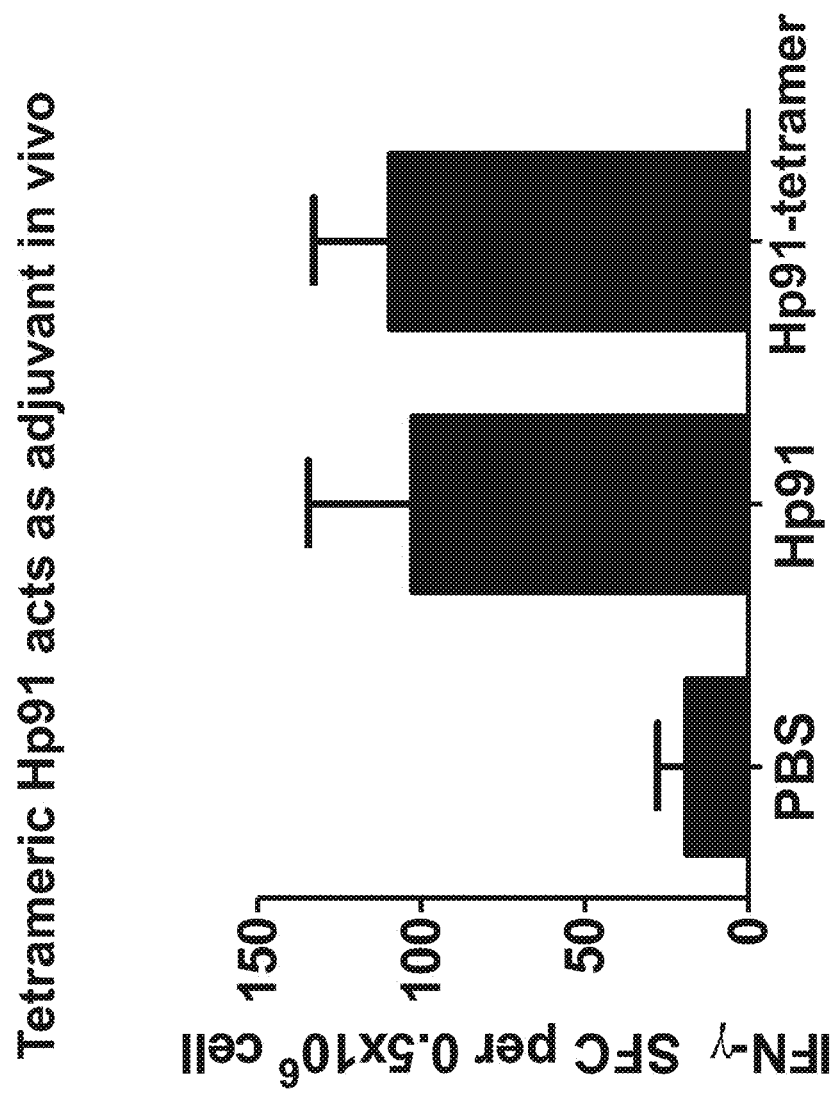
FIG. 10 shows a bar graph of tetrameric Hp91 acting as adjuvant in vivo. Mice were immunized with OVA peptide mixed with PBS, monomeric Hp91 (250 μg), or matching molarity of Hp91 tetramer and boosted two more times. After the final boost, mice were sacrificed and analyzed for OVA-specific CTL responses by ELISPOT.
Figure 11:
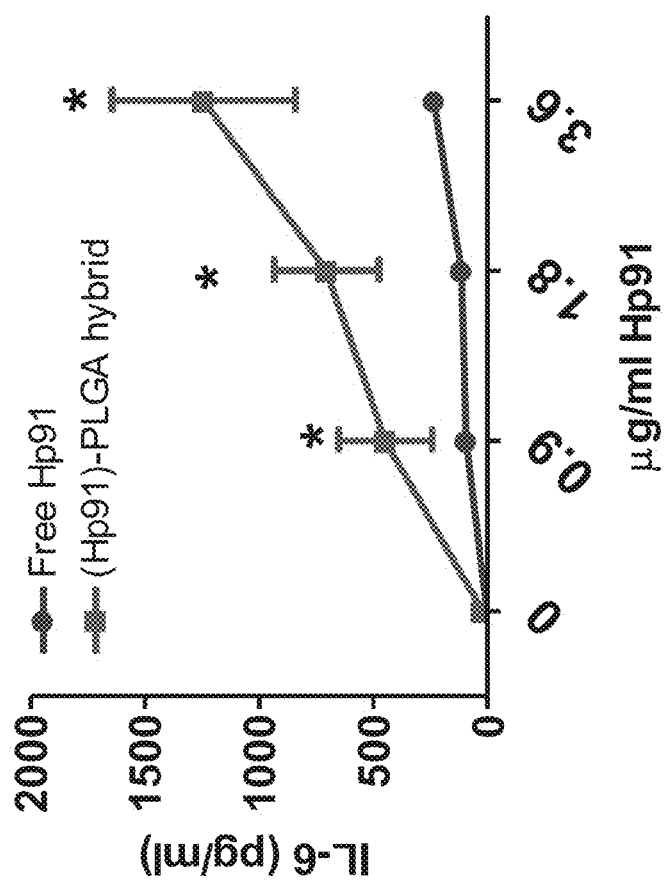
FIG. 11 shows a line graph of delivery of Hp91 inside of PLGA nanoparticles that leads to increased DC activation in vitro as compared to free Hp91. Immature human DCs were exposed to increasing concentrations of free Hp91 and matching amounts of Hp91 loaded in hybrid PLGA-nanoparticles. Cell culture supernatants were collected after 48 h and analyzed for the presence of IL-6 by ELISA.
Figure 12:
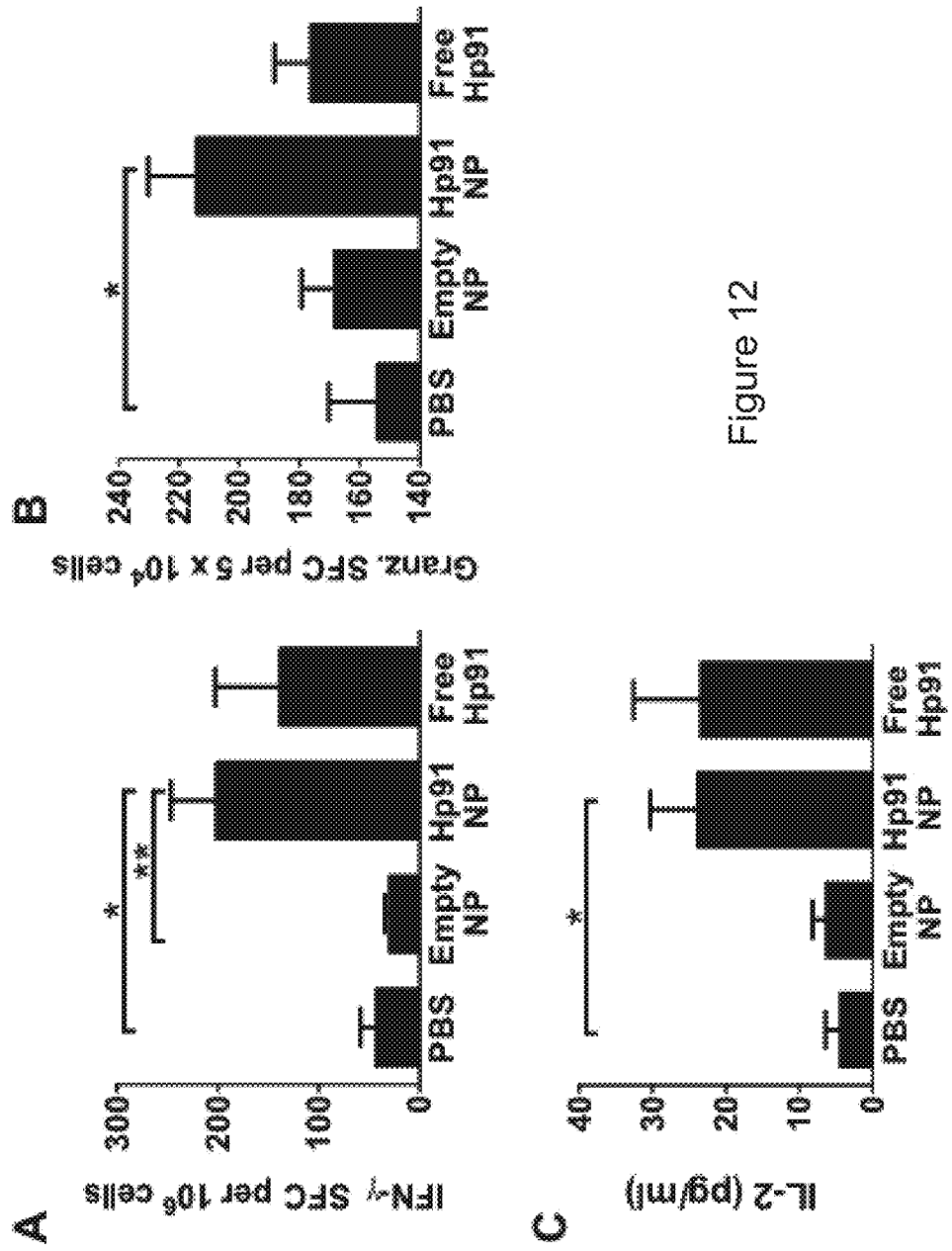
FIG. 12. Mice were immunized with OVA peptide mixed with PBS, empty nanoparticles, free Hp91, or matching amounts of Hp91 loaded in hybrid PLGA-nanoparticles and boosted two more times. After the final boost, mice were sacrificed and analyzed for OVA-specific CTL responses by ELISPOT. (A) Interferon-gamma ELISPOT (B) GranzymeB ELISPOT (C) IL-2 secretion from splenocytes. *p<0.05; Student's t-test.
Figure 13:
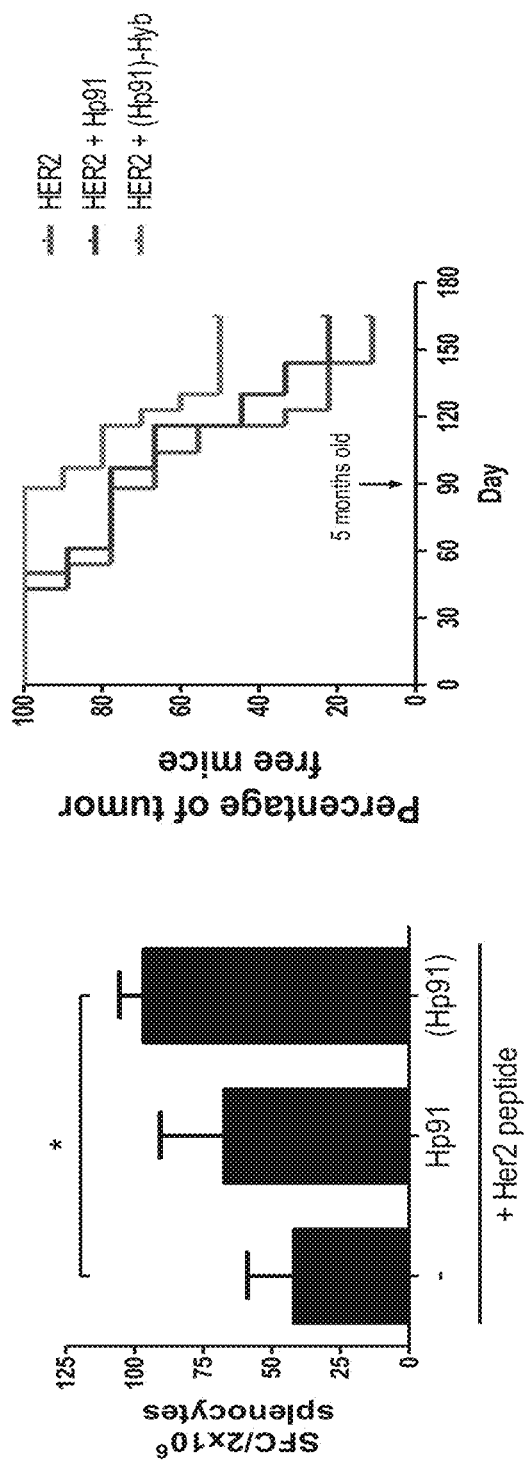
FIG. 13 shows a bar graph and a line graph of Hp91 inducing HER2-specific immune responses in HER2 transgenic mice and increasing the percentage of tumor free mice. Left: HER2neu transgenic mice (n=5) were immunized with HER2 alone or mixed with free Hp91 peptide or Hp91 loaded inside of PLGA-nanoparticles (Hp91) s.c.. Mice were boosted twice with the same vaccines. Mice were sacrificed after final boost and immune responses to HER2 were measured by ELISPOT. Right Mice (n=9-10) were monitored after immunization for tumor growth, the percentage of tumor free mice is depicted over time.
Figure 14:
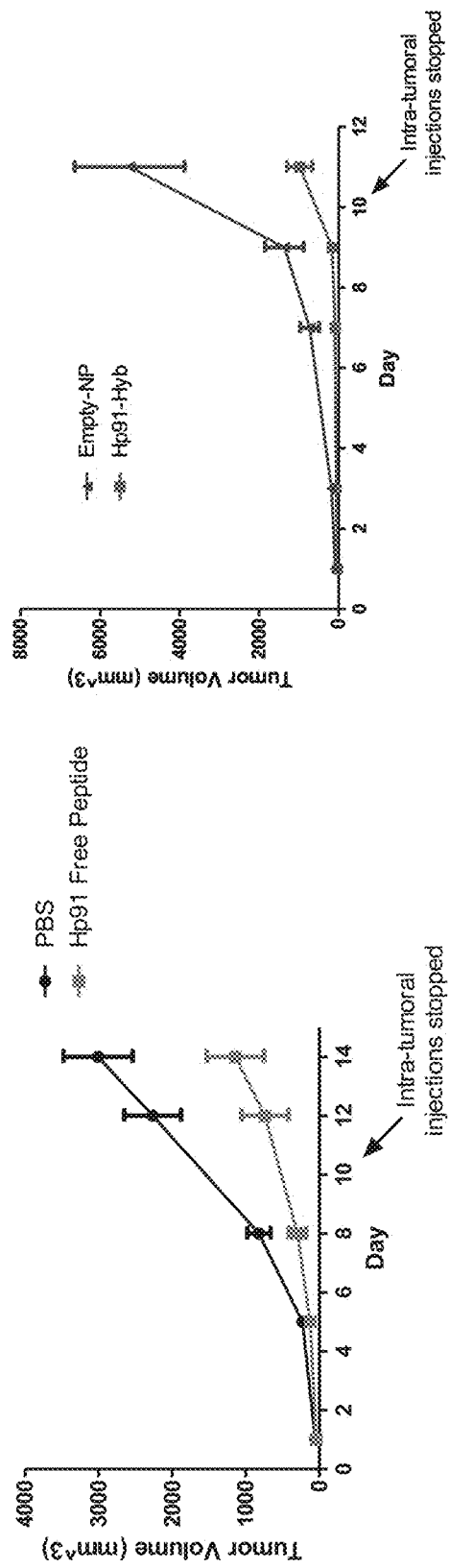
FIG. 14 slows line graphs of infra-tumoral injection of Hp91 peptide free and in nattoparticies leading to tumor (melanoma) growth retardation in vivo. Left: Tumor bearing mice (B16 tumors) received intra tumoral injections of free HP91 (100 μg) or PBS control. Right: Tumor bearing mice (B16 tumors) received intra tumoral injections of Hp91 loaded in PLGA-nanoparticles or matching amounts of empty nartoparticles aas control. In both cases the agents were injected daily for 10 days and tumor growth was monitored with a set of calipers over the indicated time period.
Figure 15:
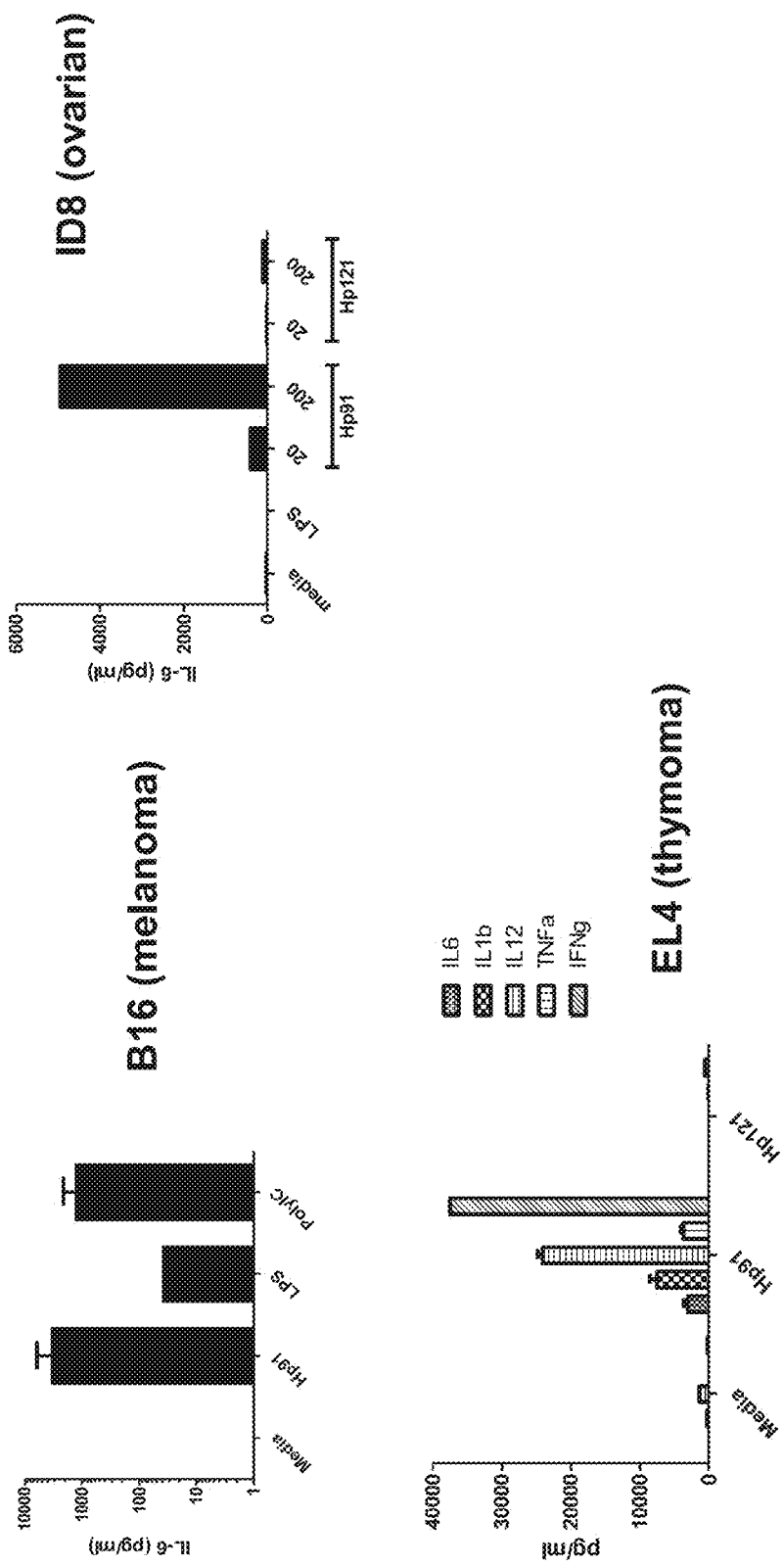
FIG. 15 shows bar grraphs of Hp91 causing cytokine release from tumor cells. Cell lines were exposed to media control, Hp91 (100 μg/ml), control peptide Hp121 (100 μg/ml), LPS (10 ng/ml), or poly I:C for 1 h, washed and cell culture supernatants were collected after 24 h and analyzed for the indicated cytokines by ELISA.
Figure 16:
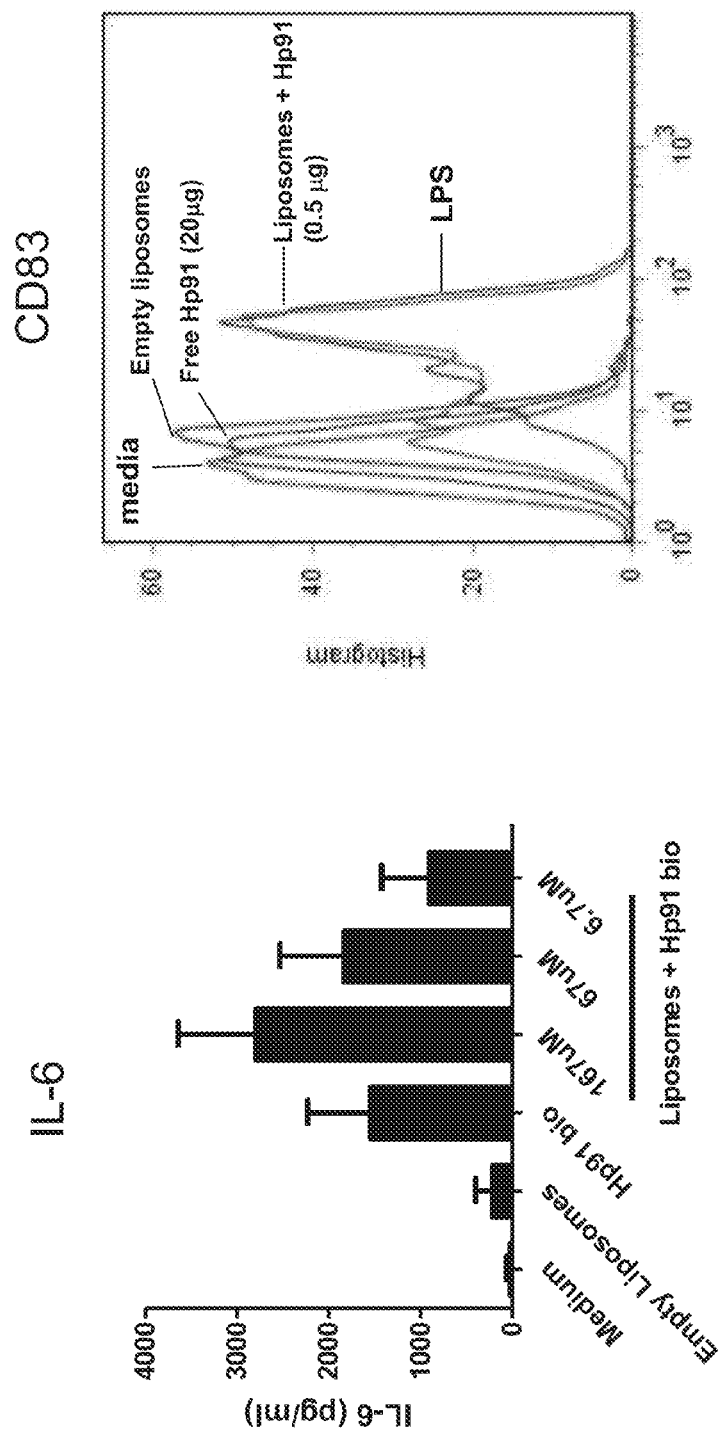
FIG. 16 shows a bar graph and a line graph of HP-91 packaged into liposome nanoparticles activates DCs more potently than free Hp91. Left: Immature human DCs were exposed to media, empty liposomes, free Hp91 (100 μg/ml), or different amounts of Hp91 loaded into liposomes for 48 h. Cell culture supernatants were analyzed for the presence of IL-6 by ELISA. Right: Immature human DCs were exposed to media, empty liposomes, free Hp91 (20 μg), 0.5 μg Hp91 loaded into liposomes, or LPS for 48 h. Cells were collected and analyzed for CD83 expression by flow cytometry.

To further investigate whether OVA-specific cytotoxic T lymphocytes (CTL) responses were induced by immunization with the ISP Hp91, splenocytes from immunized mice were assessed for their ability to lyse OVA-expressing E.G7-OVA cells. The strongest killing was observed using effector splenocytes from mice immunized with Hp91/OVA peptides (FIG. 5), which was even higher than of splenocytes from IFA/OVA peptide immunized mice. When data were analyzed by linear regression and slopes were compared, the percent killing of ttgget cells by effectors cells from mice immunized with Hp91/OVA peptides was significantly higher than the PBS control group.

Discussion

Although subunit vaccines promise to be less toxic, many are poorly immunogenic when administered without adjuvant. Alum, though FDA-approved, generates a weak Th1 response with a questionable safety profile. Thus, there is a great need for safer and more potent adjuvants [1-3].

We have previouSly shown that the 18 amino acid long ISP Hp91, is a stimulus for human DCs with the ability to generate a Th1-type immune response in vitro [25]. Here we demonstrate that Hp91 acts as adjuvant in vivo; inducing cellular immune responses to peptide and both cellular and humoral immune responses to protein antigen. The CD8 immune response was strong, since no in vitro expansion of splenocytes was needed to obtain a significant response as is commonly performed when testing vaccine responses. We show that the ISP Hp91 acts as an immune adjuvant to induce antigen-specific CD8 T cell responses in vivo. In addition, the immunostimulatory effects of Hp91 are related to its sequence, as the HMGB1 control peptide, Hp121, while matching Hp91 in length, isoelectric point, and charge, fulled to induce cellular immune response.

The cytokine profile induced by an immune adjuvant plays an important role in the polarization of the immune response. The data show that co-immunization with the ISP Hp91 and OVA peptides as well as OVA protein results in OVA-specific secretion of IL-2, suggesting that immunized mice are able to mount an adaptive immune response that activates T cells to synthesize and secrete IL-2 for in vivo proliferation of OVA-specific effector T cells. Interestingly, IL-4 levels were undetectable. Intravenous administration of Hp91 resulted in increased secretion of the Th1 cytokines IFN-γ and IL-12 (p70) associated with cell-mediated immunity. This together with the measured IFN-γ secretion by the T cells along with undetectable IL-4 suggests that Hp91 induces a Th1-type of immune response in vivo. We also show that immunization with Hp91/OVA peptide elicited stronger CTL responses than IFA/OVA.

We show that immunization using OVA protein mixed with Hp91 also induced humoral immune responses. This is very promising for future development of this novel adjuvant, as it could be used for prophylactic vaccination against infectious disease.

The ability of Hp91 to induce antigen-specific cell mediated, Th1 immure response may make Hp91 suitable as an adjuvant in cancer immunotherapies as well as vaccines against infectious diseases caused by intracellular bacteria [4] or viruses [42,43]. Some of the adjuvants that are being evaluated in clinical and preclinical settings like CD40L [44] and poly(I:C) synthetic double stranded RNA [45], act on myeloid DCs and have shown promising results for tumour immunotherapy [46], emphasizing the importance of activating myeloid DCs. As a peptide adjuvant that acts directly on myeloid DCs [25], the peptides of the invention have several advantages. They can be made synthetically, are inexpensive, can he produced in high quantities at GMP quality, and they can also be genetically engineered to DC targeting molecules like DEC-205 which promotes strong immune responses when linked to a DC stimulatory molecule [47,48]. Since the tested doses of Hp91 have shown no adverse effects in mice to date, this current data suggest peptide should be well-tolerated for use in vaccines.

References for Example 1 and Background of the Invention

1 Singh, M. & O_Hagan, D. Advances in vaccine adjuvants. *Nature Biotechnology* 1999, 17(11), 1075-1081.

2 McCluskie, M. J. & Weeratna, R. D. Novel adjuvant systems. 2001, 1(3), 263-271.

3 Singh, M. & O'Hagan, D. T. Recent advances in vaccine adjuvants. *Pharm Res* 2002, 19(6), 715-728.

4 Kovarik, J. & Siegrist, C. A. The search for novel adjuvants for early life vaccinations: can "danger" motifs show us the way? 2001, 49(3), 209-215.

5 Chisari, F. V. & Ferrari, C. Hepatitis B virus immunopathogenesis. *Annual Review of Immunology* 1995, 13, 29-60.

6 Dredge, K., Manion, J. B., Todryk, S. M. & Dalgleish, A. G. Adjuvants and the promotion of Th1-type cytokines in tumour immunotherapy. *Cancer Immunology, Immunotherapy* 2002, 51(10), 521-531.

7 Xu-Arnano, J., Kiyono, H., Jackson, R. J. et al. Helper T cell subsets for immunoglobulin A responses: oral immunization with tetanus toxoid and cholera toxin as adjuvant selectively induces Th2 cells in mucosa associated tissues. *J Exp Med* 1993, 178(4), 1309-1320.

8 Engers, H., Kieny, M. P., Malhotra, P. & Pink, J. R. Third Meeting on novel adjuvants curently in or close to clinical testing world health organization-Organization mondiale de la sante, Fondation Merieux, Annecy France, 7-9 Jan. 2002. *Vaccine* 2003, 21, 3503-3524.

9 De Gregorio, E., Tritto, E. & Rappuoli, R. Alum adjtrstanticity: unraveling a century old mystery. *European Journal of Immunology* 2008, 38(8), 2068-2071.

10 Gupta, R. K. Aluminum compounds as vaccine adjuvants. *Adv Drug Deliv Rev* 1998, 32(3), 155-172.

11 Audibert, F. M. & Lise, L. D. Adjuvants: current status, clinical perspectives and future prospects. *Immunol Today* 1993, 14(6), 281-284.

12 Gupta, R. K. & Siber, G. R. Adjuvants for human vaccines-current status, problems and future prospects. *Vaccine* 1995, 13(14), 1263-1276.

13 Romford, R. Will adjuvants be needed for vaccines of the future? *Dev Biol Stand* 1998, 92, 13-17.

14 Brewer, J. M., Conacher, M., Satoskar, A., Bluethmann, H. & Alexander, J. In interleukin-4-deficient mice, alum not only generates T helper 1 responses equivalent to freund's complete adjuvant, but continues to induce T helper 2 cytokine production. *European Journal of Immunology* 1996, 26(9), 2062-2066.

15 Krieg, A. M. CpG motifs in bacterial DNA and their immune effects. *Annu Rev Immunol* 2002, 20, 709-760.

16 Alexopoulou, L., Holt, A. C., Medzhitov, R. & Flavell, R. A. Recognition of double-stranded RNA and activation of NF-kappaB by Toll- like receptor 3. *Nature* 2001, 413 (6857), 732-738.

17 Netea, M. G., van der Graaf, C., Van der Meer, J. W. & Kullberg, B. J. Toll-like receptors and the host defense against microbial pathogens: bringing specificity to the innate-immune system. *Journal of Leukocyte Biology* 2004, 75(5), 749-755.

18 Takeda, K., Kaisho, T. & Akira, S. Toll-like receptors. *Annual Review of Immunology* 2003, 21, 335-376.

19 Petrovsky, N. & Aguilar, J. C. Vaccine adjuvants: current state and future trends. *Immunology and Cell Biology* 2004, 82(5), 488-496.

20 Weiner, G. J., Liu, H. M., Wooldridge, J. E., Dahle, C. E. & Krieg, A. M. Immunostimulatory oligodeoxynucleotides containing the CpG motif are effective as immune adjuvants in tumor antigen immunization. *Proc Natl Acad Sci U S A* 1997, 94(20), 10833-10837.

21 Chu, R. S., Targoni, O. S., Krieg, A. M., Lehmann, P. V. & Harding, C. V. CpG oligodeoxynucleotides act as adjuvants that switch on T helper 1 (Th1) immunity. *Journal of Experimental Medicine* 1997, 186(10), 1623-1631.

22 Krug, A., Towarowski, A., Britsch, S. et al. Toll-like receptor expression reveals CpG DNA as a unique microbial stimulus for plasmacytoid dendritic cells which syrtergizes with CD40 ligand to induce high amounts of IL-12. *European Journal of Immunology* 2001, 31(10), 3026-3037.

23 Krieg, A. M. Therapeutic potential of Toll-like receptor 9 activation. *Nat Rev Drug Discov* 2006, 5(6), 471-484.

24 Schmidt, C. Clinical setbacks for toll-like receptor 9 agonists in cancer. *Nature Biotechnology* 2007, 25(8), 825-826.

25 Telusma, G., Datta, S., Mihajlov, I. et al. Dendritic cell activating peptides induce distinct cytokine profiles. *Int Immunol* 2006, 18(11), 1563-1573.

26 Bianchi, M. E. DAMPs, PAMPs and alarmins: all we need to know about danger. *Journal of Leakocyte Biology* 2007, 81(1), 1-5.

27 Scaffidi, P., Misteli, T. & Bianchi, M. E. Release of chromatin protein HMGB1 by necrotic cells triggers inflammation. *Nature* 2002, 418(6894), 191-195.

28 Ulloa, L. & Messmer, D. High-mobility group box 1 (HMGB1) protein: friend and foe. *Cytokine Growth Factor Rev* 2006, 17(3), 189-201.

29 Wang, H., Vishnubhakat, J. M., Bloom, O et al. Proinflammatory cytokines (tumor necrosis factor and interleukin 1) stimulate release of high mobility group protein-1 by pituicytes. *Surgery* 1999, 126(2), 389-392.

30 Siegal, F. P., Kadowaki, N., Shodell, M. et al. The nature of the principal type 1 interferon-producing cells in human blood. *Science* 1999, 284(5421), 1835-1837.

31 Dumitriu, I. E. Baruah, P., Bianchi, M. E., Manfredi, A. A. & Rovere-Querini, P. Requirement of HMGB1 and RAGE for the maturation of human plasmacytoid dendritic cells. *Eur J Immunol* 2005, 35(7), 2184-2190.

32 Messmer, D., Yang, H., Telusma, G. et al. High mobility group box protein 1: an endogenous signal for dendritic cell maturation and Th1 polarization. *J Immunol* 2004, 173(1), 307-313.

33 Rovere-Querini, P., Capobianco, A., Scaffidi, P. et al. HMGB1 is an endogenous immune adjuvant released by necrotic cells. *EMBO Rep* 2004, 5(8), 825-830.

34 Park, J. S., Svetkauskaitc, D., He, Q, et al. Involvement of toll-like receptors 2 and 4 in cellular activation by high mobility group box 1 protein. *J Biol Chem* 2004, 279(9), 7370-7377.

35 Park, J. S., Gamboni-Robertson, F., He, Q. et 01. High mobility group box 1 protein interacts with multiple Toll-like receptors. *Am J Physiol Cell Physiol* 2006, 290(3), C917-924.

36 Tsung, A., Klune, J. R., Zhang, X. et at. HMGB1 release induced by liver ischemia involves Toll-like receptor 4 dependent reactive oxygen species production and calcium-mediated signaling. *J. Exp Med* 2007, 204(12), 2913-2923.

37 Yu, M., Wang, H., Ding, A. at al. HMGB1 signals through toll-like receptor (TLR) 4 and TLR2. *Shock* 2006, 26(2), 174-179.

38 van Zoelen, M. A., Yang, H., Florquin, S. et al. Role of Toll-Like Receptors 2 and 4, and the Receptor for Advanced Glycation End Products (Rage) in Hmgb1 Induced Inflammation in Vivo. *Shock* 2008.

39 Dumitriu, I. E., Baruah, P., Valentinis, B. et al. Release of High Mobility Group Box 1 by Dendritic Cells Controls T Cell Activation via the Receptor for Advanced Glycation End Products. *J Immunol* 2005, 174(12), 7506-7515.

40 Huttunen, H. J., Kuja_Panula, J. & Rauvala, H. Receptor for advanced glycation end products (RAGE) signaling induces CREB-dependent chromogranin expression during neuronal differentiation. *The Journal of Biological Chemistry* 2002, 277(41), 38635-38646.

41 Clawson, C., Huang, C. T., Futalan, D. et al. Delivery of a peptide via poly(d,1-lactic-co-glycolic) acid nanoparticles enhances its dendritic cell-stimulatory capacity. *Nanomedicine* 2010.

42 Brazolot Millan, C. L., Weeratna, R., Krieg, A. M., Siegrist, C. A. & Davis, H. L. CpG DNA can induce strong Th1 humoral and cell-mediated immune responses against hepatitis B surface antigen in young mice. *Proc Natl Acad Sci U S A* 1998, 95(26), 15553-15558.

43 Wong, B. R., Josien, R., Lee, S. Y. at al. TRANCE (tumor necrosis factor [TNF]-related activation-induced cytokine), a new TNF family member predominantly expressed in T cells, is a dendritic cell-specific survival factor. *J Exp Med* 1997, 186(12), 2075-2080.

44 Loskog, A. & Totterman, T. H. CD40L—molecule for tumor therapy. *Endocr Metab Immune Disord Drug Targets* 2007, 7(1), 23-28.

45 Kadowaki, N., Ho, S., Antonenko, S. et al. Subsets of human dendritic cell precursors express different toll-like receptors and respond to different microbial antigens. *J Exp Med* 2001, 194(6), 863-869.

46 Jasani, B., Navabi, H. & Adams, M. Ampligen: A potential toll-like 3 receptor adjuvant for immunotherapy of cancer. *Vaccine* 2009.

47 Gurer, C., Strowig, T., Brilot, F. et al. Targeting the nuclear antigen 1 of Epstein-Barr virus to the human endocytic receptor DEC-205 stimulates protective T-cell responses. *Blood* 2008, 112(4), 12314 239.

48 Trumpfheller, C., Caskey, M., Nchinda, G. et al. The microbial mimic poly IC induces durable and protective CD4+ T cell immunity together with a dendritic cell targeted vaccine. *Proc Natl Acad Sci U S A* 2008, 105(7), 2574-2579.

Example 2

Materials and Methods
Animals

C57BL/6 mice were purchased from Charles River Laboratories (Boston, Mass., USA). TLR4−/− and IL1R−/− mice were purchased from The Jackson Laboratories (Bar Harbor, Me., USA). IFN+βR−/− mice were purchased from B&K Universal (England, UK). MyD88−/− and TLR7−/− mice were a gift from S. Akira (Osaka University, Osaka, japan) and backcrossed for 10 generations onto the C57BL/6 background. Mice were bred and maintained at the Moores UCSD Cancer Center animal facility and all animal studies were approved by the Institutional Animal Care and Use Committee of UCSD and were performed in accordance with the institutional guidelines.

Reagents

Phenylarsine oxide and chlorpromazine (clathrin-mediated endocytosis inhibitors), sodium azide (energy-dependent endocytosis inhibitor), nystatin (caveolin-mediated endocytosis inhibitor), latrunculin B (phagocytosis inhibitor), amiloride (micropinocytosis inhibitor), and Dynasore (dynamin inhibitor) were purchased from Sigma-Aldrich (St. Louis, Mo.) as endocytosis inhibitors. The p38 MAPK-specific inhibitor, SB203580, and the NFκB inhibitor, N-tosyl-L-phenylalanine chloromethyl ketone (TPCK), were purchased from Sigma-Aldrich. The MEK1 inhibitor, PD98059, was purchased from Cell Signaling Technology (Danvers, Mass.). As many of these inhibitors required solubilization in DMSO, DMSO was used as a negative control.

Peptides

The peptides, including Hp91 (DPNAPKRPPSAF-FLECSE) (SEQ ID NO: 2), Hp121 (SIGDVAKKLGEM-WNNTAA) (SEQ ID NO: 47), scrambled Hp91 (ASLAP-PFPNCFDPKSREF) (SEQ ID NO: 48), and SIINFEKL (SEQ ID NO: 45) were all purchased from GenScript Corp (Piscataway, N.J., USA) and CPC Scientific (San Jose, Calif., USA). Peptides were synthesized with an N-terminal biotin or fluorescent tag (Cp488). Peptides were routinely synthesized with greater than 95% purity. Peptides were dissolved in RPMIE or PBS for in vitro and in viva experiments respectively.

Cell Lines

The J774 cell line was a gift from Maurizio Zanetti (UCSD) and was cultured in RPMI 1640 medium (Invitrogen, Carlsbad, Calif.), supplemented with 10 mmol HEPES (GIBCO-BRL Life Technologies, Grand Island, N.Y.), penicillin (100 U/mL)—streptomycin (100 μg/mL)—L-glutamine (2 mM) (GIBCO-BRL), and 10% (vol/vol) fetal calf serum (Omega Scientific, Tarzana, Calif.). The RAW 264.7 cell line was a gift from Dong-Er Zang (UCSD) and was cultured as above, except with 5% (vol/vol) fetal calf serum (Omega).

Generation of Human Monocyte-Derived DCs

Peripheral blood mononuclear cells were isolated from the blood of normal volunteers over a Ficoll-Hypaque (Amersham Biosciences, Uppsala, Sweden) density gradient. Anonymous blood was purchased from the San Diego Blood Bank; therefore, no institutional review hoard approvals were necessary. To generate DCs, peripheral blood mononuclear cells were allowed to adhere to culture plates for 1 hour. The nonadherent cells were washed off, and the adherent cells were cultured in RPMI 1640 medium (invitrigen) supplemented with 50 mmol 2-mercaptoethanol (Sigma), 10 mmol HEPES (GIBCO-BRL), penicillin (100 U mL$^{-1}$)-streptomycin (100 μg mL$^{-1}$)- L-glutamine (2 mM) (GIBCO-BRL), and 1% (volvol) human plasnia (Valley Biomedical, Whichester, Va.) supplemented with GM-CSF (1000 U mL$^{-1}$) (Bayer HealthCare Pharmaceuticals, Wayne, N.J.), and interleukin-4 (100 U mL$^{-1}$) (IL-4; R and D Systems, Minneapolis, Minn.) at days 0, 2, and 4. Immature human DCs (iDCs) were harvested on days 5-7.

Generation of Mouse Bone Marrow-Derived DO

Bone marrow-dedved DCs (BM-DCs) were prepared from C57BL/6 and knockout mice, as described by Inaba et al (36) with minor modifications. Briefly, single hone marrow cell suspensions were obtained from femurs and tibias and depleted of lymphocytes, granulocytes, and Ia+ cells by incubating with a mixture of monoclonal antibodies (mAbs; anti-CD4, anti-CD8, anti-B220/CD45R, and anti-Ia) (antibody hybridomas were a gift from Ralph Steinman (Rockefeller)) and low-toxicity rabbit complement (Pel Freez Biologicals, Rogers, Ark.) for 60 minutes at 37° C. Cells were resuspended at a concentration of $10^6$ cells mL$^{-1}$ in RPMI 1640 medium (invitrogen) supplemented with 10 mmol HEPES (GIBCO-BRL), penicillin (100 U/mL)—streptomycin (100 μg/mL)—L-glutamine (2 mM) (GIBCO-BRL), 5% (vol/vol) fetal calf serum (Omega), and 10 ng mL$^{-1}$ recombinant murine granulocyte-macrophage colony-stimulating factor (GM-CSF) (J558L GMCSF-secreting cells were a gift from Ralph Steinman). Fresh complete medium containing GM-CSF was added on days 2 and 4 of culture. Cells were collected for the experiments on days 5-7.

Confocal Microsocpy

Immature human DCs ($10^5$) were pre-cooled on ice and subsequently incubated for 30 minutes on ice in culture medium with biotinylated Hp91 or Hp121 to allow peptide binding. Cells were washed and then incubated for the indicated time at 37° C. Cells were cytospun (Shandon Cytospin 2 centrintge) onto glass slides, fixed, pernieabiized with acetone, and stained with Streptavidin-Alexa 488 (Invitrogen) to visualize biotinylated peptides and Hoechst 33258 DNA stain (Invitrogen). Cells were imaged on a Zeiss LSM confocal microscope.

Flow Cytometry

For most experiments, iDCs were pre-cooled on ice for 30 minutes. Cells were subsequently incubated for the indicated times and temperatures in culture medium with biotinylated peptides. Cells were washed, permeabilized with Cytofix/Cytoperm (BD Biosciences, Franklin Lakes, N.J.) stained with Streptavidin-Alexa 488 (Invitrogen), and analyzed by flow cytometry. For experiments with endocytosis inhibitors, cells were pre-treated for 30 minutes with the indicated inhibitors prior to incubation with the biotinylated peptides. For experiments with J774 macrophages, cells were pre-cooled on ice, pre-treated with 30 minutes with the indicated inhibitors, and subsequently incubated for 30 minutes with fluorescentlylabeled Hp91 (Cp488-Hp91). Cells were immediately analyzed by flow cytometry.

Stimulation of iDCs and BM-DCs

At days 5-7 of culture, iDCs were either left untreated or were stimulated with indicated doses of peptide, For inhibition experiments, immature human DCs were pre-treated with the indicated doses of SB20358, PD98059, N-tosyl-L-phenylalanine chloromethyl ketone (TPCK), or DMSO control for 30 minutes prior to stimulation. For experiments with human DCs, supernatants were analyzed by ELISA (eBioscience, Inc. San Diego, Calif.), according to the manufacturer's instructions, 48 h after stimulation. For experiments with mouse BM-DCs, supernatants were analyzed by ELISA (eBioscience), 24 h after stimulation.

Immunizations and Splenocyte Preparation

Mice were immunized s.c. with 50 μg of SIINFEKL peptide. The SIINFEKL peptide was co-administered with either PBS, Hp91 (250 μg), or scrambled Hp91 (250 μg). Peptides were dissolved in PBS for all immunizations, Mice were boosted two weeks later and spleens and blood were collected one week after the final immunization. Single cell suspensions of splenocytes were prepared by mechanical disruption and separation through a 70 mm nylon cell strainer (BD Biosciences). Red blood cells were lysed using ammonium chloride buffer (Roche Diagnostics, Indianapolis, Ind.) and the splenocytes were subsequently resuspended in RPMI 1640 medium (Invitrogen) supplemented with 10 mmol HEPES (GIBCO-BRL), penicillin (100 U/mL)—streptomycin (100 μg/mL)—glutamine (2 mM) (GIBCO-BRl.), arid 5% (vol/vol) fetal calf serum (Omega).

Enzyme-Linked Immunospot Assay

Freshly isolated splenocytes were plated in duplicate to wells of a nifrocellulose bottom enzymelinked immunospot (ELISPOT) plate (Millipore, NAillerica, Mass., USA) that had been previously coated overnight with 5 μg ml$^{-1}$ monoclonal anti-mouse IFN-γ antibody (Mabtech, Stockholm, Sweden). Splenocytes were cultured overnight at 37° C., with 2.5 μg ml$^{-1}$ SIINFEKL peptide, 5 μg ml$^{-1}$ concanavalin A positive control (Sigma), or left unstimulated (medium only). After 18 h, culture supernatants were collected for cytokine analysis and ELESPOT plates were developed using 1 μg ml$^{-1}$ biotinylated anti-mouse IFN-γ antibody (Mabtech), Streptavidin-HRP (Mabtech), and TMB Substrate (Mabtech). The plate was scanned and the spots were counted using an automated ELISpot Reader System (CTL ImmunoSpot, Shaker Heights, Ohio, USA).

Cytokine Release Assay

To measure cytokine release from immunized mice, splenocytes were cultured overnight with 2.5 μg ml$^{-1}$ SINFEKI: peptide, 5 μg ml$^{-1}$ concanavalin A positive control (Sigma), or left unstimulated (medium only). After 18 h, cell culture supernatants were collected and analyzed for the presence of IL-2 by ELISA. (eBioscience).

Immunoblotting

Mouse J774 or RAW 264.7 macrophages stimulated with Hp91 or FPS for 20, 40, or 60 minutes were lysed for 20 minutes on ice in RIPA lysis buffer (10 mM Tris pH 7.4, 1.50 mM NaCl, 1% TritoriX-100, 0.1% sodium deoxycholate, 0.1% sodium dodecylsulfate (SDS), 5 mM EDTA supplemented with 1 mM phenylmethylsulfonyl fluoride, Halt phosphatase inhibitor (Thermo Fisher Scientific), 1 mM sodium vanadate, 1 mM sodium fluoride, and complete protease inhibitor cocktail (Roche). Protein concentration was determined with the DC (Detergent Compatible) protein assay (Bio-Rad). The lysates were snap-frozen and stored at −80° C. Equal amounts of protein lysates were separated by gel electrophoresis with the use of a NuPAGE Novex 4%-12% Bis-Tris Midi Gel (Invitrogen) and transferred to polyvinylidene fluoride membranes (Bio-Rad). Membranes were washed with 1×TBST (Tris-Buffered Saline Tween-20) and blocked for 1 hour at room temperature in 5% milk/TBST. Membranes were probed overnight for phospho- p38, phospho (p)-interferon regulatory factor 3 (IRF3), p38, IRF3, glyceraldehyde-3-phosphate dehydrogenase (GAPDH), or β-actin (Cell Signaling Technology), The next day, membranes were washed with 1×TEST and incubated with goat anti-rabbit or anti-mouse horseradish peroxidase-conjugated secondary antibodies (Santa Cruz Biotechnology, Santa Cruz, Calif.) diluted in 5% milk/TBST for 1 hour at room temperature. Antibodies were detected with the use of either an enhanced chemiluminescence detection kit (GE Healthcare, Piscataway, N.J.) or SuperSignal West Femto Maximum Sensitivity Substrate (Thermo Fisher Scientific, Rockford, Ill.). In some experiments, cells were pre-treated with the endocytosis inhibitor Dynasore.

Statistical Analysis

Data represented are mean ±SEM. Data were analyzed for statistical significance using unpaired or paired Student's t-tests. Statistical analysis was done using GraphPad software version 5.01 for Windows (GraphPad Software, San Diego, Calif., USA). A p value <0.05 was considered statistically significant.

Results

Hp91 Enters Dendritic Cells Via Clathrin-Mediated Endocytosis

Figure 17:
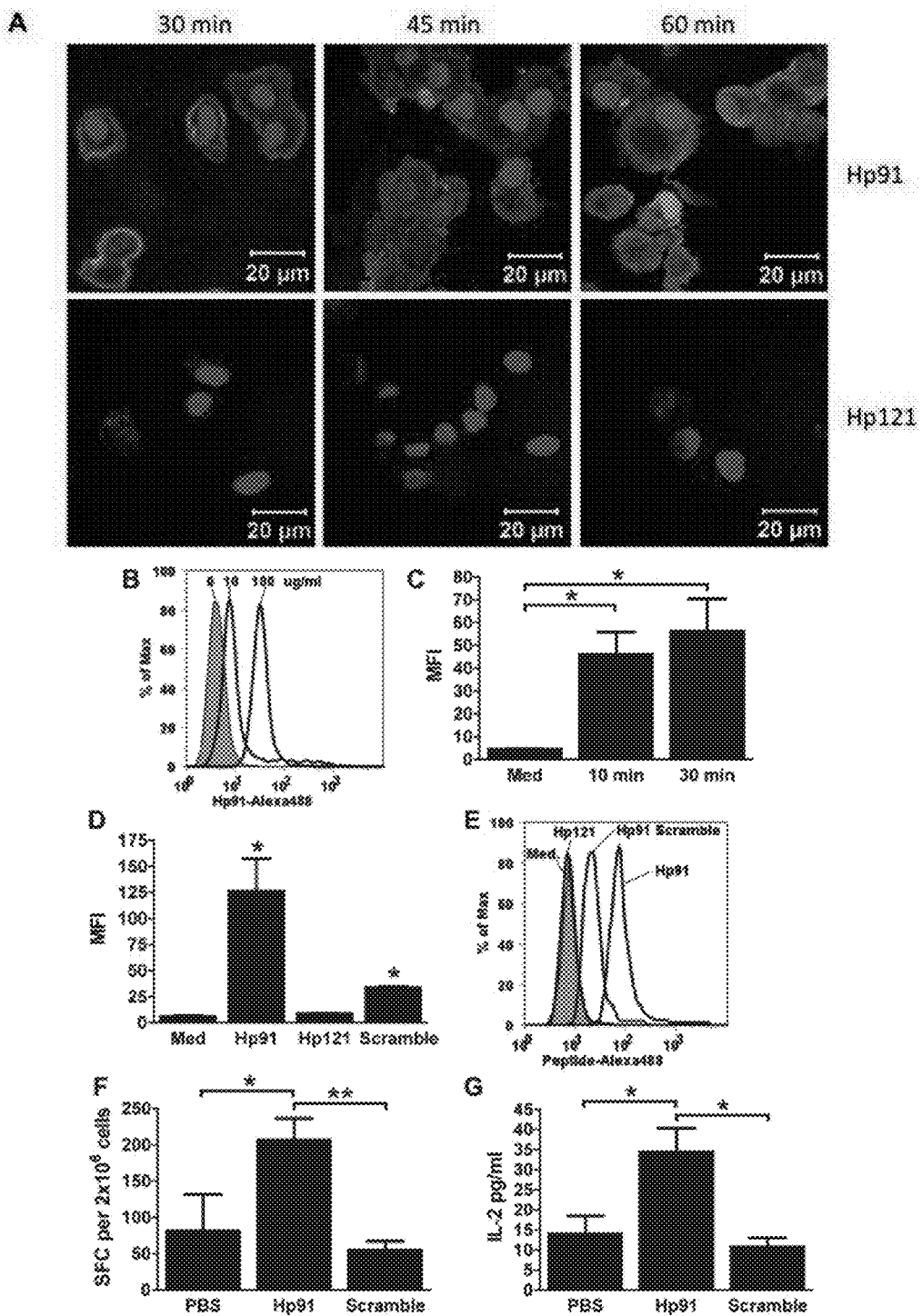
FIG. 17. Hp91 uptake by DCs is dose, time, and sequence dependent. (A) Immature human DCs (iDCs) were pre-cooled, incubated on ice for 30 minutes with biotinylated Hp91 or Hp121 (200 μg ml$^{-1}$) to allow peptide binding, washed, then incubated for 0, 15, or 30 additional minutes at 37° C. Times on figure represent total incubation times (ice and 37° C.). Cells were cytospun, fixed, permeabilized, and stained with Streptavidin-Alexa 488 to visualize biotinylated peptides (Green) and Hoechst DNA stain (Blue). Cells were imaged on a Zeiss LSM confocal microscope. Data are representative of 3 independent experiments. (B) iDCs were pre-cooled on ice for 30 minutes, then incubated with biotinylated-Hp91 (0, 10, or 100 μg ml$^{-1}$) for 30 minutes at 37° C. Cells were permeabilized with Cytofix/Cytoperm, stained with, and analyzed by flow cytometry. Results shown are representative of 6 independent experiments. (C) iDCs were incubated with biotinylated Hp91 for 10 or 30 minutes (at 100 μg ml$^{-1}$) and permeabilized, stained, and analyzed as above. Results shown are mean (±SEM) of 4 independent experiments. (D-E) iDCs were pre-cooled on ice for 30 minutes, then incubated with medium only or biotinylated-Hp91, Hp121, or scrambled Hp91 ("Scramble") at 200 μg ml$^{-1}$ for 30 minutes at 37° C. Cells were permeabilized, stained, and analyzed by flow cytometry as above. (D) is mean (±SEM) for 3 independent experiments and (E) is a representative result. *p<0.05 compared to medium; Student's t-test. (F-G) Mice were immunized with SIINFEKL peptide in PBS with Hp91 or Scramble. (F) Freshly isolated splenocytes from the immunized mice were cultured in the presence of SIINFEKL peptide (2.5 μg ml$^{-1}$). The number of IFN-γ-secreting cells was determined 18 h later. The data shown is mean (±SEM) for 5-10 mice/group. *p<0.05 between groups; Student's t-test. (G) Freshly isolated splenocytes from the immunized mice were cultured in the presence of STEN FEKL peptide (2.5 μg ml$^{-1}$). Supernatants were collected after 18 hours and analyzed for IL-2 secretion by ELISA. The data shown is mean (±SEM) for 5-10 mice/group. *p<0.05 between groups; Student's t-test.

To gain insight into the mechanism of action of the DC stimulatory peptide Hp91, we investigated its interaction with DCs. DCs were exposed to Hp91 or a control peptide, Hp121, which is also derived from HMGB-1 and has the same length, a similar charge and isoelectric point as Hp91. Confocal microscopy showed that Hp91 was detected within DCs within 5 minutes, while the control peptide Hp121 was not detected, even after 30 minutes at 37° C. (FIG. 17A). We observed a dose dependent uptake of Hp91 by flow cytometry (FIG. 17B), which appears to plateau between 10 and 30 minutes (FIG. 17C). Uptake of Hp91 is sequence specific, as the control peptide Hp121 was not taken up by DCs (FIG. 17D, 17E). Although a scrambled version of Hp91 was taken up by DCs, it was at a much lesser extent than Hp91 (FIG. 17D, 17E), and mice immunized with the scrambled Hp91 sequence failed to mount an antigen-specific immune response as compared to Hp91 (FIG. 17F, 17G).

Figure 18:
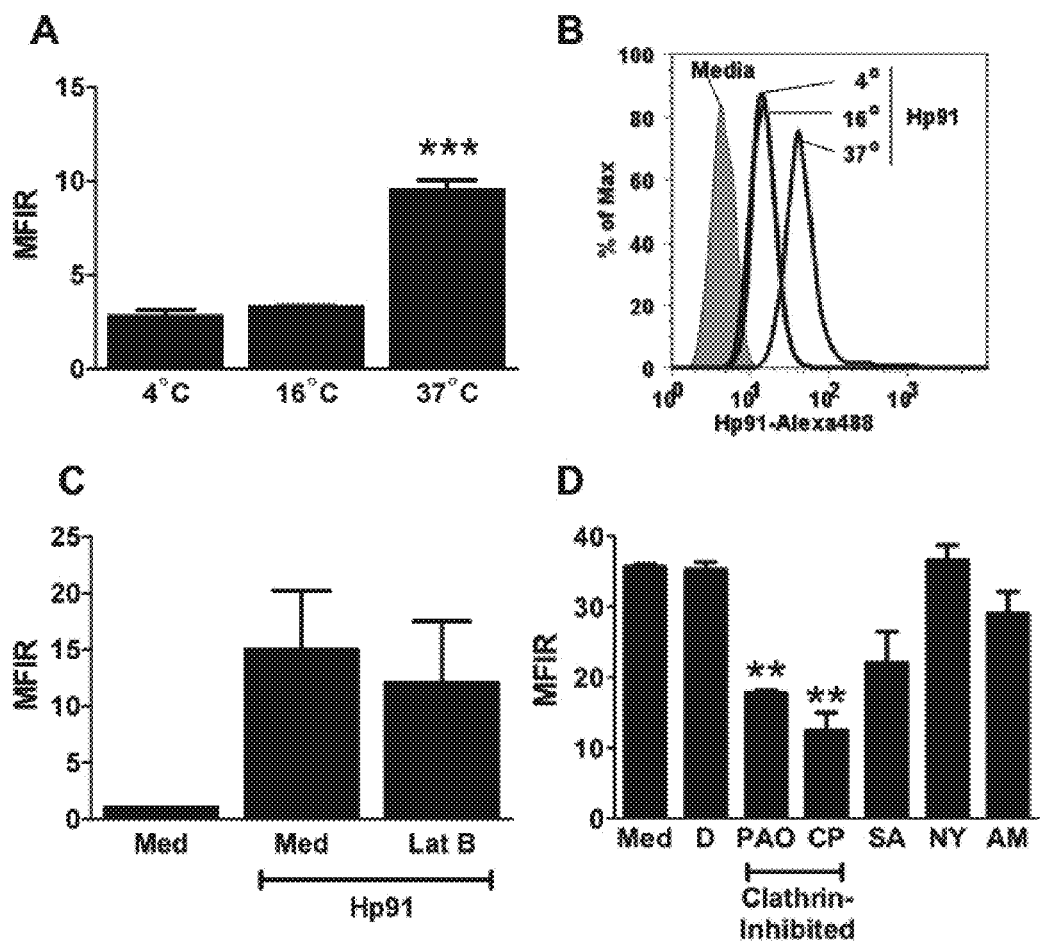
FIG. 18. Hp91 is taken up by ciathrin-mediated endocytosis. (A-B) immature human DCs were pre-cooled on ice for 30 minutes, then incubated with biotinylated Hp91 (200 μg ml$^{-1}$) for 30 minutes at 4, 16, or 37° C. Cells were permeabilized with Cytofix/Cytoperm, stained with Streptavidin-Alexa 488, and analyzed by flow cytometry. (A) Data are mean (±SEM) of 3 independent experiments and (B) is a representative result. *p<0.001 compared to 4° C.; Student's t-test. (C) iDCs were pre-treated with the phagocytosis inhibitor Latrunculin B or medium only for 30 minutes before incubation with biotinylated-Hp91 for 30 minutes. Cells were permeabilized, stained, and analyzed by flow cytometry as above. Data are mean (±SEM) of 5 independent experiments. (D) iDCs were pre-treated for 30 minutes with medium only (Med), DMSO control (D), the clathrin-mediated endocytosis inhibitors 1) phenylarsine oxide (PAO) at 2 μM or 2) chlorpromazine (CP) at 100 μM, the energy-dependent endocytosis inhibitor sodium azide (SA) at 10 mM, the caveolin-mediated endocytosis inhibitor nystatin (NY) at 20 μM, or the micropinocytosis inhibitor amitoride (AM) at 2 mM before incubation with biotinylated Hp91 (200 μg ml$^{-1}$) for 30 minutes. Cells were permeabilized, stained, and analyzed by flow cytometry as above. Results are mean (±SEM) of 3 independent experiments. p<0.01 compared to DMSO control; Student's t-test.

Cell penetrating peptides are preferentially taken up via endocytosis, at 37° C., or transcytosis (37), which occurs at 16° C. We tested the temperature at Which Hp91 was taken up by DCs to determine the method of uptake. DC uptake of Hp91 occurred at 37° C., but not 16° C., or 4° C. (FIG. 18A, 18B), suggesting that uptake occurs via an energy dependent process, such as endocytosis. Endocytosis pathways include phagocytosis, macropinocytosis, clathrin-mediated, or lipid-raft/caveolin-mediated. The mechanism of uptake was determined using specific inhibitors of these endocytosis pathways. Latrunculin B (LatB), a specific phagocytosis inhibitor, while completely abrogating uptake of Dextran FITC, did not significantly reduce uptake of Hp91 (FIG. 18C). Phenylarsine oxide and chlorpromazine, both clathrin-mediated endocytosis inhibitors, significantly reduced the uptake of Hp91, suggesting that uptake occurs via clathrin-mediated endocytosis (FIG. 18D). Sodium azide, which generally tests for energy-dependent endocytosis, inhibited Hp91 uptake by approximately 40% (FIG. 18D), though not significantly. When using a fluorescerttly labeled version of Hp91 (Cp488), sodium azide significantly inhibited Hp91 uptake. In contrast, the lipid-raft/caveolin-mediated endocytosis inhibitor, nystatin, and the macropinocytosis inhibitor, amiloride, failed to significantly reduce uptake of Hp91 (FIG. 18D), suggesting uptake is not via lipid rafts, nor macropinocytosis.

Hp91 Induces IL-6 Secretion in DCs Via p38 MAPK and NFκB

Figure 19:
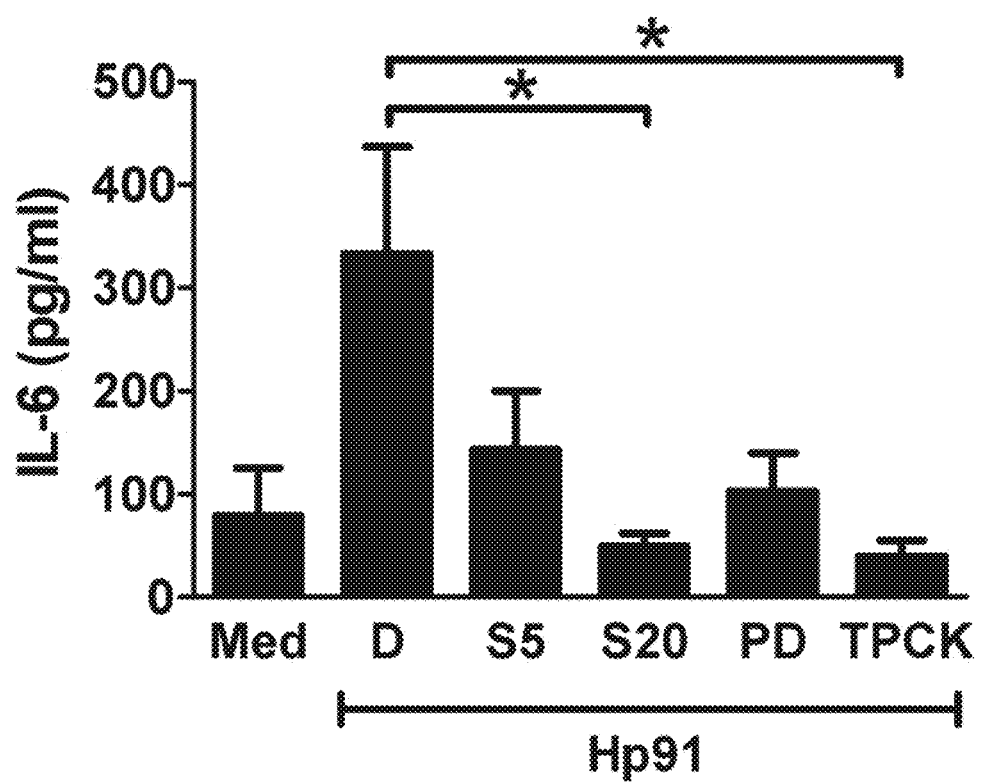
FIG. 19. p38 MAPK and NFkB are necessaryibr Hp91-mediated IL-6 secretion from human dendritic cells. Immature human DCs were pre-treated for 30 minutes with DMSO control (D), SB203580 at 5 (S5) or 20 (S20) μM, PD98059 (PD) at 20 μM, or NFkB at 20 μM prior to exposure to Hp91. Cell culture supernatants were collected after 48 h and analyzed for the presence of IL-6 by ELISA. Results are mean (±SEM) for 5 independent experiments, *p<0.05; Student's t-test.

We have previously shown that the p38 MAPK inhibitor, SB203580, down-regulated HMGB1 B box-induced secretion of IL-6 (38). Pretreatment of human DCs with SB203580, a p38 MAPK inhibitor, and N-p-Tosyl-L-phertylatanine chloromethyl ketone (TPCK), an NF-κB inhibitor, significantly reduced the Hp91-induced IL-6 secretion (FIG. 19). In contrast, PD98059, a MEK1 inhibitor, failed to significantly reduce IL-6 secretion (FIG. 19). These results suggest that Hp91 causes DC activation in a p38 and NF-κB dependent manner.

Hp91-Mediated Activation of DCs is Dependent on MyD88, TLR4, and IFNαβR

Figure 20:
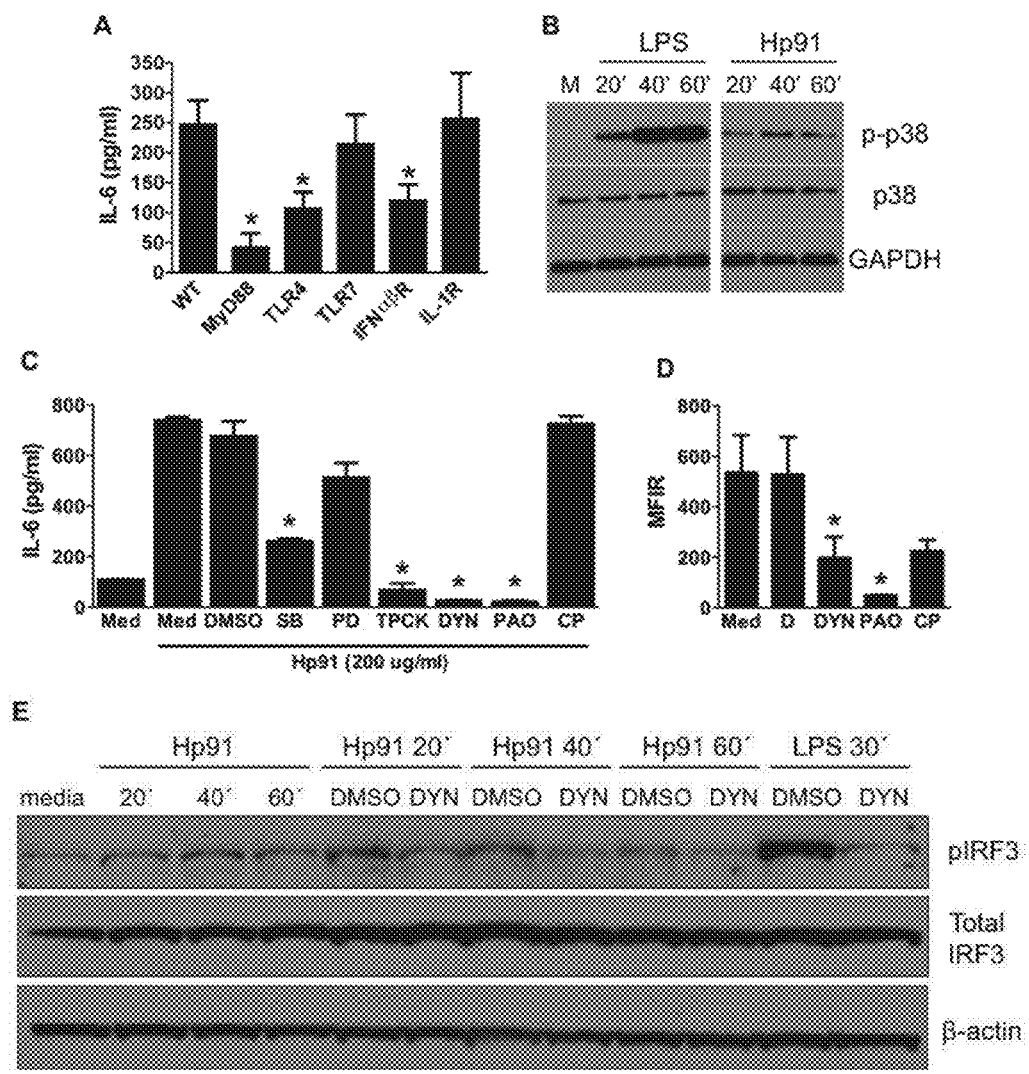
FIG. 20. TLR4. MyD88, and MyD88-dependent and -independent pathways are necessary for Hp91-mediated activation of mouse cells. (A) Immature BM-DCs from wild type (WT) or knockout mice (as indicated) were incubated with Hp91 (200 μg ml$^{-1}$). Supernatants were collected after 24 hours and analyzed for the presence of IL-6 by ELISA. Results are mean (±SEM) for at least 3 independent experiments. *p<0.05 compared to WT; Student's t-test. (B) J774 macrophages were stimulated for 20, 40, or 60 minutes with Hp91 (200 μg ml$^{-1}$) or LPS (10 ng ml$^{-1}$) or left unstimulated (M). Cells were harvested, lysed, and analyzed for p-p38. Immunoblots were probed with anti-p-38, total p38, and GAPDII antibodies. Data shown is representative from 4 separate immunoblots. Non-relevant wells were removed from the blot. (C) J774 macrophages were pre-treated for 30 minutes with DMSO control (D), SB203580 at 20 (SB) μM, PD98059 (PD) at 20 μM, TPCK at 20 μM, Dynasore (DYN) at 80 μM, phenylarsine oxide (PAO) at 2 μM, or chlorpromazine (CP) at 100 μM prior to exposure to Hp91. Cell culture supernatants were collected after 24 h and analyzed for the presence of IL-6 by ELISA. Data shown are mean (±SEM) for triplicates. SB, PD, and TPCK results are representative of 3 independent experiments. *p<0.05; Student's t-test. (D) J774 macrophages were pre-treated for 30 minutes with medium only (Med), DMSO control (D), the dynamin-mediated endocytosis inhibitor Dynasore (DYN) at 80 μM or the clathrin-mediated endocytosis inhibitors 1) phenylarsine oxide (PAO) at 2 μM or 2) chlorpromazine (CP) at 100 μM before incubation with Cp488-labeled Hp91 (200 μg ml$^{-1}$) for 30 minutes. Cells were washed and immediately analyzed by flow cytometry as above. Results are mean (±SEM) of 4 independent experiments. *p<0.05 compared to DMSO control; Student's t-test. (E) RAW 264.7 macrophages were pre-treated for 30 minutes with medium only, DMSO control (DMSO), or Dynasore (DYN) at 80 μM prior to stimulation for 20, 40, or 60 minutes with Hp91 (200 μg ml$^{-1}$) or LPS (10 ng ml$^{-1}$) or medium only (media). Cells were harvested, lysed, and analyzed for p-IRF3. Immunoblots were probed with anti-p-IRF3, total IRF3, and β-actin antibodies.

As clathrin-mediated endocytosis is receptor-mediated, we set out to identify the receptor(s) for Hp91. Several receptors have been implicated in mediating the responses to the parent molecule HMGB1, including TLR4 (19-22, 24, 26). To identify the receptor(s) involved in activation of DCs, mouse BM-DCs were generated from wildtype and knockout mice and cells were exposed to Hp91. IL-6 secretion was strongly and significantly reduced in BM-DCs from MyD48 and TLR4 knockout mice (KO) (FIG. 20A), whereas IL-6 production from BM-DCs generated from TLR7 KO mice was comparable to wild type (FIG. 20A). In addition, IL-6 secretion in IFNαβR knockout. mice was significantly reduced (FIG. 20A). No change was observed in IL-6 secretion from IL-1R knockout mice.

Involvement of TLR4 and MyD88 and their downstream pathways was further confirmed by immunoblotting for phospho-p38. Phospho-p38 (p-p38) was upregulated after 40-60 minutes of Hp91 stimulation (FIG. 20B) in 4 independent experiments. In some, but not all experiments, upregulation of p-p38 was observed as early as 20 minutes after Hp91 stimulation.

Hp91-Mediated Activation of DCs Clathrin- and Dynamin-Dependent

In LPS signaling of macrophages, TLR4 is endocytosed in a drumlin-dependent manner for downstream signaling (39), so we tested if pre-treatment of macrophages with clathrin- and dynamin- mediated endocytosis inhibitors would reduce Hp91-mediated IL-6 secretion. Similar to with LPS, pretreatment with the dynamin-dependent endocytosis inhibitor, Dynasore, significantly reduced Hp91-induced IL-6 secretion (FIG. 20C). In addition, a significant reduction in IL-6 was observed of blocking clathrin-mediated endocytosis with phenylarsine oxide (FIG. 20C). Interestingly, no reduction in IL-6 was observed after pre-treatment with chlorpromazine. As we had observed a reduction in Hp91-mediated IL-6 secretion in human DCs following pretreatment with the p38 and NF-κB inhibitors, SB203580 and TPCK, in human DCs, we tested if a similar reduction in IL-6 would be observed in mouse cells. As was seen in human cells, SB203580 and TPCK significantly lowered than the amount of Hp91-stimulated IL-6 secreted from mouse macrophages (FIG. 20C), farther confirming the involvement of p38 and NF-κB in Hp91 signaling. Furthermore, we demonstrated that the dynamin-dependent endocytosis inhibitor, Dynasore, significantly inhibited uptake of Hp91 (FIG. 20D).

As a decrease in Hp91-induced IL-6 secretion was observed in IFNαβR knockout BM-DCs (FIG. 20A), we set out to investigate if the MyD88-independent, TRAM/TRIF signaling pathway was activated by probing for phosphorylation of the downstream interferon regulatory factor 3 (IRF3) transcription factor. Phospho-IRF3 (pIRF3) was upregulated after Hp91 stimulation (FIG. 20E). In addition, blocking endocytosis with Dynasore reduced the phosphorylation of IRF3, suggesting that Hp91 uptake is required for MyD88-independent interferon regulatory factor 3 signaling.

A Proposed Mechanism of Hp91 Signaling

Figure 21:
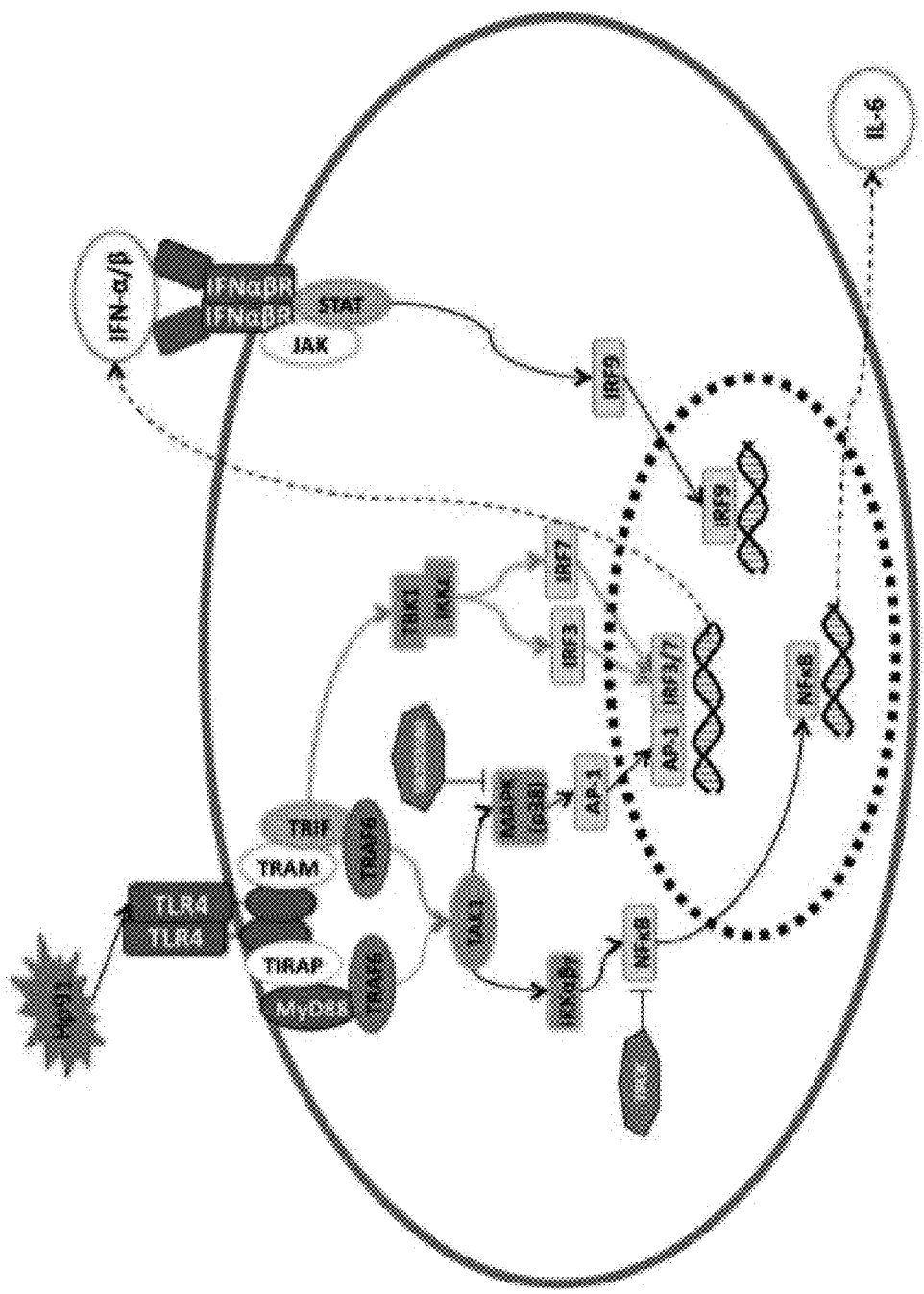
FIG. 21. A proposed mechanism of Hp91 signaling.

We used the BM-DC knockout IL-6 data, immunoblots, and small molecular inhibitor data to develop a proposed mechanism of Hp91 signaling (FIG. 21)

Discussion

As shown by confocal microscopy, Hp91 binds cells within 30 minutes on ice, as visible by a rim around the cells, and is taken up into the cells very rapidly in a sequence specific manner, as Hp121 does not enter cells. Scrambling the amino acids of Hp91 results in a great reduction of bindingluptake by cells, indicating that it is neither the total charge or total hydrophobicity that is important. Rather, we hypothesized that a particular sequence of amino acids is critical for the binding and uptake of peptide into cells, and that the region of the peptide responsible for activity could be investigated by testing shorter, overlapping peptides for their dendritic cell uptake as well as in vitro and in vivo immunostimulatory activity. In Example 3, we identify such a short immunostimulatory peptide, UC1018, that activates DCs and acts as adjuvant in vivo.

Using a panel of endocytosis inhibitors, we demonstrate that Hp91 is taken up in a clathrin-dependent manner. As clathrin-mediated endocytosis is receptor mediated, we explored possible receptors for Hp91.

TLR2 and TLR4, in particular, are interesting receptors in that they appear to bind many ligands with a large amount or promiscuity, and it has been difficult to find many structural similarities among the ligands. Matzinger theorizes that it is hydrophobic portions (hyppos) of molecules that interact with receptors such as TLR2 and TLR4 (42).

We show using knockout mice that Hp91-stimulated activation of DCs is dependent on TLR4 and MyD88. We further show, via phosphorylation of p38 and using p38 inhibitors, that Hp91 activates the MyD88-dependent signaling pathway. We show via Hp91-induced phosphorylation of IRF3 that Hp91 does signal through the interferon pathway, Furthermore, we demonstrate that Hp91. uptake is required for phosphorylation of this MyD88-independent pathway.

References for Example 2

1. Takeda K, Kaisho T, Akira S. Toll-like receptors. Annual Review of Immunology. 2003; 21:335-76.

2. Banchereau J, Steinman RM. Dendritic cells and the control of immunity. Nature. 1998; 392(6673):245-52.

3. Bianchi ME. DAMPs, PAMPs and alarmins; all we need to know about danger. Journhl of Leukocyte Biology. 2007; 81(1):1-5.

4. Matzinger P. Tolerance, danger, and the extended family. Annual Review Of Immunology. 1994; 12:991-1045.

5. Gallucci S, Matzinger P. Danger signals: SOS to the immune system. Current Opinion in Immunology. 2001; 13(1):114-9.

6. Gallucci S, Lolkema M, Matzinger P. Natural adjuvants: endogenous activators of dendritic cells. Nature Medicine. 1999; 5(11):1249-55.

7. Sauter B, Albeit M L, Francisco L, Larsson M, Somersan S, Bhardwal N. Consequences of cell death: exposure to necrotic tumor cells, but not primary tissue cells or apoptotic cells, induces the maturation of immunostimulatory dendritic cells. The Journl of Experimental Medicine. 2000; 191(3):423-34.

8. Basa S, Binder R J, Suto R, Anderson K M, Srivastava P K. Necrotic but not apoptotic cell death releases heat shock proteins, which deliver a partial maturation signal to dendritic cells and activate the NF-kappa B pathway. Int Immunol. 2000; 12(11):1539-46.

9. Agresti A, Bianchi M E. HMGB proteins and gene expression. Curr Opin Genet Lev. 2003; 13(2):170-8.

10. Bustin M, Lehn D A, Landsman D. Structural features of the HMG chromosomal proteins and their genes. Biochimica Et Biophysica Acta. 1990; 1049(31:231-43.

11. Bustin M, Reeves R. High-mobility-group chromosomal proteins: architectural components that facilitate chromatin function. Progress in Nucleic Acid Research and Molecular Biology. 1996; 54:35-100.

12. Wang H, Vishnubhakat J M, Bloom O, Zhang M, Ombrellino M, Sarna A, et al. Proinflammatoty cytokines (tumor necrosis factor and interielikin 1) stimulate release of high mobility group protein-1 by pituicytes. Surgery. 1999; 126(2):389-92.

13. Andersson U, Wang H, Palmblad K, Aveberger AC, Bloom O, Erlandsson_Harris H, et al. High mobility group 1 protein (HMG-1) stimulates proinflammatory cytokine synthesis in human monocytes. The Journal of Experimental Medicine. 2000; 192(4):565-70.

14. Hreggvidsdottir H S, Ostberg T, Wahamaa H, Schierbeck H, Aveberger A C, Klevenvall L, et al. The alarmin HMGB1 acts in synergy with endogenous and exogenous danger signals to promote inflammation. J Leukoc Biol. 2009; 86(3):655-62.

15. Scaffidi P. Misteli T, Bianchi M E. Release of chromatin protein HMGB1 by necrotic cells triggers inflammation. Nature. 2002; 418(6894):191-5.

16. Rovere-Querini P, Capobianco A, Scaffidi P, Valentinis B, Catalanotti F, Giazzon M, et al. HMGB1 is an endogenous immune adjuvant released by necrotic cells. EMBO Rep. 2004; 5(8):825-30.

17. Hori O, Brett J, Slattery T, Cao R, Zhang J, Chen J X, et al. The receptor for advanced glycation end products (RAGE) is a cellular binding site for amphoterin. Mediation of neurite outgrowth and co-expression of rage and amphoterin in the developing nervous system. J Biol Chem. 1995; 270(43):25752-61.

18. Dumitrin I E, Baruah P, Bianchi M E, Manfredi A A, Rovere-Querini P. Requirement of HMGB1 and RAGE for the maturation of human plasmacytoid dendritic cells. Eur J Immunol. 2005; 35(7):2154-90.

19. Park J S, Svetkauskaite D, He Q, Kim J Y, Strassheim D, Ishizaka A, et al. Involvement of toll-like receptors 2 and 4 in cellular activation by high mobility group box 1 protein. J Biol Chem. 2004; 279(9):7370-7.

20. van Zoelen M A, Yang H, Florquin S, Meijers J C, Akira S, Arnold B. et al. Role of Toll-Like Receptors 2 and 4, and the Receptor for Advanced Ci cation End Products (Rage) in Hmgb1 Induced Inflammation in Vivo. Shock. 2008.

21. Yu M, Wang H, Ding A, Golenbock D T, Latz E, Czura, C J, et al. HMGB1 signals through toll-like receptor (TLR) 4 and TLR2. Shock. 2006; 26(2):174-9.

22. Park J S, Gamboni-Robertson F, He Q, Svetkauskaite D, Kim J Y, Strassheim D, et al. High mobility group box 1 protein interacts with multiple Toll-like receptors. Am J Physiol Cell Physiol. 2006; 290(3):C917-24.

23. Yang H. Hreggvidsdottir H S, Palmblad K, Wang H, Ochani M, Li J. et al. A critical cysteine is required for HMGB1 binding to Toll-like receptor 4 and activation of macrophage cytokine release. Proc Natl Acad Sci U S A. 2010; 107(26):11942-7. PMCID: 2900689.

24. Ivanov S. Dragoi A M, Wang X, Dallacosta C, Louten J, Musco G, et al. A novel role for HMGB1 it TLR9-mediated inflammatory responses to CpG-DNA. Blood. 2007; 110(6):1970-81. PMCID: 1976374.

25. Orlova V V, Choi E Y, Xie C, Chavakis E. Bierhaus A, Ihanus E. et al. A novel pathway of HMGB1-mediated inflammatory cell recnitment that requires Mac-1-integrin. EMBO J. 2007; 26(4):1129-39. PMCID: 1852832.

26. Rauvala H, Rouhiainen A. Physiological and pathophysiological outcomes of the interactions of HMGB1 with cell surface receptors. Biochim Biophys Acta. 2010; 1799 (1-2):164-70.

27. Salinivirta M, Rauvala H, Elenius K, Jalkanen M. Neurite growth-promoting protein (amphoterin, p30) binds syndecan. Exp Cell Res. 1992; 200(2):444-51.

28. Milev P, Chiba A, Haring M, Rauvala H, Schachner M, Ranscht B, et al. High affinity binding and overlapping localization of neurocan and phosphacan/protein-tyrosine phosphatase-zeta/beta with tenascin-R, amphoterirt, and the heparin-binding growth-associated molecule. J Biol Chem. 1998; 273(12):6998-7005.

29. Chen G Y, Tang J. Zheng P. Liu Y. CD24 and Siglec-10 selectively repress tissue damage-induced immune responses. Science. 2009; 323(5922):1722-5. PMCID: 2765686.

30. Li J, Kokkola R, Tabibzadeh S, Yang R, Ochani M, Qiang X, et al. Structural basis for the proinfiammatory cytokine activity of high mobility group box 1. Mol Med. 2003; 9(1-2):37-45.

31. Yang H, Wang H, Czura C J, Tracey K J. HMGB1 as a cytokine and therapeutic target. 2002; 8(6):469-72.

32. Telusma G, Datta S, Mihajlov I, Ma W, Li J, Yang H, et al. Dendritic cell activating peptides induce distinct cytokine profiles. International Immunology. 2006; 18(11): 1563-73.

33. Messmer D, Yang H, Telusma G, Knoll F, Li J, Messmer B, et al. High mobility group box protein 1: an endogenous signal for dendritic cell mat ration and Th1 polarization. Journal of Immunology. 2004; 173(1):307-13.

34. Telusma G, Datta S, Mihajlov I, Ma W, Li J, Yang H, et al. Dendritic cell activating peptides induce distinct cytokine profiles. Int Immunol. 2006; 18(11);1563-73.

35. Saenz R, Souza Cda 5, Huang C T, Larsson M, Esener S. Messmer D. HMGB1-derived peptide acts as adjuvant inducing immune responses to peptide and protein antigen. Vaccine. 2010; 28(47):7556-62. PMCID: 2963688.

36. Inaba K, Inaba M, Romani N, Aya H, Deguchi M, Ikehara S, et al. Generation of large numbers of dendritic cells from mouse bone marrow cultures supplemented with granulocyte/macrophage colony-stimulating factor. The Journal of Experimental Medicine. 1992; 176(6):1693-702.

37. Zaro J L, Shen W C. Quantitative comparison of membrane transduction and endocytosis of oligopeptides. Biochemical and Biophysical Research Communications. 2003; 307(2):241-7.

38. Messmer B, Yang H, Telusma G, Knoll F, Li J, Messmer B, et al. High mobility group box protein 1: an endogenous signal for dendritic cell maturation and Thl polarization. J Immunol. 2004; 173(1):307-13.

39. Kagan J C, Su T, Horng T. Chow A, Akira S, Medzhitov R. TRAM couples endocytosis of Toll-like receptor 4 to the induction of interferon-beta. Nat Immunol. 2008; 9(4):361-8.

40. Watts C. Location, location, location, identifying tha neighborhoods of LPS signaling. Nat Immunol. 2008; 9(4): 343-5.

41. Pujals S, Giralt E. Proline-rich, amphipathic cell-penetrating peptides. Adv Drug Deliv Rev. 2008; 60(4-5): 473-84.

42. Seong S Y, Matzinger P. Hydrophobicity: an ancient damage-associated molecular pattern that initiates innate immune responses. Nat Rev Immunol. 2004; 4(6):469-78.

Example 3

Materials and Methods

Animals

Female C57BL/6 mice 8-12 weeks of age were used for experiments. All mice were purchased from Charles River Laboratories (Boston, Mass., USA) and housed at the Moores UCSD Cancer Center animal facility. All animal studies were approved by the Institutional Animal Care and Use Committee of UCSD and were performed in accordance with the institutional guidelines.

Peptides

The peptides, including Hp91 (DPNAPKRPPSAF-FLFCSE (SEQ ID NO:2), UC18 (DPNAPKRP) (SEQ ID NO: 49), UC411 (APKRPPSA) (SEQ ID NO: 50), UC714 (RPPSAFFL) (SEQ ID NO: 51), UC718 (RPPSAFFLFCSE) (SEQ ID NO: 3), UC1018 (SAFFLFCSE) (SEQ ID NO: 1), AND SINFEKL (SEQ ID NO: 45) were all purchased from GenScript Corp (Piscataway, N.J., USA) and CPC Scientific (San Jose, Calif., USA). UC1018 mutated peptides (shown in FIG. 26) were synthesized at CPC Scientific. For uptake experiments and immunizations, peptides were synthesized with an N-terminal biotin. For DC stimulation experiments, peptides were synthesized with an N-terminal acetyl group. Peptides were routinely synthesized with greater than 95% purity. Unless otherwise stated, all peptides were dissolved in RPMI.

Cells

The murine melanoma B16.F1 cell line, transduced with a cDNA encoding the chicken ovalbumin gene (B16cOVA), was a gift from Richard Vile (Mayo) and were previously described (15). The cells were cultured in Dulbecco's modification of Eagle's Medium (Mediatech, Manassas, Va.), supplemented with 2 mM L-glutamine (GIBCO-BRL Life Technologies, Grand Island, N.Y.), 10 mmol HEPES (GIBCO-BRL), penicillin (100 U/mL)-streptomycin (100 µg/mL) (GIBCO-BRL), and 10% (vol/vol) fetal calf serum (Omega). To induce apoptosis of B16 cells, the ceils were treated with 0.5 mg ml$^{-1}$ mitomycin C in DMEM media for 60 minutes at 37° C. Cells were washed twice in warm DMEM and put back to culture overnight in DMEM supplemented as above.

Maleimide Conjugation Reactions

Hp91 peptide monomers, capped at the thiol group of the cysteine, were generated using an N-Ethylmaleimide (NEM) (Thermo Scientific) conjugation reaction. Briefly, Hp91 was dissolved in PBS and reacted for 2 h at RT in the presence of NEM. Hp91 peptide maleimide aimers, cross-linked at the thiol group of the cysteine, were generated using a Bis-maleimidoetbylenegiycol (BM(PEG)$_2$) (Thermo Scientific) conjugation reaction. Briefly, Hp91 was dissolved in PBS/EDTA and reacted for 1 h at RT in the presence of BM(PEG)$_2$. Excess NEM or BM(PEG)$_2$, respectively, was removed by dialysis (2K MWCO cassette, Thermo Scientific). Un-reacted, mock peptide controls were generated under identical reaction and dialysis conditions, while excluding the NEM or BM(PEG)$_2$ reagent. Reagents, glassware, and reaction products were endotoxin-free as determined by the manufacturer or a limulus amoebocyte assay (LAL) (Camhrex Corporation, East Rutherford, N.J.) tested according to manufacturer's instructions. Peptides with a biotin at the N-terminal group were used for binding/uptake experiments. Peptides with an acetyl at the N-terminal group were used for DC stimulation experiments.

Spontaneous Oxidation and Dithiothreitol-Reduction of Hp91

Hp91 was incubated in PBS at RT for 24 to 96 h to allow spontaneous oxidation of cysteine residues. In some experiments, the peptide was incubated for 30 min +/− 10 mM dithiothreitol (DTT) (Thermo Scientific) and/or 1% H$_2$O$_2$ (Thermo Fischer Scientific) to reduce or further oxidize the peptide, respectively.

Generation of Human Monocyte-Derived DCs

Peripheral blood mononuclear cells were isolated from the blood of normal volunteers over a Ficoll-Hypaque (Amersham Biosciences, Uppsala, Sweden) density gradient. Anonymous blood was purchased from the San Diego Blood Bank; therefore, no institutional review board approvals were necessary. To generate DCs, peripheral blood mononuclear cells were allowed to adhere to culture plates for 1 hour. The nonadherent cells were washed off, and the adherent cells were cultured in RPMI 1640 medium (Invitrigen) supplemented with 50 mmol 2-mercaptoethanol (Sigma), 10 mmol HEPES (GIBCO-BRL), penicillin (100 U mL$^{-1}$)—streptomycin (100 µg mL$^{-1}$)—L-glutamine (2 mM) (GIBCO-BRL), and 1% (vol/vol) human plasma (Valley Biomedical, Winchester, Va.) supplemented with GM-CSF (1000 U mL$^{-1}$) (Bayer HealthCare Pharmaceuticals, Wayne, N.J.), and interleukin-4 (100 U mL$^{-1}$) (IL-4; R and D Systems, Minneapolis, Minn.) at days 0, 2, and 4. Immature human DCs (iDCs) were harvested on days Stimulation of DCs At days 5-7 of culture, immature dendritic cells were either left untreated or were stimulated with Hp91 maleimide reaction products, Hp91 controls, or short peptides as indicated and incubated at 37° C. Supernatants were collected 48 h after stimulation and were analyzed for IL-6 by ELISA (eRioscience), according to the manufacturer's instructions.

Peptide Binding/Uptake Studies

Immature DCs were incubated for the indicated times and temperatures in culture medium with biotinylated peptides, biotinylated peptide reaction products or unreacted, mock controls. Cells were washed, permeabilized with Cytatix/Cytoperm, stained with Streptavidin-Alexa 488, and analyzed by flow cytometry.

Peptide immunization and spleen cell preparation

Mice were immunized s.c. with 50 µg of SIINFEKL peptide. The SIINFEKL peptide was co-administered with either PBS, Hp91 (250 µg), UC714 (129 µg), or UC1018 (142 µg). Hp91, UC714, and UC1018 peptide doses were equimolar. Mice were boosted two weeks later and spleens and blood were collected one week after the final immunization. Single cell suspensions of splenocytes were prepared by mechanical disruption and separation through a 70 mm nylon cell strainer (BI) Biosciences, Franklin Lakes, N.J., USA). Red blood cells were lysed using ammonium chloride buffer (Roche Diagnostics, Indianapolis, Ind., USA) and the splenocytes were subsequently resuspended in complete medium (RPMI 1640 with 10% FBS, L-glutamine, penicillin, streptomycin, and HEPES). Peptides were dissolved in PBS for all immunizations.

Enzyme-Linked Immunospot Assay

Freshly isolated splenocytes were plated in duplicate to wells of a nitrocellulose bottom enzyme-linked immunospoi (ELISPOT) plate (Millipore, Millerica, Mass., USA) that had been previously coated overnight with 5 μg ml$^{-1}$ monoclonal anti-mouse IFN-γ antibody (Mabtech, Stockholm, Sweden). Splenocytes were cultured overnight at 37° C. with 2.5 μg ml$^{-1}$ SHNFEKL peptide, 5 μg ml$^{-1}$ concanavalin A positive control (Sigma), or left unstimulated (medium only). After 18 h, ELISPOT plates were developed using 1 μg ml$^{-1}$ biotinylated anti-mouse IFN-γ antibody (Mabtech), Streptavidin-HRP (Mabtech), and TMB Substrate (Mabtech). The plate was scanned and the spots were counted using an automated ELISpot Reader System (CTL ImmunoSpot, Shaker Heights, Ohio, USA).

Cytokine Release Assay

To measure cytokine release from immunized mice, splenocytes were cultured overnight with 2.5 μg ml$^{-1}$ SIINFEKL peptide, 5 μg ml$^{-1}$ concanavalin A positive control (Sigma), or left unstimulated (media only). After 18 h, cell culture supernatants were collected and analyzed for the presence of IL-2 by ELISA (eBioscience).

Prophylactic B16 Tumor Challenge

Mice were immunized s.c. with 2×10$^5$ apoptotic mitomycin-C (Sigma)-treated B16 cells co-administered with either PBS or UC1018 (142 μg). Mice were boosted twice, at 4 weeks and 6 weeks post-prime as above, and challenged s.c, into the flank with 2×10$^5$ live B16 cells at one week post-boost. Mice were followed for tumor growth and survival. Tumor dimensions were measured using calipers and the tumor volume calculated using the following formula; volume=4/3 π(a$^2$×b). Mice were euthartized when tumor volume reached 1.5 cm$^3$. Tumor survival curves were generated, wherein the day of euthanasia was considered as death.

HPLC

Peptides were evaluated by HPLC (Agilent 1100 Series, Software: Chemstation) at 211 nm (column: ZORBAX RP C18). Percent dirtier was calculated as the area under the curve (AUC) of dimer/(AUC of monomer+AUC of dimer).

Circular Dichroism

CD spectra of peptides, dissolved in 75%/25% Trifluoroethanol (TFE, Sigma)/H$_2$O (vol/vol), were collected on an AVIV model 202 Circular Dichroism Spectrometer, under nitrogen, using a 1 mm pathlength quartz cuvette. These spectra were corrected by subtraction of a "solvent-only" spectrum and smoothed. The spectra are shown in mean residue ellipticity ($θ_{mrw}$). Peptides were analyzed at 200 μg ml$^{-1}$.

Statistical Analysis

Data represented are mean ±SEM. Data were analyzed for statistical significance using unpaired or paired Student's t-test. Statistical analysis was performed using GraphPad software version 5.01 for Windows (GraphPad Software, San Diego, Calif., USA). A p value <0.05 was considered statistically significant.

Results

Hp91 Forms Spontaneous Reversible Dimers

Figure 22:
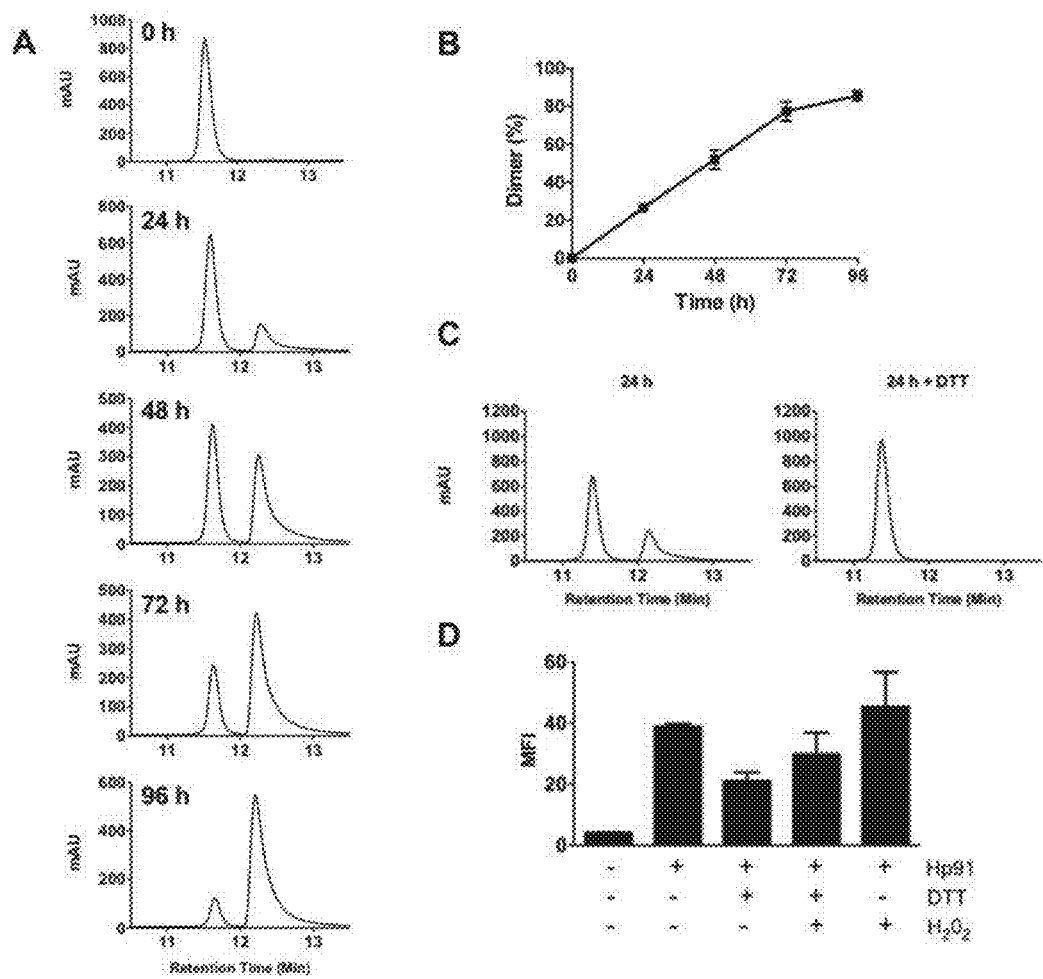
FIG. 22. HPLC and DC uptake of Hp91 spontaneous dimers. (A-B) Hp91 peptide was dissolved in PBS and incubated at RT in the presence of oxygen for up to 96 h. Peptides were analyzed by HPLC. Peptide monomers show a peak at an earlier time point than the peptide dimers (12.2 min vs. 12.7 min). Percent dimer was determined by measuring the AUC and calculating the dimer AUC/total AUC. Results shown are (A) representative of several independent experiments and (B) mean (±SEM) for 3-4 samples. (C) Hp91 was allowed to form spontaneous air dimers for 24 h prior to reduction with 10 mM DTT for 30 min. Peptides were analyzed by HPLC. (D) Biotinylated Hp91 was incubated for 30 min +/− dithiothreitol and/or H$_2$O$_2$. Immature human DCs were incubated with the modified peptides for 30 minutes at 37° C. Cells were permeabilized with Cytofix/Cytoperm, stained with Streptavidin-Alexa 488, and analyzed by flow cytometry. The data shown is mean (±SEM) for 4 independent experiments.

Cysteine residues, with an unprotected sulhydryl group, can form disulphide bridges. There is a cysteine at position 16 in Hp91 that could oxidize under certain conditions to form a peptide dimer with a second Hp91 molecule. Hp91 peptide, dissolved in PBS in the presence of oxygen, was incubated at RT for up to 96 h, and evaluated for the presence of dimers using HPLC. Hp91 dimers, running slower off the HPLC C18 column, were present at approximately 25% of the total peptide within 24 h. Dimers continued to form until measurements were stopped at 96 h, at which point greater than 80% of the peptide was in a dimer formation (FIG. 22A, 22B). To determine if this peptide dimer was stable or easily reversible, 24 h peptide dimers were allowed to form, and followed with a subsequent reduction in the presence of DTT. After 30 minutes at 10 mM DTT, all Hp91 peptide was found in a monomer state, as demonstrated by the reduction to a single HPLC peak (FIG. 22C).

As shown in Example 2, Hp91 binds and is endocytosed by DCs, as demonstrated by confocal microscopy and flow cytometry. Here we investigated if reducing or oxidizing the peptide would result in respective decreases or increases in uptake. There was no reason to believe that it would increase Hp91 activity. Compared to untreated peptide controls, uptake of DTT-reduced Hp91 peptide was reduced by approximately 50% (FIG. 22D). Addition of peroxide alongside the DTT maintained the peptide uptake at levels close to normal, where addition of peroxide to non-reduced peptide may enhance peptide uptake by a small amount. This data suggest that uptake of peptide may be enhanced by dimerization. This was a surprising, unexpected result.

Maleimide Dimers Enhance DC Activity

Since the DTT and peroxide appeared to have an affect on the uptake of Hp91, we generated capped peptide monomers and cross-linked peptide dimers using maleiruide conjugation reactions and evaluated the conjugated peptides for DC uptake and activation. Mono- or bis-maleimides contain an imide group that reacts readily with the thiol group of cysteine to form a stable carbon-sulfur bond. We predicted that this stability would enable us to conduct more robust experiments than would be possible with DTT- and peroxide-treated peptides. NEM is a mono-maleimide that generates a capped peptide monomer. BM(Peg)$_2$ is a his-maleimide that cross-links two peptides to form a dimer.

Figure 23:
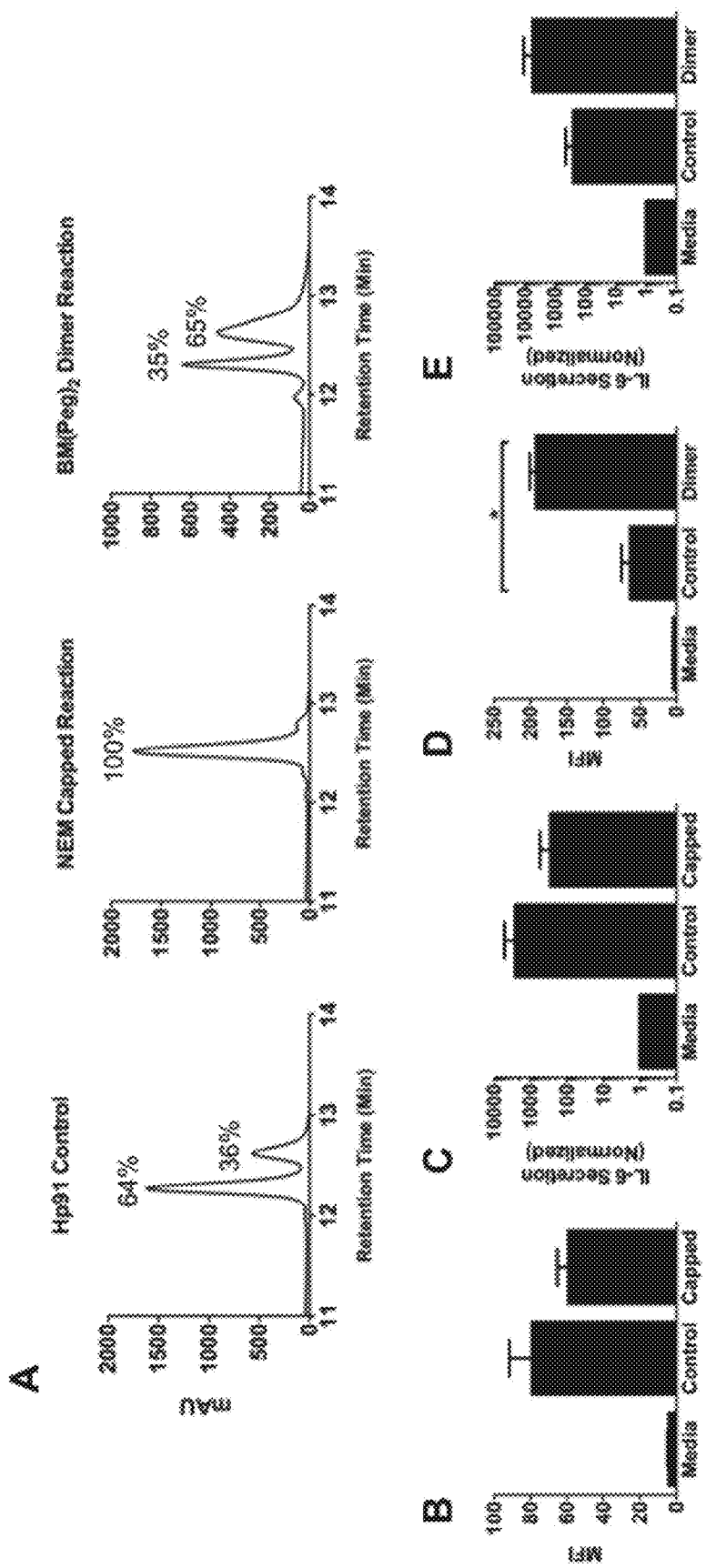
FIG. 23. HPLC and DC activity of Hp91 maleimide dimers. (A) Hp91 peptide control, NEM capped monomer reaction product, or BM(PEG)$_2$ cross-linked reaction product were analyzed by HPLC. Percent dimer was determined by measuring the AUC and calculating the dimer AUC/total AUC. (B) Immature human DCs were pre-cooled on ice for 30 minutes, then incubated with media only, biotinylated-Hp91 ("Control") or the biotinylated Hp91 NEM monomer reaction product ("Capped") (100 mg ml$^{-1}$) for 60 minutes at 37° C. Cells were permeabilized with Cytofix/Cytoperm, stained with Streptavidin-Alexa 488, and analyzed by flow cytometry. Results shown are mean (±SEM) for 3 independent experiments. (C) immature DCs were incubated with media only, un-reacted acetylated Hp91 ("Control"), or an acetylated Hp91 NEM monomer reaction product ("Capped") (100 mg ml$^{-1}$). Supernatants were collected after 48 hours and analyzed for the presence of IL-6 by ELISA. Data are normalized with respect to media controls. Results are mean (±SEM) for 3 independent experiments. (D) Immature human DCs were pre-cooled on ice for 30 minutes, then incubated with media only, biotinylated-Hp91 ("Control") or a biotinylated Hp91 BM(PEG)$_2$ cross-linked reaction product ("Dimer") (100 mg ml$^{-1}$) for 60 minutes at 37° C. Cells were permeabilized and stained as above and analyzed by flow cytometry. Results shown are mean (±SEM) for 3 independent experiments. *p<0.05; Student's t-test. (E) Immature DCs were incubated with media only, un-reacted acetylated Hp91 ("Control"), or an acetylated Hp91 BM(PEG)$_2$ cross-linked reaction product ("Dimer") (56 mg ml$^{-1}$). Supernatants were collected after 48 hours and analyzed for the presence of IL-6 by ELISA. Data are normalized with respect to media controls. Results are mean (±SEM) for 3 independent experiments.

HPLC of the rnaleimide conjugation reaction products shows that tae NEM capped monomer forms a single peptide peak, suggestive of close to 100% monomer, where the BM(PEG)2cross-linked dimer forms two peaks with an estimated 65% dimer (FIG. 23A). We evaluated the capped monomer for its ability to be taken up by DCs by incubating a biotinylated capped peptide, or control Hp91 peptide, with DCs and staining for uptake, as described above. Uptake was evaluated by flow cytometry and demonstrated that capping Hp91 and forcing it into a monomer state decreases its ability to be taken up by DCs by 27% (FIG. 23B), We tested whether the NEM capped peptide would similarly exert diminished immunostimulatory effects on DCs, we stimulated DC for 48 h with an acetylated capped Hp91 peptide, as compared to a control. As predicted, the Hp91 monomer exerts a reduced immunostimulatory effect on DC, as determined by a reduction in IL-6 secretion from DCs (FIG. 23C). Similar experiments concluded on the bis-maleimide dimers show that the dimer enhances uptake by 3-fold compared to controls (FIG. 23D), and enhances the immunostimulatory effects on DC, as shown by an approximately 10-fold increase in IL-6 secretion from stimulated DCs compared to controls (FIG. 23E). These results demonstrate that maleiniide Hp91 dimers enhance uptake and cytokine secretion front DCs.

Activity of Hp91 Resides in C-Terminal Amino Acids

Figure 24:
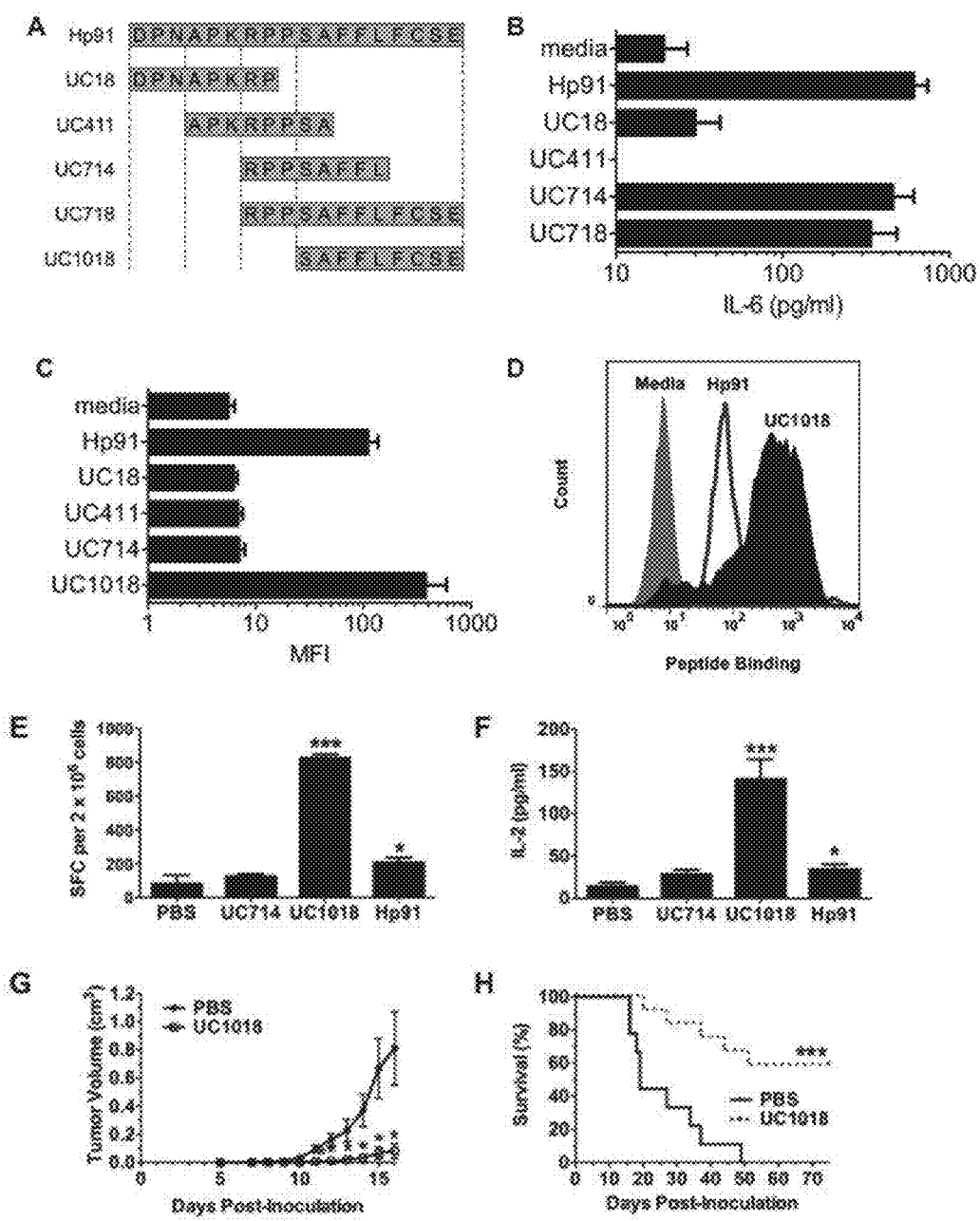
FIG. 24. Immunostimulatory activity of Hp91 short peptides. (A) Full length Hp91 (18 aa) is broken into 5 smaller, truncated peptides (8-12 aa). (B) Immature DCs were stimulated with the indicated peptides for 48 hours. Supernatants were analyzed for the presence of IL-6 by ELISA. Data are mean (±SEM) for 3 independent experiments. (C, D) Immature DCs were precooled on ice for 30 minutes, then incubated with medium only, Hp91, or truncated Hp91 short peptides (90 μM) for 30 minutes at 37° C. Cells were permeabilized with Cytofix/Cytoperm, stained with Streptavidin-Alexa 488, and analyzed by flow cytometry. (C) is mean (±SEM) of 4 independent experiments and (D) is a representative result. (E-F) Mice were immunized with SIINFEKL peptide in PBS with PBS (negative), UC714, UC1018, or Hp91. Freshly isolated splenocytes from the immunized mice were cultured in the presence of SIINFEKL peptide (2.5 μg ml–1) in an (E) IFN-γ ELISPOT assay, wherein the number of IFN-γ-secreting cells was determined 18 h later, or (F) culture supernatants were collected and analyzed for IL-2 secretion by ELISA. The data shown is mean (±SEM) for at least 5 mice/group. *p<0.05 compared to PBS; Student's t-test, (G-H) Mice were immunized s.c. with apoptotic mitomycin-C treated B16 cells co-injected with PBS (negative) or UC1018 peptide (142 μg) and boosted twice. One week post boost, mice were inoculated s.c. on the flank with 5×10$^5$ live B16 cells. (G) Tumor dimensions were measured using calipers and the tumor volume calculated using the following formula; volume 4/3 π(a$^2$×b). The data shown is mean (±SEM) for at least 14 mice/group. *p<0.01 compared to PBS; Student's t-test at each time point. (H) Mice were euthanized when tumor volume reached 1.5 cm$^3$. Tumor survival curves were generated, wherein the day of euthanasia was considered as death. ***p<0.001 compared to PBS; Student's t-test.

In an effort to identify the region of Hp91 required for DC binding and activation, overlapping 8-12 aa long peptides that span the length of Hp91 were synthesized and evaluated (FIG. 24A). DCs were incubated with the indicated short peptides and supernatants were tested after 48 hours for the presence of IL-6. While the C-terminal half of the peptide induced IL-6 at levels comparable to the full-length peptide, the N-terminal failed to induce cytokine secretion from DCs (FIG. 24B). Similar IL-6 secretion was observed from mouse BM-DCs stimulated with UC714 and UC718 peptides.

To test uptake of the short peptides, DCs were incubated with biotinylated versions of the short peptides for 30 minutes at 37° C. to allow uptake. Cells were fixed, permeabilized, stained with streptavidin-Alexa 488, and evaluated by flow cytometry. The 9 aa acid long peptide UC1018, which corresponds to the C-terminal half of Hp91, enhanced uptake by DCs over 3-fold compared to Hp91 controls (FIG. 24C, 24D). This was very surprising and unexpected. In contrast, UC18, UC411, and UC714, containing varying portions of the N-terminal 14 aa of Hp91, failed to be endocytosed by DCs (FIG. 24C, 24D).

The C-terminal half of Hp91 peptide appeared responsible for in vitro activity of Hp91, thus we set out to verify if the C-terminal domain was similarly responsible for in vivo activity. We have previously shown that full-length Hp91 peptide acts as adjuvant in vivo to induce antigen-specific immune responses. We hypothesized that either one or both of the C-terminal short peptides, UC714 and UC1018, would act as adjuvant to induce antigen-specific immune responses in vivo. One would expected that if the short peptides had adjuvant activity, it would be less than the 18 mer. Mice were co-immunized with ovalbumin (SIIFEKL) peptide as antigen and equimolar amounts of UC714, UC1018, or Hp91. The CTD UC1018 induced a significant increase in the number of antigen-specific IFNγ-secreting T cells compared to PBS controls as measured by ELISPOT (FIG. 24E). These UC1018-induced immune responses were 4-fold stronger than our Hp91 positive control. This was extremely unexpected as it is half the length of the 18 mer. UC714, though showing moderate increases in IFNγ-secreting T cells compared to PBS, showed only 50% of the IFNγ-secreting T cells observed with full-length Hp91 peptide (FIG. 24E). We further show that IL-2, which is critical for the activation, survival, and proliferation of T lymphocytes, was significantly enhanced in mice immunized with UC1018, at levels 4-fold higher even than Hp91 controls (FIG. 24F). This was unexpected.

In cancer treatment, an antigen-specific immune response becomes more meaningful if it translates into a survival advantage. As UC1018 peptide induced a significant antigen- specific immune response in vivo, we tested whether UC1018 could act as adjuvant in a prophylactic tumor challenge to induce anti-tumor immunity. Mice were co-immunized with apoptotic B16 melanoma cells and either PBS or UC1018 peptide. Mice were boosted twice and challenged one week post boost with live B16 melanoma cells. The melanoma model used in this study is highly lethal, such that within 7-10 days, the PBS control mice demonstrated tumor formation and rapid tumor growth, with the first mouse being sacrificed by day 16 post challenge due to a substantial tumor burden (FIG. 24G). in marked contrast to the PBS group, the UC1018 peptide immunized mice demonstrated a delay in tumor formation and slowing of tumor growth, significant as early as 11 days post challenge (FIG. 24G), indicating an induction of significant protective anti-tumor immunity in the UC1018 immunized mice. The mice were monitored for survival, and mice that received the UC1018 prophylactic treatment demonstrated a striking and significant enhancement of survival, with 60% of mice tumor-free and alive at 75 days post tumor challenge (FIG. 24H). In contrast, all mice in the control group developed tumor with 100% of mice succumbing to tumor burden by 49 days post challenge (FIG. 24H)

C-Terminal Portion of Hp91 is Helical

As the CTD of Hp91, UC1018, is important for DC uptake and for exerting its immunostimulatory effects, we set out to evaluate the secondary structure of this peptide. Circular dichroism (CD) measures the difference in absorbance of right- and left-circularly polarized light. The phenomenon of CD is sensitive to the secondary structure of polypeptides and can be used between wavelengths of 190-250 nm to analyze a peptide for different structural types such as alpha helix, beta sheet, polyproline II helix, random coil, and more.

Figure 25:
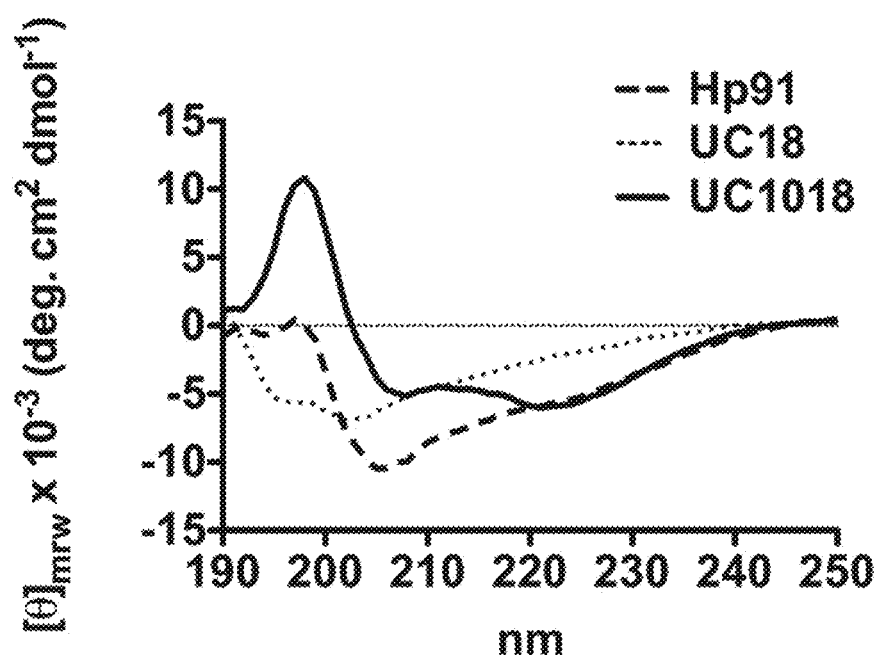
FIG. 25. Circular dichoism suggests alpha helical shape of UC1018. Hp91, UC18, and UC1018 were dissolved in 75%/25% Trifluoroethanol (TEE, Sigma)/H$_2$O (vol/vol) at 200 μg ml$^{-1}$ and CD spectra were collected on an AVIV Circular Dichroism Spectrometer using a 1 mm pathlength quartz cuvette. These spectra were corrected by subtraction of a "solvent-only" spectrum and smoothed. The spectra are shown in mean residue ellipticity (θ$_{mrw}$). The Hp91 curve is representative of two independent experiments.

To perform the CD experiment, we dissolved peptides in a trifluoroethanol (TFE) buffer (75%/25% TFE/$H_2O$ by volume), which enhances polypeptide folding and structures by allowing hydrophobic portions to fold as they might in vivo. The CD spectrum of the CTD UC1018 showed negative ellipticity bands at 207 and 222 nm, with a positive ellipticity at 198 nm (FIG. 25). Such a spectra is characteristic of an alpha helix. The CD spectrum for the NTD UC18 showed a negative maximum at 202 nm (FIG. 25), which is close to the negative peak expected at 200 nm for a proiyproline II helix. A spectra with a negative peak around 200 nm is relatively ambiguous however, as random coils also display similar spectra. With some uncertainty, we conclude that the NTD UC18 is a polyproline II helix, rather than random coil. This is based on the peptide sequence that contains two PXXP motifs, which are known to form polyproline II helices (118). The CD spectrum for the entire length of Hp91 remains more difficult to interpret. The negative peak near 205 for Hp91. (FIG. 25) may be an additive effect of the NTD and CTD spectra negative maximums.

Mutating Amino Acids Can Strengthen Immunostimulatory Potential

Figure 26:
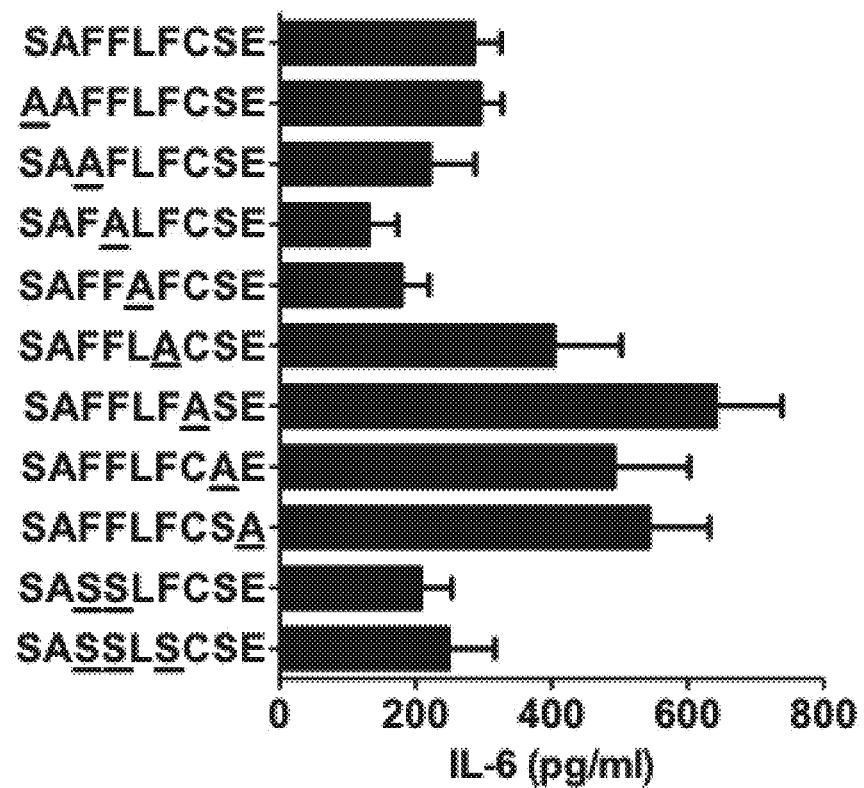
FIG. 26. Immunostimulatoiy activity of UC1018 mutated peptides. Immature DCs were stimulated with the indicated peptides for 48 hours. Supernatants were analyzed for the presence of IL-6 by ELISA. Data are mean (±SEM) for 4 independent experiments.

UC 1018 short peptide showed surprising immunostimulatory potential in viva and acted IS as adjuvant, inducing anti-tumor responses. We hypothesized that we could mutate ammo acids to kill activity and identify the amino acids critical for Hp91 activity. Surprisingly, replacing each of the C-teminal 4 amino acids of UC1018 with an alanine resulted in strengthened IL-6 secretion from DCs (FIG. 26). This was completely unexpected. Replacing the phenylalanine residues with serines did not have much affect on the immunostimulatory activity of Hp91.

Discussion

There is a great need for safer and more potent adjuvants (16, 17). We have previously shown that the 18 amino acid long immunostimulatory peptide (ISP) Hp91 is a potent stimulus for human DCs with the ability to generate a Th1-type immune response in vitro (7). We have recently shown that Hp91 acts as adjuvant in vivo; inducing cellular immune responses to peptide and both cellular and humoral immune responses to protein antigen (8). The results presented here characterize the structural basis for Hp91 activity, identifying a new ISP, UC 1018, that acts as adjuvant in vivo and demonstrating that Hp91 dimerization enhances activity. In addition, we show that amino acid mutations of UC1018 maintain, if not strengthen immunostimulatory potential of the peptide.

We set out to investigate what structures and amino acid domains were responsible for the activity of the Hp91 immunostimulatory peptide and adjuvant. After determining that Hp91 formed spontaneous dimers in the presence of air, we tested whether these dimers would affect Hp91's activity. While we hypothesized that Hp91 dimerization at the cysteine might prevent proper binding and uptake into dendritic cells, surprisingly we discovered that dimers actually enhanced peptide uptake. We show in Example 2 that activity of Hp91 is dependent on TLR4. Toll-like receptors, such as TLR4, form homo- or hetero-dimers with other members of their protein family. Such homodimers of TLR4 are thought to be necessary for recruitment of adaptor proteins and subsequent signaling, as the Mal and TRAM adaptors are predicted to bind at the TLR4 dimer interface (18). It is possible that dimerization of Hp91 peptide promotes TLR4 dimerization, adaptor recruitment, and downstream signaling leading to activation of NFκB and IRF-3.

It is surprising to us that the dimers would enhance Hp91 activity. We could imagine the peptide binding to a groove in a single protein or receptor. It is hard to picture that a small peptide, even in dirtier form, would be large enough to simultaneously bind both subunits of the TLR4 homodimer.

In Example 2, we showed that the scrarribled version of Hp91 is not taken up by DCs, suggesting that it is neither the total charge nor hydrophobicity of the peptide that is important for Hp91 activity. Rather, it is a particular sequence of amino acids that leads to the immunostimulatory activity and binding of peptide to cells. In this example we determine the region of the peptide responsible for activity by testing shorter, overlapping peptides for their binding. Hp91 contains two PXXP motifs at the N-terminal half, present in short peptides UC18 and UC411, that we originally hypothesized may be responsible for the cell permeability and perhaps activity as cell permeable peptides often contain proline-rich regions (19, 20). To our surprise, it was the C-terminal end, not the N-terminal end of the peptide with activity. We demonstrate here that the C-terminal domain of Hp91 (the region that includes FCSE) induces cytokine release from DCs (UC718 peptide) and hinds or is taken up by dendritic cells (UCIO18). In addition, we show that the CTD, UC1018, is sufficient to act as adjuvant in vivo, inducing cellular, antigen-specific immune responses. Very surprisingly and unexpectedly, we demonstrate that UC1018, despite being only half the length of Hp91, is taken up by DCs to a much greater extent and is a 3-fold stronger adjuvant in vivo, as measured by IFN-γ ELISPOT and IL-2 cytokine release. Historically, shortening the HMGB1 protein to the B box domain reduced immunostimulatory activity, and similarly shortening the B box domain to the Hp91 peptide reduced the immunostimulatory activity further. Here, we surprisingly and unexpectedly show that shortening the sequence further, to UC1018, actually strengthens the immunostimulatory activity of the peptide.

We expected that mutating the amino acids of UC1018 would kill the immunostimulatory activity and help us identify the amino acids critical for activity. Surprisingly, we show here that mutating residues of the UC1018 peptide can result in increased immunostimulatory activity.

In summary, in this example we have investigated the activity of Hp91 inamunostimulatory peptide, whose structure-function relationships had not been clear before now. We show that Hp91 dimerization enhances activity and that the helical C-terminus, UC1018, has DC binding and adjuvant activity that is stronger than full-length Hp91, We show that it is possible to potentiate the adjuvant effect by mutating the C-terminal amino acids of UC1018.

References for Example 3

1. Rovere-Querini P, Capobianco A, Scaffidi P, Valentinis B, Catalanotti F, Giazzon M, et al. HMGB1 is an endogenous immune adjuvant released by necrotic cells. EMBO Rep. 2004; 5(8):825-30.
2. Agresti A, Bianchi M E. HMGB proteins and gene expression. Curr Opin Genet Dev. 2003; 13(2):170-8.
3. Scaffidi P, Misteli T, Bianchi M E. Release of chromatin protein HMBG1 by necrotic cells triggers inflammation. Nature. 2002; 418(6894): 191-5.
4. Ulloa L, Messmer D. High-mobility group box 1 (HMGB1) protein: friend and foe. Cytokine Growth Factor Rev. 2006; 17(3):189-201.
5. Wang H, Vishnubhakat J M, Bloom O, Zhang M, Ombrellino M, Sama A, et al. Proinflammatory cytokines (tumor necrosis factor and interleukin 1) stimulate release of high mobility group protein-1 by pituicytes. Surgery. 1999; 126(2):389-92.
6. Messmer D, Yang H, Telusma G, Knoll F, Li J, Messmer B, et al. High mobility group box protein 1: an endogenous signal for dendritic cell maturation and Th1 polarization. J Immunol. 2004; 173(1):307-13.
7. Telusma G, Datta S. Mihajlov I, Ma W, Li J, Yang H, et al. Dendritic cell activating peptides induce distinct cytokine profiles. Int Immunol. 2006; 18(11):1563-73.
8. Saenz R, Souza Cda S, Huang C T, Larsson M, Esener S, Messmer D. HMGB1-derived peptide acts as adjuvant inducing immune responses to peptide and protein antigen. Vaccine. 2010; 28(47):7556-62. PMCID: 2963688.
9. Yang H, Hreggvidsdottir H S, Palmblad K, Wang H, Ochani M, Li J, et al. A critical cysteine is required for HMGB1 binding to Toll-like receptor 4 and activation of macrophage cytokine release. Proc Natl Acad Sci U S A. 2010; 107(26):11942-7. PMCID: 2900689.
10. Hoppe G, Talcott K E, Bhattacharya S K, Crabb J W, Sears J E. Molecular basis for the redox control of nuclear transport of the structural chromatin protein Hmgb1. Exp Cell Res. 2006; 312(18):3526-38.
11. Bienkiewicz E A, Moon Woody A, Woody R W. Conformation of the RNA polymerase II C-terminal domain: circular dichroism of long and short fragments. J Mol Biol. 2000; 297(1):119-33.
12. van Hoist G J, Fincher G B, Polyproline II Confirmation in the Protein Component of Arabinogalactan-Protein from Lolium multiflorum. Plant Physiol. 1984; 7501: 1163-4. PMCID: 1067069.
13. Yu H, Chen J K, Feng S, Dalgarno D C, Brauer A W, Schreiber S L. Structural basis for the binding or proline-rich peptides to SH3 domains. Cell. 1994; 76(5):933-15.
14. Li SS. Specificity and versatility of SH3 and other proline-recognition domains: structural basis and implications for cellular signal transduction. Biochem J. 2005; 390(Pt 3):641-53. PMCID: 1199657.
15. Linardakis E, Bateman A, Phan V, Ahmed A, Gough M, Olivier K, et al. Enhancing the efficacy of a weak allogeneic melanoma vaccine by viral fusogenic membrane glycoprotein-mediated tumor cell-tumor cell fusion. Cancer Res. 2002; 62(19):5495-504.
16. Singh M, O_Hagan D. Advances in vaccine adjuvants. Nature Biotechnology. 1999; 17(11):1075-81.
17. McCluskie M J, Weeratha R D. Novel adjuvant systems. 2001; 1(3):263-71.
18. Nunez Miguel R, Wong J, Westoll J F, Brooks H J, O'Neill L A, Gay N J, et al. A dimer of the Toll-like receptor 4 cytoplasmic domain provides a specific scaffold for the recruitment of signalling adaptor proteins. PLoS One. 2007; 2(8):e788. PMCID: 1945083.
19. Pujals S, Giralt E. Proline-rich, amphipathic cell-penetrating peptides. Adv Drug Deliv Rev. 2008; 60(4-5): 473-84.
20. Fernandez-Carneado J, Kogan M J, Van Mau N, Pujals S, Lopez-Iglesias C, Heitz F, et al. Fatty acyl moieties: improving Pro-rich peptide uptake inside HeLa cells. J Pept Res. 2005; 65(6):580-90.

SEQUENCE LISTING

```
<160> NUMBER OF SEQ ID NOS: 59

<210> SEQ ID NO 1
<211> LENGTH: 9
<212> TYPE: PRT
<213> ORGANISM: Artificial Sequence
<220> FEATURE:
<223> OTHER INFORMATION: UC1018 peptide

<400> SEQUENCE: 1

Ser Ala Phe Phe Leu Phe Cys Ser Glu
1               5

<210> SEQ ID NO 2
<211> LENGTH: 18
<212> TYPE: PRT
<213> ORGANISM: Artificial Sequence
<220> FEATURE:
<223> OTHER INFORMATION: Hp91 peptide

<400> SEQUENCE: 2

Asp Pro Asn Ala Pro Lys Arg Pro Pro Ser Ala Phe Phe Leu Phe Cys
1               5                   10                  15

Ser Glu

<210> SEQ ID NO 3
<211> LENGTH: 12
<212> TYPE: PRT
<213> ORGANISM: Artificial Sequence
<220> FEATURE:
<223> OTHER INFORMATION: UC718 peptide

<400> SEQUENCE: 3

Arg Pro Pro Ser Ala Phe Phe Leu Phe Cys Ser Glu
1               5                   10

<210> SEQ ID NO 4
<211> LENGTH: 9
<212> TYPE: PRT
<213> ORGANISM: Artificial Sequence
<220> FEATURE:
<223> OTHER INFORMATION: immunostimulatory peptide
<220> FEATURE:
<221> NAME/KEY: MISC_FEATURE
<222> LOCATION: (6)..(9)
<223> OTHER INFORMATION: X1 may be alanine (A), glycine (G), or valine
      (V) and X2 is cysteine (C), X3 is serine (S) and X4 is glutamic
      acid (E)
<220> FEATURE:
<221> NAME/KEY: MISC_FEATURE
<222> LOCATION: (6)..(9)
<223> OTHER INFORMATION: X2 may be alanine (A), glycine (G), or valine
      (V) and X1 is phenylalanie (F), X3 is serine (S) and X4 is
      glutamic acid (E)
<220> FEATURE:
<221> NAME/KEY: MISC_FEATURE
<222> LOCATION: (6)..(9)
<223> OTHER INFORMATION: X3 may be alanine (A), glycine (G), or valine
      (V) and X1 is phenylalanine (F), X2 is cysteine (C) and X4 is
      glutamic acid (E)
<220> FEATURE:
<221> NAME/KEY: MISC_FEATURE
<222> LOCATION: (6)..(9)
<223> OTHER INFORMATION: X4 may be alanine (A), glycine (G), or valine
      (V) and X1 is phenylalanine (F), X2 is cysteine (C) and X3 is
      serine (S)
<220> FEATURE:
<221> NAME/KEY: MISC_FEATURE
<222> LOCATION: (6)..(9)
<223> OTHER INFORMATION: X1 may be alanine (A), glycine (G), valine
      (V), isoleucine (I), or leucine (L) and X2 is cysteine (C), X3
```

```
      is serine (S) and X4 is glutamic acid (E)
<220> FEATURE:
<221> NAME/KEY: MISC_FEATURE
<222> LOCATION: (6)..(9)
<223> OTHER INFORMATION: X1 is phenylalanine (F); X2 may be alanine (A),
      glycine (G), valine (V), isoleucine (I), or leucine (L); X3 is
      serine (S) and X4 is glutamic acid (E)
<220> FEATURE:
<221> NAME/KEY: MISC_FEATURE
<222> LOCATION: (6)..(9)
<223> OTHER INFORMATION: X1 is phenylalanine (F); X2 is cysteine (C);
      X3 may be alanine (A), glycine (G), valine (V), isoleucine (I),
      or leucine (L); and X4 is glutamic acid (E)
<220> FEATURE:
<221> NAME/KEY: MISC_FEATURE
<222> LOCATION: (6)..(9)
<223> OTHER INFORMATION: X1 is phenylalanine (F); X2 is cysteine (C);
      X3 is serine (S); and X4 may be alanine (A), glycine (G), valine
      (V), isoleucine (I), or leucine (L)

<400> SEQUENCE: 4

Ser Ala Phe Phe Leu Xaa Xaa Xaa Xaa
1               5

<210> SEQ ID NO 5
<211> LENGTH: 9
<212> TYPE: PRT
<213> ORGANISM: Artificial Sequence
<220> FEATURE:
<223> OTHER INFORMATION: immunostimulatory peptide
<220> FEATURE:
<221> NAME/KEY: MISC_FEATURE
<222> LOCATION: (6)..(6)
<223> OTHER INFORMATION: X may be alanine (A), glycine (G), valine (V),
      isoleucine (I), or leucine (L)

<400> SEQUENCE: 5

Ser Ala Phe Phe Leu Xaa Cys Ser Glu
1               5

<210> SEQ ID NO 6
<211> LENGTH: 9
<212> TYPE: PRT
<213> ORGANISM: Artificial Sequence
<220> FEATURE:
<223> OTHER INFORMATION: immunostimulatory peptide
<220> FEATURE:
<221> NAME/KEY: MISC_FEATURE
<222> LOCATION: (7)..(7)
<223> OTHER INFORMATION: X may be alanine (A), glycine (G), valine (V),
      isoleucine (I), or leucine (L)

<400> SEQUENCE: 6

Ser Ala Phe Phe Leu Phe Xaa Ser Glu
1               5

<210> SEQ ID NO 7
<211> LENGTH: 9
<212> TYPE: PRT
<213> ORGANISM: Artificial Sequence
<220> FEATURE:
<223> OTHER INFORMATION: immunostimulatory peptide
<220> FEATURE:
<221> NAME/KEY: MISC_FEATURE
<222> LOCATION: (8)..(8)
<223> OTHER INFORMATION: X may be alanine (A), glycine (G), valine (V),
      isoleucine (I), or leucine (L)

<400> SEQUENCE: 7

Ser Ala Phe Phe Leu Phe Cys Xaa Glu
1               5
```

-continued

```
<210> SEQ ID NO 8
<211> LENGTH: 9
<212> TYPE: PRT
<213> ORGANISM: Artificial Sequence
<220> FEATURE:
<223> OTHER INFORMATION: immunostimulatory peptide
<220> FEATURE:
<221> NAME/KEY: MISC_FEATURE
<222> LOCATION: (9)..(9)
<223> OTHER INFORMATION: X may be alanine (A), glycine (G), valine (V),
      isoleucine (I), or leucine (L)

<400> SEQUENCE: 8

Ser Ala Phe Phe Leu Phe Cys Ser Xaa
1               5

<210> SEQ ID NO 9
<211> LENGTH: 18
<212> TYPE: PRT
<213> ORGANISM: Artificial Sequence
<220> FEATURE:
<223> OTHER INFORMATION: immunostimulatory peptide
<220> FEATURE:
<221> NAME/KEY: MISC_FEATURE
<222> LOCATION: (15)..(18)
<223> OTHER INFORMATION: X1 may be alanine (A), glycine (G), or valine
      (V) and X2 is cysteine (C), X3 is serine (S) and X4 is glutamic
      acid (E)
<220> FEATURE:
<221> NAME/KEY: MISC_FEATURE
<222> LOCATION: (15)..(18)
<223> OTHER INFORMATION: X2 may be alanine (A), glycine (G), or valine
      (V) and X1 is phenylalanine (F), X3 is serine (S) and X4 is
      glutamic acid (E)
<220> FEATURE:
<221> NAME/KEY: MISC_FEATURE
<222> LOCATION: (15)..(18)
<223> OTHER INFORMATION: X3 may be alanine (A), glycine (G), or valine
      (V) and X1 is phenylalanine (F), X2 is cysteine (C) and X4 is
      glutamic acid (E)
<220> FEATURE:
<221> NAME/KEY: MISC_FEATURE
<222> LOCATION: (15)..(18)
<223> OTHER INFORMATION: X4 may be alanine (A), glycine (G), or valine
      (V) and X1 is phenylalanine (F), X2 is cysteine (C) and X3 is
      serine (S)
<220> FEATURE:
<221> NAME/KEY: MISC_FEATURE
<222> LOCATION: (15)..(18)
<223> OTHER INFORMATION: X1 may be alanine (A), glycine (G), valine
      (V), isoleucine (I), or leucine (L) and X2 is cysteine (C), X3
      is serine (S) and X4 is glutamic acid (E)
<220> FEATURE:
<221> NAME/KEY: MISC_FEATURE
<222> LOCATION: (15)..(18)
<223> OTHER INFORMATION: X1 is phenylalanine (F); X2 may be alanine (A),
      glycine (G), valine (V), isoleucine (I), or leucine (L); X3 is
      serine (S) and X4 is glutamic acid (E)
<220> FEATURE:
<221> NAME/KEY: MISC_FEATURE
<222> LOCATION: (15)..(18)
<223> OTHER INFORMATION: X1 is phenylalanine (F); X2 is cysteine (C);
      X3 may be alanine (A), glycine (G), valine (V), isoleucine (I),
      or leucine (L); and X4 is glutamic acid (E)
<220> FEATURE:
<221> NAME/KEY: MISC_FEATURE
<222> LOCATION: (15)..(18)
<223> OTHER INFORMATION: X1 is phenylalanine (F); X2 is cysteine (C);
      X3 is serine (S); and X4 may be alanine (A), glycine (G), valine
      (V), isoleucine (I), or leucine (L)

<400> SEQUENCE: 9

Asp Pro Asn Ala Pro Lys Arg Pro Pro Ser Ala Phe Phe Leu Xaa Xaa
1               5                   10                  15
```

Xaa Xaa

<210> SEQ ID NO 10
<211> LENGTH: 18
<212> TYPE: PRT
<213> ORGANISM: Artificial Sequence
<220> FEATURE:
<223> OTHER INFORMATION: immunostimulatory peptide
<220> FEATURE:
<221> NAME/KEY: MISC_FEATURE
<222> LOCATION: (15)..(15)
<223> OTHER INFORMATION: X is alanine (A), glycine (G), or valine (V)

<400> SEQUENCE: 10

Asp Pro Asn Ala Pro Lys Arg Pro Pro Ser Ala Phe Phe Leu Xaa Cys
1               5                   10                  15

Ser Glu

<210> SEQ ID NO 11
<211> LENGTH: 18
<212> TYPE: PRT
<213> ORGANISM: Artificial Sequence
<220> FEATURE:
<223> OTHER INFORMATION: immunostimulatory peptide
<220> FEATURE:
<221> NAME/KEY: MISC_FEATURE
<222> LOCATION: (16)..(16)
<223> OTHER INFORMATION: X is alanine (A), glycine (G) or valine (V)

<400> SEQUENCE: 11

Asp Pro Asn Ala Pro Lys Arg Pro Pro Ser Ala Phe Phe Leu Phe Xaa
1               5                   10                  15

Ser Glu

<210> SEQ ID NO 12
<211> LENGTH: 18
<212> TYPE: PRT
<213> ORGANISM: Artificial Sequence
<220> FEATURE:
<223> OTHER INFORMATION: immunostimulatory peptide
<220> FEATURE:
<221> NAME/KEY: MISC_FEATURE
<222> LOCATION: (17)..(17)
<223> OTHER INFORMATION: X is alanine (A), glycine (G) or valine (V)

<400> SEQUENCE: 12

Asp Pro Asn Ala Pro Lys Arg Pro Pro Ser Ala Phe Phe Leu Phe Cys
1               5                   10                  15

Xaa Glu

<210> SEQ ID NO 13
<211> LENGTH: 18
<212> TYPE: PRT
<213> ORGANISM: Artificial Sequence
<220> FEATURE:
<223> OTHER INFORMATION: immunostimulatory peptide
<220> FEATURE:
<221> NAME/KEY: MISC_FEATURE
<222> LOCATION: (18)..(18)
<223> OTHER INFORMATION: X is alanine (A), glycine (G) or valine (V)

<400> SEQUENCE: 13

Asp Pro Asn Ala Pro Lys Arg Pro Pro Ser Ala Phe Phe Leu Phe Cys
1               5                   10                  15

Ser Xaa

-continued

```
<210> SEQ ID NO 14
<211> LENGTH: 12
<212> TYPE: PRT
<213> ORGANISM: Artificial Sequence
<220> FEATURE:
<223> OTHER INFORMATION: immunostimulatory peptide
<220> FEATURE:
<221> NAME/KEY: MISC_FEATURE
<222> LOCATION: (9)..(12)
<223> OTHER INFORMATION: X1 may be alanine (A), glycine (G), or valine
      (V) and X2 is cysteine (C), X3 is serine (S) and X4 is glutamic
      acid (E)
<220> FEATURE:
<221> NAME/KEY: MISC_FEATURE
<222> LOCATION: (9)..(12)
<223> OTHER INFORMATION: X2 may be alanine (A), glycine (G), or valine
      (V) and X1 is phenylalanine (F), X3 is serine (S) and X4 is
      glutamic acid (E)
<220> FEATURE:
<221> NAME/KEY: MISC_FEATURE
<222> LOCATION: (9)..(12)
<223> OTHER INFORMATION: X3 may be alanine (A), glycine (G), or valine
      (V) and X1 is phenylalanine (F), X2 is cysteine (C) and X4 is
      glutamic acid (E)
<220> FEATURE:
<221> NAME/KEY: MISC_FEATURE
<222> LOCATION: (9)..(12)
<223> OTHER INFORMATION: X4 may be alanine (A), glycine (G), or valine
      (V) and X1 is phenylalanine (F), X2 is cysteine (C) and X3 is
      serine (S)

<400> SEQUENCE: 14

Arg Pro Pro Ser Ala Phe Phe Leu Xaa Xaa Xaa Xaa
1               5                   10

<210> SEQ ID NO 15
<211> LENGTH: 12
<212> TYPE: PRT
<213> ORGANISM: Artificial Sequence
<220> FEATURE:
<223> OTHER INFORMATION: immunostimulatory peptide
<220> FEATURE:
<221> NAME/KEY: MISC_FEATURE
<222> LOCATION: (9)..(9)
<223> OTHER INFORMATION: X may be alanine (A), glycine (G), valine (V),
      isoleucine (I), or leucine (L)

<400> SEQUENCE: 15

Arg Pro Pro Ser Ala Phe Phe Leu Xaa Cys Ser Glu
1               5                   10

<210> SEQ ID NO 16
<211> LENGTH: 12
<212> TYPE: PRT
<213> ORGANISM: Artificial Sequence
<220> FEATURE:
<223> OTHER INFORMATION: immunostimulatory peptide
<220> FEATURE:
<221> NAME/KEY: MISC_FEATURE
<222> LOCATION: (10)..(10)
<223> OTHER INFORMATION: X may be alanine (A), glycine (G), valine (V),
      isoleucine (I), or leucine (L)

<400> SEQUENCE: 16

Arg Pro Pro Ser Ala Phe Phe Leu Phe Xaa Ser Glu
1               5                   10

<210> SEQ ID NO 17
<211> LENGTH: 12
<212> TYPE: PRT
<213> ORGANISM: Artificial Sequence
<220> FEATURE:
<223> OTHER INFORMATION: immunostimulatory peptide
```

```
<220> FEATURE:
<221> NAME/KEY: MISC_FEATURE
<222> LOCATION: (11)..(11)
<223> OTHER INFORMATION: X may be alanine (A), glycine (G), valine (V),
      isoleucine (I), or leucine (L)

<400> SEQUENCE: 17

Arg Pro Pro Ser Ala Phe Phe Leu Phe Cys Xaa Glu
1               5                   10

<210> SEQ ID NO 18
<211> LENGTH: 12
<212> TYPE: PRT
<213> ORGANISM: Artificial Sequence
<220> FEATURE:
<223> OTHER INFORMATION: immunostimulatory peptide
<220> FEATURE:
<221> NAME/KEY: MISC_FEATURE
<222> LOCATION: (12)..(12)
<223> OTHER INFORMATION: X may be alanine (A), glycine (G), valine (V),
      isoleucine (I), or leucine (L)

<400> SEQUENCE: 18

Arg Pro Pro Ser Ala Phe Phe Leu Phe Cys Ser Xaa
1               5                   10

<210> SEQ ID NO 19
<211> LENGTH: 9
<212> TYPE: PRT
<213> ORGANISM: Artificial Sequence
<220> FEATURE:
<223> OTHER INFORMATION: immunostimulatory peptide
<220> FEATURE:
<221> NAME/KEY: MISC_FEATURE
<222> LOCATION: (6)..(6)
<223> OTHER INFORMATION: X is alanine (A), glycine (G), valine (V),
      isoleucine (I) or leucine (L)

<400> SEQUENCE: 19

Ser Ala Ser Ser Leu Xaa Cys Ser Glu
1               5

<210> SEQ ID NO 20
<211> LENGTH: 9
<212> TYPE: PRT
<213> ORGANISM: Artificial Sequence
<220> FEATURE:
<223> OTHER INFORMATION: immunostimulatory peptide
<220> FEATURE:
<221> NAME/KEY: MISC_FEATURE
<222> LOCATION: (7)..(7)
<223> OTHER INFORMATION: X is alanine (A), glycine (G), valine (V),
      isoleucine (I) or leucine (L)

<400> SEQUENCE: 20

Ser Ala Ser Ser Leu Phe Xaa Ser Glu
1               5

<210> SEQ ID NO 21
<211> LENGTH: 9
<212> TYPE: PRT
<213> ORGANISM: Artificial Sequence
<220> FEATURE:
<223> OTHER INFORMATION: immunostimulatory peptide
<220> FEATURE:
<221> NAME/KEY: MISC_FEATURE
<222> LOCATION: (8)..(8)
<223> OTHER INFORMATION: X is alanine (A), glycine (G), valine (V),
      isoleucine (I) or leucine (L)

<400> SEQUENCE: 21
```

Ser Ala Ser Ser Leu Phe Cys Xaa Glu
1               5

<210> SEQ ID NO 22
<211> LENGTH: 9
<212> TYPE: PRT
<213> ORGANISM: Artificial Sequence
<220> FEATURE:
<223> OTHER INFORMATION: immunostimulatory peptide
<220> FEATURE:
<221> NAME/KEY: MISC_FEATURE
<222> LOCATION: (9)..(9)
<223> OTHER INFORMATION: X is alanine (A), glycine (G), valine (V),
      isoleucine (I) or leucine (L)

<400> SEQUENCE: 22

Ser Ala Ser Ser Leu Phe Cys Ser Xaa
1               5

<210> SEQ ID NO 23
<211> LENGTH: 18
<212> TYPE: PRT
<213> ORGANISM: Artificial Sequence
<220> FEATURE:
<223> OTHER INFORMATION: immunostimulatory peptide
<220> FEATURE:
<221> NAME/KEY: MISC_FEATURE
<222> LOCATION: (15)..(15)
<223> OTHER INFORMATION: X is alanine (A), glycine (G), or valine (V)

<400> SEQUENCE: 23

Asp Pro Asn Ala Pro Lys Arg Pro Pro Ser Ala Ser Ser Leu Xaa Cys
1               5                   10                  15

Ser Glu

<210> SEQ ID NO 24
<211> LENGTH: 18
<212> TYPE: PRT
<213> ORGANISM: Artificial Sequence
<220> FEATURE:
<223> OTHER INFORMATION: immunostimulatory peptide
<220> FEATURE:
<221> NAME/KEY: MISC_FEATURE
<222> LOCATION: (16)..(16)
<223> OTHER INFORMATION: X is alanine (A), glycine (G), or valine (V)

<400> SEQUENCE: 24

Asp Pro Asn Ala Pro Lys Arg Pro Pro Ser Ala Ser Ser Leu Phe Xaa
1               5                   10                  15

Ser Glu

<210> SEQ ID NO 25
<211> LENGTH: 18
<212> TYPE: PRT
<213> ORGANISM: Artificial Sequence
<220> FEATURE:
<223> OTHER INFORMATION: immunostimulatory peptide
<220> FEATURE:
<221> NAME/KEY: MISC_FEATURE
<222> LOCATION: (17)..(17)
<223> OTHER INFORMATION: X is alanine (A), glycine (G), or valine (V)

<400> SEQUENCE: 25

Asp Pro Asn Ala Pro Lys Arg Pro Pro Ser Ala Ser Ser Leu Phe Cys
1               5                   10                  15

Xaa Glu

```
<210> SEQ ID NO 26
<211> LENGTH: 18
<212> TYPE: PRT
<213> ORGANISM: Artificial Sequence
<220> FEATURE:
<223> OTHER INFORMATION: immunostimulatory peptide
<220> FEATURE:
<221> NAME/KEY: MISC_FEATURE
<222> LOCATION: (18)..(18)
<223> OTHER INFORMATION: X is alanine (A), glycine (G) or valine (V)

<400> SEQUENCE: 26

Asp Pro Asn Ala Pro Lys Arg Pro Pro Ser Ala Ser Ser Leu Phe Cys
1               5                   10                  15

Ser Xaa

<210> SEQ ID NO 27
<211> LENGTH: 12
<212> TYPE: PRT
<213> ORGANISM: Artificial Sequence
<220> FEATURE:
<223> OTHER INFORMATION: immunostimulatory peptide
<220> FEATURE:
<221> NAME/KEY: MISC_FEATURE
<222> LOCATION: (9)..(9)
<223> OTHER INFORMATION: X is alanine (A), glycine (G), valine (V),
      isoleucine (I) or leucine (L)

<400> SEQUENCE: 27

Arg Pro Pro Ser Ala Ser Ser Leu Xaa Cys Ser Glu
1               5                   10

<210> SEQ ID NO 28
<211> LENGTH: 12
<212> TYPE: PRT
<213> ORGANISM: Artificial Sequence
<220> FEATURE:
<223> OTHER INFORMATION: immunostimulatory peptide
<220> FEATURE:
<221> NAME/KEY: MISC_FEATURE
<222> LOCATION: (10)..(10)
<223> OTHER INFORMATION: X is alanine (A), glycine (G), valine (V),
      isoleucine (I) or leucine (L)

<400> SEQUENCE: 28

Arg Pro Pro Ser Ala Ser Ser Leu Phe Xaa Ser Glu
1               5                   10

<210> SEQ ID NO 29
<211> LENGTH: 12
<212> TYPE: PRT
<213> ORGANISM: Artificial Sequence
<220> FEATURE:
<223> OTHER INFORMATION: immunostimulatory peptide
<220> FEATURE:
<221> NAME/KEY: MISC_FEATURE
<222> LOCATION: (11)..(11)
<223> OTHER INFORMATION: X is alanine (A), glycine (G), valine (V),
      isoleucine (I) or leucine (L)

<400> SEQUENCE: 29

Arg Pro Pro Ser Ala Ser Ser Leu Phe Cys Xaa Glu
1               5                   10

<210> SEQ ID NO 30
<211> LENGTH: 12
<212> TYPE: PRT
<213> ORGANISM: Artificial Sequence
<220> FEATURE:
```

<223> OTHER INFORMATION: immunostimulatory peptide
<220> FEATURE:
<221> NAME/KEY: MISC_FEATURE
<222> LOCATION: (12)..(12)
<223> OTHER INFORMATION: X is alanine (A), glycine (G), valine (V),
      isoleucine (I) or leucine (L)

<400> SEQUENCE: 30

Arg Pro Pro Ser Ala Ser Ser Leu Phe Cys Ser Xaa
1               5                   10

<210> SEQ ID NO 31
<211> LENGTH: 9
<212> TYPE: PRT
<213> ORGANISM: Artificial Sequence
<220> FEATURE:
<223> OTHER INFORMATION: immunostimulatory peptide

<400> SEQUENCE: 31

Ser Ala Phe Phe Leu Ala Cys Ser Glu
1               5

<210> SEQ ID NO 32
<211> LENGTH: 9
<212> TYPE: PRT
<213> ORGANISM: Artificial Sequence
<220> FEATURE:
<223> OTHER INFORMATION: immunostimulatory peptide

<400> SEQUENCE: 32

Ser Ala Phe Phe Leu Phe Ala Ser Glu
1               5

<210> SEQ ID NO 33
<211> LENGTH: 18
<212> TYPE: PRT
<213> ORGANISM: Artificial Sequence
<220> FEATURE:
<223> OTHER INFORMATION: immunostimulatory peptide

<400> SEQUENCE: 33

Asp Pro Asn Ala Pro Lys Arg Pro Pro Ser Ala Phe Phe Leu Ala Cys
1               5                   10                  15

Ser Glu

<210> SEQ ID NO 34
<211> LENGTH: 18
<212> TYPE: PRT
<213> ORGANISM: Artificial Sequence
<220> FEATURE:
<223> OTHER INFORMATION: immunostimulatory peptide

<400> SEQUENCE: 34

Asp Pro Asn Ala Pro Lys Arg Pro Pro Ser Ala Phe Phe Leu Phe Ala
1               5                   10                  15

Ser Glu

<210> SEQ ID NO 35
<211> LENGTH: 18
<212> TYPE: PRT
<213> ORGANISM: Artificial Sequence
<220> FEATURE:
<223> OTHER INFORMATION: immunostimulatory peptide

<400> SEQUENCE: 35

Asp Pro Asn Ala Pro Lys Arg Pro Pro Ser Ala Phe Phe Leu Phe Cys

Ala Glu

<210> SEQ ID NO 36
<211> LENGTH: 18
<212> TYPE: PRT
<213> ORGANISM: Artificial Sequence
<220> FEATURE:
<223> OTHER INFORMATION: immunostimulatory peptide

<400> SEQUENCE: 36

Asp Pro Asn Ala Pro Lys Arg Pro Pro Ser Ala Phe Phe Leu Phe Cys
1               5                   10                  15

Ser Ala

<210> SEQ ID NO 37
<211> LENGTH: 12
<212> TYPE: PRT
<213> ORGANISM: Artificial Sequence
<220> FEATURE:
<223> OTHER INFORMATION: immunostimulatory peptide

<400> SEQUENCE: 37

Arg Pro Pro Ser Ala Phe Phe Leu Ala Cys Ser Glu
1               5                   10

<210> SEQ ID NO 38
<211> LENGTH: 12
<212> TYPE: PRT
<213> ORGANISM: Artificial Sequence
<220> FEATURE:
<223> OTHER INFORMATION: immunostimulatory peptide

<400> SEQUENCE: 38

Arg Pro Pro Ser Ala Phe Phe Leu Phe Ala Ser Glu
1               5                   10

<210> SEQ ID NO 39
<211> LENGTH: 9
<212> TYPE: PRT
<213> ORGANISM: Artificial Sequence
<220> FEATURE:
<223> OTHER INFORMATION: immunostimulatory peptide
<220> FEATURE:
<221> NAME/KEY: MISC_FEATURE
<222> LOCATION: (6)..(6)
<223> OTHER INFORMATION: X may be alanine (A), glycine (G), valine (V),
      isoleucine (I), or leucine (L)
<220> FEATURE:
<221> NAME/KEY: MISC_FEATURE
<222> LOCATION: (7)..(7)
<223> OTHER INFORMATION: X is alanine (A), glycine (G), or valine (V)

<400> SEQUENCE: 39

Ser Ala Phe Phe Leu Xaa Xaa Ser Glu
1               5

<210> SEQ ID NO 40
<211> LENGTH: 9
<212> TYPE: PRT
<213> ORGANISM: Artificial Sequence
<220> FEATURE:
<223> OTHER INFORMATION: immunostimulatory peptide
<220> FEATURE:
<221> NAME/KEY: MISC_FEATURE
<222> LOCATION: (6)..(6)
<223> OTHER INFORMATION: X may be alanine (A), glycine (G), valine (V),
      isoleucine (I), or leucine (L)

```
<220> FEATURE:
<221> NAME/KEY: MISC_FEATURE
<222> LOCATION: (8)..(8)
<223> OTHER INFORMATION: X is alanine (A), glycine (G), or valine (V)

<400> SEQUENCE: 40

Ser Ala Phe Phe Leu Xaa Cys Xaa Glu
1               5

<210> SEQ ID NO 41
<211> LENGTH: 9
<212> TYPE: PRT
<213> ORGANISM: Artificial Sequence
<220> FEATURE:
<223> OTHER INFORMATION: immunostimulatory peptide
<220> FEATURE:
<221> NAME/KEY: MISC_FEATURE
<222> LOCATION: (6)..(6)
<223> OTHER INFORMATION: X may be alanine (A), glycine (G), valine (V),
      isoleucine (I), or leucine (L)
<220> FEATURE:
<221> NAME/KEY: MISC_FEATURE
<222> LOCATION: (9)..(9)
<223> OTHER INFORMATION: X is alanine (A), glycine (G), or valine (V)

<400> SEQUENCE: 41

Ser Ala Phe Phe Leu Xaa Cys Ser Xaa
1               5

<210> SEQ ID NO 42
<211> LENGTH: 12
<212> TYPE: PRT
<213> ORGANISM: Artificial Sequence
<220> FEATURE:
<223> OTHER INFORMATION: immunostimulatory peptide
<220> FEATURE:
<221> NAME/KEY: MISC_FEATURE
<222> LOCATION: (9)..(9)
<223> OTHER INFORMATION: X is alanine (A), glycine (G), or valine (V)
<220> FEATURE:
<221> NAME/KEY: MISC_FEATURE
<222> LOCATION: (10)..(10)
<223> OTHER INFORMATION: X is alanine (A), glycine (G), or valine (V)

<400> SEQUENCE: 42

Arg Pro Pro Ser Ala Phe Phe Leu Xaa Xaa Ser Glu
1               5                   10

<210> SEQ ID NO 43
<211> LENGTH: 12
<212> TYPE: PRT
<213> ORGANISM: Artificial Sequence
<220> FEATURE:
<223> OTHER INFORMATION: immunostimulatory peptide
<220> FEATURE:
<221> NAME/KEY: MISC_FEATURE
<222> LOCATION: (9)..(9)
<223> OTHER INFORMATION: X is alanine (A), glycine (G), or valine (V)
<220> FEATURE:
<221> NAME/KEY: MISC_FEATURE
<222> LOCATION: (11)..(11)
<223> OTHER INFORMATION: X is alanine (A), glycine (G), or valine (V)

<400> SEQUENCE: 43

Arg Pro Pro Ser Ala Phe Phe Leu Xaa Cys Xaa Glu
1               5                   10

<210> SEQ ID NO 44
<211> LENGTH: 12
<212> TYPE: PRT
<213> ORGANISM: Artificial Sequence
```

```
<220> FEATURE:
<223> OTHER INFORMATION: immunostimulatory peptide
<220> FEATURE:
<221> NAME/KEY: MISC_FEATURE
<222> LOCATION: (9)..(9)
<223> OTHER INFORMATION: X is alanine (A), glycine (G), or valine (V)
<220> FEATURE:
<221> NAME/KEY: MISC_FEATURE
<222> LOCATION: (12)..(12)
<223> OTHER INFORMATION: X is alanine (A), glycine (G), or valine (V)

<400> SEQUENCE: 44

Arg Pro Pro Ser Ala Phe Phe Leu Xaa Cys Ser Xaa
1               5                   10

<210> SEQ ID NO 45
<211> LENGTH: 8
<212> TYPE: PRT
<213> ORGANISM: Artificial Sequence
<220> FEATURE:
<223> OTHER INFORMATION: OVA-I peptide

<400> SEQUENCE: 45

Ser Ile Ile Asn Phe Glu Lys Leu
1               5

<210> SEQ ID NO 46
<211> LENGTH: 17
<212> TYPE: PRT
<213> ORGANISM: Artificial Sequence
<220> FEATURE:
<223> OTHER INFORMATION: OVA-II peptide

<400> SEQUENCE: 46

Ile Ser Gln Ala Val His Ala Ala His Ala Glu Ile Asn Glu Ala Gly
1               5                   10                  15

Arg

<210> SEQ ID NO 47
<211> LENGTH: 18
<212> TYPE: PRT
<213> ORGANISM: Artificial Sequence
<220> FEATURE:
<223> OTHER INFORMATION: Hp121 peptide

<400> SEQUENCE: 47

Ser Ile Gly Asp Val Ala Lys Lys Leu Gly Glu Met Trp Asn Asn Thr
1               5                   10                  15

Ala Ala

<210> SEQ ID NO 48
<211> LENGTH: 18
<212> TYPE: PRT
<213> ORGANISM: Artificial Sequence
<220> FEATURE:
<223> OTHER INFORMATION: scrambled Hp91 peptide

<400> SEQUENCE: 48

Ala Ser Leu Ala Pro Pro Phe Pro Asn Cys Phe Asp Pro Lys Ser Arg
1               5                   10                  15

Glu Phe

<210> SEQ ID NO 49
<211> LENGTH: 8
<212> TYPE: PRT
<213> ORGANISM: Artificial Sequence
```

```
<220> FEATURE:
<223> OTHER INFORMATION: UC18 peptide

<400> SEQUENCE: 49

Asp Pro Asn Ala Pro Lys Arg Pro
1               5

<210> SEQ ID NO 50
<211> LENGTH: 8
<212> TYPE: PRT
<213> ORGANISM: Artificial Sequence
<220> FEATURE:
<223> OTHER INFORMATION: UC411 peptide

<400> SEQUENCE: 50

Ala Pro Lys Arg Pro Pro Ser Ala
1               5

<210> SEQ ID NO 51
<211> LENGTH: 8
<212> TYPE: PRT
<213> ORGANISM: Artificial Sequence
<220> FEATURE:
<223> OTHER INFORMATION: UC714 peptide

<400> SEQUENCE: 51

Arg Pro Pro Ser Ala Phe Phe Leu
1               5

<210> SEQ ID NO 52
<211> LENGTH: 9
<212> TYPE: PRT
<213> ORGANISM: Artificial Sequence
<220> FEATURE:
<223> OTHER INFORMATION: UC1018 mutated peptide

<400> SEQUENCE: 52

Ala Ala Phe Phe Leu Phe Cys Ser Glu
1               5

<210> SEQ ID NO 53
<211> LENGTH: 9
<212> TYPE: PRT
<213> ORGANISM: Artificial Sequence
<220> FEATURE:
<223> OTHER INFORMATION: UC1018 mutated peptide

<400> SEQUENCE: 53

Ser Ala Ala Phe Leu Phe Cys Ser Glu
1               5

<210> SEQ ID NO 54
<211> LENGTH: 9
<212> TYPE: PRT
<213> ORGANISM: Artificial Sequence
<220> FEATURE:
<223> OTHER INFORMATION: UC1018 mutated peptide

<400> SEQUENCE: 54

Ser Ala Phe Ala Leu Phe Cys Ser Glu
1               5

<210> SEQ ID NO 55
<211> LENGTH: 9
<212> TYPE: PRT
<213> ORGANISM: Artificial Sequence
<220> FEATURE:
```

```
<223> OTHER INFORMATION: UC1018 mutated peptide

<400> SEQUENCE: 55

Ser Ala Phe Phe Ala Phe Cys Ser Glu
1               5

<210> SEQ ID NO 56
<211> LENGTH: 9
<212> TYPE: PRT
<213> ORGANISM: Artificial Sequence
<220> FEATURE:
<223> OTHER INFORMATION: UC1018 mutated peptide

<400> SEQUENCE: 56

Ser Ala Phe Phe Leu Phe Cys Ala Glu
1               5

<210> SEQ ID NO 57
<211> LENGTH: 9
<212> TYPE: PRT
<213> ORGANISM: Artificial Sequence
<220> FEATURE:
<223> OTHER INFORMATION: UC1018 mutated peptide

<400> SEQUENCE: 57

Ser Ala Phe Phe Leu Phe Cys Ser Ala
1               5

<210> SEQ ID NO 58
<211> LENGTH: 9
<212> TYPE: PRT
<213> ORGANISM: Artificial Sequence
<220> FEATURE:
<223> OTHER INFORMATION: UC1018 mutated peptide

<400> SEQUENCE: 58

Ser Ala Ser Ser Leu Phe Cys Ser Glu
1               5

<210> SEQ ID NO 59
<211> LENGTH: 9
<212> TYPE: PRT
<213> ORGANISM: Artificial Sequence
<220> FEATURE:
<223> OTHER INFORMATION: UC1018 mutated peptide

<400> SEQUENCE: 59

Ser Ala Ser Ser Leu Ser Cys Ser Glu
1               5
```

What is claimed is:

1. An immunostimulatory peptide consisting of the amino acid sequence SAFFLFCSE (SEQ ID NO: 1).

2. The immunostimulatory peptide of claim 1 joined to a tag or crosslinking agent.

3. The immunostimulatory peptide of claim 2, wherein the tag or crosslinking agent is selected from a group consisting of polyalkylene glycol (PAG) and a lipid.

4. The immunostimulatory peptide of claim 3, wherein the PAG is a polyethylene glycol (PEG).

5. The immunostimulatory peptide of claim 1 wherein the immunostimulatory peptide is monomeric, dimeric, trimeric, or tetrameric.

6. The immunostimulatory peptide of claim 5, wherein the immunostimulatory peptide exhibits an alpha helix conformation.

7. The immunostimulatory peptide of claim 6, wherein the alpha helix conformation provides a circular dichroism profile that shows negative peaks at about 205-206 nm or 222 nm.

8. The immunostimulatory peptide of claim 6, wherein the alpha helix conformation provides a circular dichroism profile that shows a positive peak below about 200 nm.

9. A method of enhancing an immune response in a subject comprising administering a sufficient amount of the immunostimulatory peptide of claim 1 thereby enhancing the immune response in the subject.

10. A method for selectively eliciting a cell-mediated immune response but not a humoral immune response in a subject comprising administering a sufficient amount of the immunostimulatory peptide of claim 1 thereby enhancing the cell-mediated immune response in the subject.

11. A method for selectively eliciting a cell-mediated immune response and a humoral immune response in a subject comprising administering a sufficient amount of the immunostimulatory peptide of claim 1 thereby enhancing the cell-mediated immune response and a humoral immune response in the subject.

* * * * *